United States Patent
Goto et al.

(10) Patent No.: US 8,129,544 B2
(45) Date of Patent: *Mar. 6, 2012

(54) 1-SUBSTITUTED-4-NITROIMIDAZOLE COMPOUND AND METHOD FOR PREPARING THE SAME

(75) Inventors: Fumitaka Goto, Tokushima (JP); Noriaki Takemura, Tokushima (JP); Tadaaki Otani, Matsushige (JP); Takeshi Hasegawa, Aizumi (JP); Hidetsugu Tsubouchi, Tokushima (JP); Naoto Utsumi, Naruto (JP); Shigekazu Fujita, Naruto (JP); Hideaki Kuroda, Tokushima (JP); Takuya Shitsuta, Matsushige (JP); Hirofumi Sasaki, Kitajima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 942 days.

This patent is subject to a terminal disclaimer.

(21) Appl. No.: 11/905,446

(22) Filed: Oct. 1, 2007

(65) Prior Publication Data

US 2008/0097107 A1   Apr. 24, 2008

Related U.S. Application Data

(62) Division of application No. 10/523,008, filed as application No. PCT/JP2003/013134 on Oct. 14, 2003, now Pat. No. 7,368,579.

(30) Foreign Application Priority Data

Oct. 15, 2002 (JP) .................................. 2002-299896
Feb. 17, 2003 (JP) .................................. 2003-037914

(51) Int. Cl.
*C07D 407/06* (2006.01)
(52) U.S. Cl. .................................. 548/321.5; 548/327.1
(58) Field of Classification Search ............... 548/321.5, 548/327.1
See application file for complete search history.

(56) References Cited

U.S. PATENT DOCUMENTS

| | | | |
|---|---|---|---|
| 3,493,582 A | 2/1970 | Hoffer | |
| 4,021,442 A | 5/1977 | Frank et al. | |
| 4,183,941 A | 1/1980 | Wyburn-Mason | |
| 4,925,949 A | 5/1990 | Massonneau et al. | |
| 5,380,866 A | 1/1995 | Barnett et al. | |
| 7,368,579 B2 | 5/2008 | Goto et al. | |
| 7,569,702 B2 * | 8/2009 | Shinhama .................. | 548/327.1 |
| 2008/0200689 A1 | 8/2008 | Goto et al. | |

FOREIGN PATENT DOCUMENTS

EP   1 555 267 A1   7/2005

OTHER PUBLICATIONS

Hoffer, M. et al., Nitroimidazoles II. Synthesis and Reactions of Iodonitroimidazoles (1), Journal of Heterocyclic Chemistry, vol. 3, No. 4, 1966, pp. 454-458.
Office Action issued in Copending U.S. Appl. No. 12/007,776 dated Nov. 6, 2009.
Hoffer, CA 68:21933, 1968.
Nurgatin et al., "Synthesis of Mercaptonitroimidazoles and Their Reactions With 2,4,6-trinitrochlorobenzenes," CA 97:109931 (1982).
Chem. Abs. 111:232816; PL 145536; Sep. 20, 1998, 1 page.
Taiwanese Office Action issued in Taiwanese Application No. 092128442 dated Mar. 7, 2008; 4 pages.
English-language translation of Taiwanese Office Action issued in Taiwanese Application No. 092128442; 3 pages, 2008.
Nagarajan et al., CA 101:211044, 1984.
Suwinski et al,, "Nitroimdazoles. Part V. Chloronitroimidazoles From Dinitroimidazoles. A Reinvestigation," Polish Journal of Chemistry, (formerly Roczniki Chemii), vol. 56, pp. 1261-1272 (1982).
European Search Report for Application No. EP 03756610.6-2101 dated Feb. 2, 2011, 6 pages.

* cited by examiner

*Primary Examiner* — Laura L. Stockton
(74) *Attorney, Agent, or Firm* — Finnegan, Henderson, Farabow, Garrett & Dunner LLP

(57) ABSTRACT

The present invention relates to a 1-substituted-4-nitroimidazole compound represented by the general formula (1) or a salt thereof,

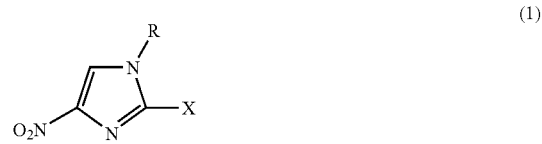

(1)

(wherein R is a hydrogen atom, a lower alkoxy group-substituted lower alkyl group, a phenyl-lower alkoxy group-substituted lower alkyl group, a cyano-substituted lower alkyl group, a phenyl-lower alkyl group which may have lower alkoxy groups as the substituents in the phenyl ring or a group of the formula —CH$_2$R$^4$; X is a halogen atom or a group of the formula —S(O)n-R$^1$) and method for preparing the same. The compound of the formula (1) is a useful compound as an intermediate for synthesis of various pharmaceutical and agricultural chemicals, particularly, as intermediates for antitubercular agents.

3 Claims, No Drawings

1-SUBSTITUTED-4-NITROIMIDAZOLE COMPOUND AND METHOD FOR PREPARING THE SAME

This application is a divisional of application Ser. No. 10/523,008, filed Feb. 1, 2005, now U.S. Pat. No. 7,368,579, issued May 6, 2008, which is a §371 of International Application No. PCT/JP2003/013134, filed Oct. 14, 2003, and claims priority of Japanese Applications No. 2002-299896, filed Oct. 15, 2002 and No. 2003-37914, filed Feb. 17, 2003, the contents of all of which are incorporated herein by reference.

TECHNICAL FIELD

The present invention relates to a 1-substituted-4-nitroimidazole compound and method for preparing the same.

BACKGROUND ART

The 4-nitroimidazole compound and salt thereof represented by the general formula (2),

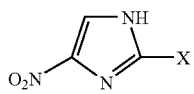

(2)

[wherein, X is a halogen atom or a group of the formula —S(O)$_n$—R$^1$; n is 0 or an integer of 1 or 2; and R$^1$ is a phenyl group which may have 1 to 3 substituents, selected from the group consisting of a nitro group, a halogen atom and a lower alkyl group, in the phenyl ring],
is a useful compound as intermediate for synthesis of various pharmaceuticals and agricultural chemicals, particularly, as intermediates for preparing antitubercular agents.

Up to now, methods for preparing 4-nitroimidazole compound of the general formula (2) are known, for example, methods shown by the following Reaction scheme-1 and Reaction scheme-2. [Cf. Jerzy SUWINSKI, Ewa SALWINSKA, Jan WATRAS and Maria WIDEL, Polish Journal of Chemistry, 56, 1261-1272, (1982)].

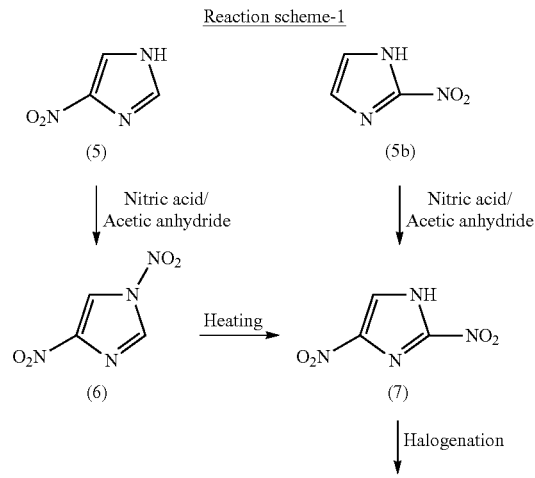

Reaction scheme-1

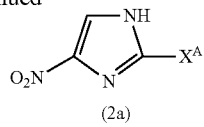

(2a)

Reaction scheme-2

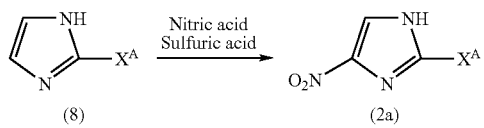

In the Reaction scheme-1 and -2, X$^A$ is a halogen atom.

However, these methods involve several drawbacks, thus, they are not suitable for industrially applicable methods of preparation. For example, in the method shown by Reaction scheme-1, compound (6) and compound (7) as intermediates for the reaction are chemically unstable compounds, thus these compounds are in danger of explosion caused by shocks of dropping, frictions and others. Further, in the reaction for introducing compound (7) by heating (at about 130° C.) compound (6), this temperature exceeds TNR temperature (Temperature of No Return: an allowable maximum temperature around 60 to 70° C., at which the compound (6) can be handled safely in a chemical process equipment), for this reason, this method involves very danger for conducting in a large scale industrial production of these objective compounds.

While, in the method shown by Reaction scheme-2, the reaction is a nitration of a compound (8). However, by this nitration, the objective compound (2a) can be only obtained in low yield, thus this method is industrially disadvantageous.

DISCLOSURE OF THE INVENTION

The present invention is directed to provide a 1-substituted-4-nitroimidazole compound or a salt thereof and the process for preparing the same.

One object of the present invention is to provide a method for preparing a 4-nitroimidazole compound represented by the general formula (2a) of high purity in high yield, by more safety method which brings less dangers such as explosion and others. Another object of the present invention is to provide a novel 1-substituted-4-nitroimidazole compound represented by the general formula (10) and a 4-nitroimidazole compounds represented by the general formulas (2b) or (2c), those of which may be useful as intermediates for preparing antitubercular agents.

The present inventors have intensively conducted research works to develop for the purpose to achieve the above-mentioned objectives, that provide methods for preparing a 4-nitroimidazole compound represented by the general formula (2a) and a novel 1-substituted-4-nitroimidazole compound which can be used as intermediates for preparing antitubercular agents. As the results, the present inventors have found that the above-mentioned objectives can be achieved, by the use of a 4-nitroimidazole compound represented by the general formula (3), a 4-nitroimidazole compound represented by the general formula (4), a 4-nitroimidazole compound represented by the general formula (25), a 1-nitroimidazole compound represented by the general formula (26), a 1-substituted-4-nitroimidazole compound represented by the general formula (10) or a 4-nitroimidazole compound represented by the general formula (2b) or (2c) as the intermediates, and a nitration of an imidazole compound represented by the general formula (15) by novel method.

Thus, according to the research works made by the present inventors, we have found the facts that: 1) by removing $R^{A'}$-group from a 1-substituted-4-nitroimidazole compound represented by the general formula (1a), obtained by reducing a 4-nitroimidazole compound represented by the general formula (3), 2) by reducing a 4-nitroimidazole compound represented by the general formula (4), or 3) by nitrating imidazole compound represented by the general formula (15) by novel method; a 4-nitroimidazole compound represented by the general formula (2a) with high purity can be prepared in high yield, by more safety method which brings less dangers.

Further, the present inventors have found the fact that, a 1-substituted-4-nitroimidazole compound represented by the general formula (1) formed on the way of this method is a novel compound which has not been known before in any literature.

The present invention has been successfully completed on the basis of the above mentioned findings and knowledges. Thus, the present invention is explained as follows:

1) The present invention relates to a 1-substituted-4-nitroimidazole compound represented by the general formula (1),

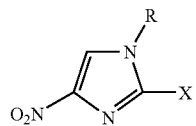

(1)

[wherein R is a hydrogen atom, a lower alkoxy group-substituted lower alkyl group, a phenyl-lower alkoxy group-substituted lower alkyl group, a cyano group-substituted lower alkyl group, a phenyl-lower alkyl group which may have a lower alkoxy group as the substituents in the phenyl ring, or a group of the formula —$CH_2R^A$; $R^A$ is a group of the following formula,

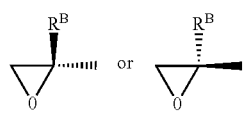

wherein $R^B$ is a hydrogen atom or a lower alkyl group; X shows a halogen atom or a group of the formula —$S(O)n-R^1$; n is 0 or an integer of 1 or 2; and $R^1$ is a phenyl group which may have 1 to 3 substituents, selected from the group consisting of a nitro group, a halogen atom and a lower alkyl group, in the phenyl ring; provided that when X is a halogen atom, then R should not be a hydrogen atom], or a salt thereof.

2) The present invention relates to a method for preparing a 4-nitroimidazole compound represented by the general formula (2a),

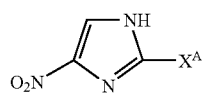

(2a)

[wherein, $X^A$ is a halogen atom], which is characterized by reducing a 4-nitroimidazole compound represented by the general formula (3),

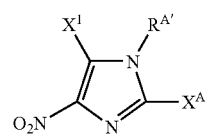

(3)

[wherein $R^{A'}$ is a lower alkoxy group-substituted lower alkyl group, a phenyl-lower alkoxy group-substituted lower alkyl group, a cyano group-substituted lower alkyl group, a phenyl-lower alkyl group which may have a lower alkoxy group as the substituent in the phenyl ring; $X^A$ and $X^1$ are each a halogen atom]

and removing the $R^{A'}$ group from the obtained 1-substituted-4-nitroimidazole compound represented by the general formula (1a),

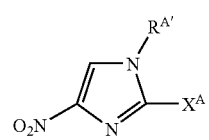

(1a)

[wherein $R^{A'}$ and $X^A$ are the same as defined above].

3) The present invention relates to method for presenting a 4-nitroimidazole compound represented by the general formula (2a),

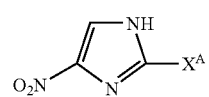

(2a)

[wherein $X^A$ is the same as defined previously], which is characterized by reducing a 4-nitroimidazole compound represented by the general formula (4),

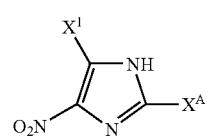

(4)

[wherein $X^A$ and $X^1$ are the same as defined previously].

4) The present invention relates to a method for preparing a 1-substituted-4-nitroimidazole compound represented by the general formula (10),

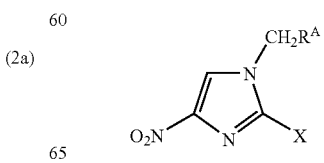

(10)

[wherein $R^A$ and X are the same as defined previously], which is characterized by reacting a 4-nitroimidazole compound represented by the general formula (2),

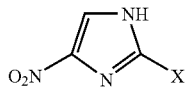
(2)

[wherein X is the same as defined previously], with a glycidyl benzenesulfonate represented by the general formula (11),

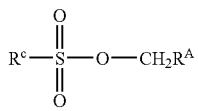
(11)

[wherein $R^A$ is a group of the following formula

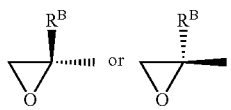

wherein $R^B$ is a hydrogen atom or a lower alkyl group; and $R^C$ is a group of the formula,

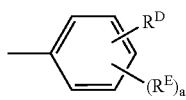

wherein $R^D$ is a nitro group; $R^E$ is a halogen atom or a lower alkyl group; a is 0, or an integer of 1 or 2; provided that when a is 2, then two of $R^E$ may be the same or different].

5) The present invention relates to a method for preparing a 4-nitroimidazole compound represented by the general formula (2b) or (2c),

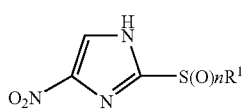
(2b) or (2c)

[wherein $R^1$ and n are the same as defined previously], which is characterized by removing $R^{A'}$ group from a 1-substituted-4-nitroimidazole compound represented by the general formula (25) or (25a),

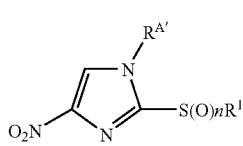
(25) or (25a)

[wherein $R^{A'}$, n and $R^1$ are the same as defined previously].

6) The present invention relates to a method for preparing a 4-nitroimidazole compound represented by the general formula (2b),

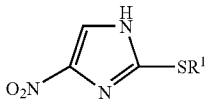
(2b)

[wherein $R^1$ is the same as defined previously], which is characterized by rearranging a 1-nitroimidazole compound represented by the general formula (26),

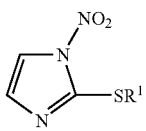
(26)

[wherein $R^1$ are the same as defined previously].

7) The present invention relates to a method for preparing a 4-nitroimidazole compound represented by the general formula (25a), (2c) or (10d),

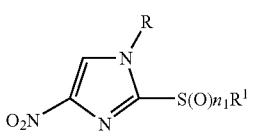
(25a), (2c) or (10d)

[wherein $R^1$ and R are the same as defined previously: $n_1$ is an integer of 1 or 2],
which is characterized by oxidizing a 4-nitroimidazole compound represented by the general formula (25), (2b) or (10c),

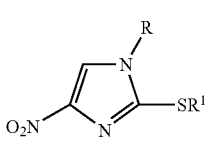
(25), (2b) or (10c)

[wherein $R^1$ and R are the same as defined previously].

8) The present invention relates to a method for preparing a 4-nitroimidazole compound represented by the general formula (15a),

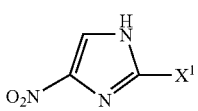
(15a)

[wherein $X^1$ is the same as defined previously],
which is characterized by nitrating an imidazole compound represented by the general formula (15),

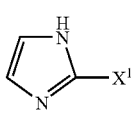
(15)

[wherein $X^1$ is the same as defined previously] in the presence of a nitronium halogenated borate.

9) The present invention relates to a process for preparing the 4-nitroimidazole compound as mentioned in the above item 8), wherein the nitronium halogenated borate is nitronium tetrafluoroborate.

10) The present invention relates to a method for preparing 4-nitroimidazole compound as mentioned in the above item 9), wherein the nitration is conducted in nitromethane.

11) The present invention relates to a method for preparing a 1-substituted-4-nitroimidazole compound represented by the general formula (10c),

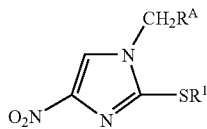

(10c)

[wherein R¹ and R^A are the same as defined previously], which is characterized by nitrating a 1-substituted imidazole compound represented by the general formula (27),

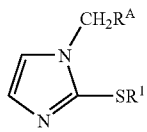

(27)

[wherein R¹ and R^A are the same as defined previously].

12) The present invention relates to a 4-nitroimidazole derivative represented by the general formula (41),

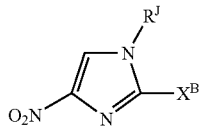

(41)

[wherein, $X^B$ is a bromine atom, or a group of —S(O)nR¹ (wherein R¹ and n are the same as defined previously); $R^J$ is a group of the formula,

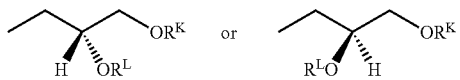

(wherein $R^K$ and $R^L$ are each, respectively a tetrahydropyranyl group, a tri(lower alkyl)silyl group, a lower alkanoyl group, a phenyl-lower alkyl group which may have a lower alkoxy groups as the substituents in the phenyl ring or a hydrogen atom)] or a salt thereof.

13) The present invention provides (S)-2-bromo-1-(2-methyl-2-oxiranylmethyl)-4-nitroimidazole or a salt thereof.

14) The present invention provides (R)-2-bromo-1-(2-methyl-2-oxiranylmethyl)-4-nitroimidazole or a salt thereof.

15) The present invention provides (S)-2-chloro-1-(2-methyl-2-oxiranylmethyl)-4-nitroimidazole or a salt thereof.

16) The present invention provides (R)-2-chloro-1-(2-methyl-2-oxiranylmethyl)-4-nitroimidazole or a salt thereof.

MODE FOR CARRYING OUT OF THE INVENTION

In the present invention, 1-substituted-4-nitroimidazole compounds of the general formula (1) and 1-substituted-4-nitroimidazole compounds of the general formula (10) are novel compounds which have not been known in any literature.

1-Substituted-4-nitroimidazole compounds of the general formula (1) are useful as intermediates for synthesis of various pharmaceuticals and agricultural chemicals, particularly, as intermediates for synthesis of 4-nitroimidazole compounds of the general formula (2) being useful as intermediates for preparing antitubercular agents. Further, 1-substituted-4-nitroimidazole compounds of the general formula (10) are useful as intermediates for preparing antitubercular agents.

Each of groups shown in the above mentioned general formula (1) are specifically explained as follows.

As to the halogen atoms, a fluorine atom, chlorine atom, bromine atom and iodine atom can be exemplified.

As to the lower alkoxy group-substituted lower alkyl group, a straight chain or branched chain alkyl group having 1 to 6 carbon atoms, in which 1 to 2 straight chain or branched chain alkoxy group having 1 to 6 carbon atoms are substituted, for example, methoxymethyl, 3-methoxypropyl, ethoxymethyl, diethoxymethyl, dimethoxymethyl, 1-ethoxyethyl, 3-ethoxypropyl, 4-ethoxybutyl, 5-isopropoxypentyl, 6-(n-propoxy)hexyl, 1,1-dimethyl-2-butoxyethyl, 2-methyl-3-tert-butoxypropyl, 2-(n-pentyloxy)ethyl, n-hexyloxymethyl groups and the like can be exemplified.

As to the phenyl-lower alkoxy group-substituted lower alkyl group, a straight chain or branched chain alkyl group having 1 to 6 carbon atoms, in which the phenylalkoxy group wherein the alkoxy moiety is a straight chain or branched chain alkoxy group having 1 to 6 carbon atoms, is substituted, for example, benzyloxymethyl, (2-phenylethoxy)methyl, (1-phenylethoxy)methyl, 3-(3-phenylpropoxy)propyl, 4-(4-phenylbutoxy)butyl, 5-(5-phenylpentyloxy)pentyl, 6-(6-phenylhexyloxy)hexyl, 1,1-dimethyl-(2-phenylethoxy)ethyl, 2-methyl-3-(3-phenylpropoxy)-propyl, 2-benzyloxyethyl, 1-benzyloxyethyl, 3-benzyloxypropyl, 4-benzyloxybutyl, 5-benzyloxypentyl, 6-benzyloxyhexyl groups and the like can be exemplified.

As to the phenyl-lower alkyl group which may have straight chain or branched chain alkoxy groups as substituents in the phenyl ring, a phenylalkyl group wherein the alkyl moiety is a straight chain or branched chain alkyl group having 1 to 6 carbon atoms, and the phenyl ring may have 1 to 3 straight chain or branched chain alkoxy groups having 1 to 6 carbon atoms, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, 4-methoxybenzyl, 3-methoxybenzyl, 2-methoxybenzyl, 3,4-dimethoxybenzyl, 3,4,5-trimethoxybenzyl, 2-(4-ethoxyphenyl)ethyl, 1-(3-propoxyphenyl)ethyl, 3-(2-butoxyphenyl)propyl, 4-(4-pentyloxyphenyl)butyl, 5-(4-hexyloxyphenyl)pentyl, 6-(2,4-diethoxyphenyl)hexyl, 1,1-dimethyl-2-(3-methoxy-4-ethoxyphenyl)ethyl, 2-methyl-3-(2-methoxy-6-propoxyphenyl)propyl groups and the like can be exemplified.

As to the cyano-substituted lower alkyl group, a cyanoalkyl group wherein the alkyl moiety is a straight chain or branched chain alkyl group having 1 to 6 carbon atoms, for example, cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl groups and the like can be exemplified.

As to the phenyl group which may have 1 to 3 substituents selected from the group consisting of a nitro group, a halogen atom and a lower alkyl group in the phenyl ring, a phenyl group which may have 1 to 3 substituents selected from the group consisting of a nitro group, a halogen atom and a straight chain or branched chain alkyl group having 1 to 6 carbon atoms in the phenyl ring, for example, phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-nitrophenyl, 3-nitrophenyl, 4-nitrophenyl, 3,4-dinitrophenyl, 2,4-dinitrophenyl, 2,5-dinitrophenyl, 2,6-dinitrophenyl, 3,4,5-trinitrophenyl, 4-fluorophenyl, 2,5-difluorophenyl, 2,4-difluorophenyl, 3,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3-fluorophenyl, 2-fluorophenyl, 4-iodophenyl, 2-bromophenyl, 3-bromophenyl, 4-bromophenyl, 3,5-dichlorophenyl, 2,4,6-trifluorophenyl, 2-iodophenyl, 3-iodophenyl, 2,3-dibromophenyl, 2,4-diiodophenyl, 2,4,6-trichlorophenyl, 2-chloro-4-nitrophenyl, 3-nitro-4-methylphenyl, 3-ethyl-2-nitrophenyl, 2-fluoro-4-nitro-6-methylphenyl groups and the like can be exemplified.

As to the lower alkyl group, a straight chain or branched chain alkyl group having 1 to 6 carbon atoms, for example, methyl, ethyl, propyl, isopropyl, n-butyl, isobutyl, tert-butyl, n-pentyl, n-hexyl groups can be exemplified.

In the 1-substituted-4-nitroimidazole compounds represented by the general formula (10) of the present invention, the compounds represented by the general formula (10a) and (10b) are involved.

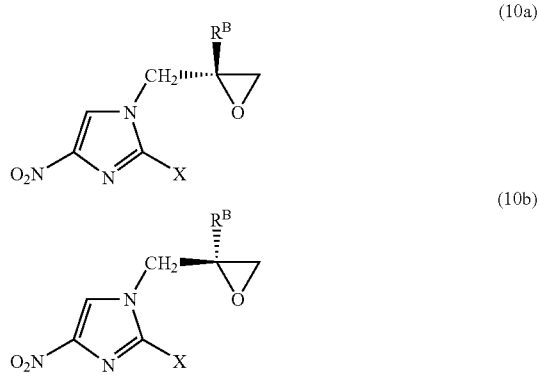

Method for preparing a 4-nitroimidazole compound of the general formula (2) of the present invention is explained as follows.

The 4-nitroimidazole compound of the general formula (2) is prepared by the following Reaction scheme-3.

Reaction scheme-3

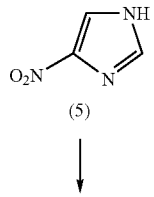

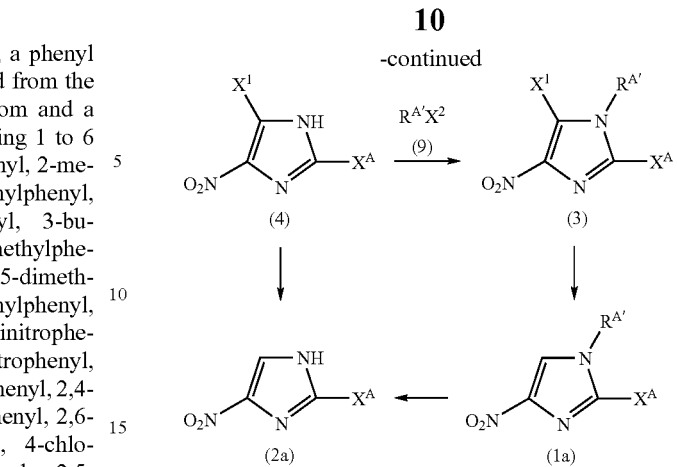

[wherein, $R^{A'}$, $X^A$ and $X^1$ are the same as defined above; $X^2$ is a halogen atom or a lower alkoxy group.

As to the lower alkoxy group, a straight chain or branched chain alkoxy group having 1 to 6 carbon atoms, for example, methoxy, ethoxy, propoxy, isopropoxy, n-butoxy, isobutoxy, tert-butoxy, n-pentyloxy, n-hexyloxy group and the like can be exemplified, and particularly, methoxy group and ethoxy group are preferable.

In the above Reaction scheme-3, the reaction of obtaining compound (4) from compound (5) can be carried out in a suitable solvent and in the presence of a halogenating agent.

As to the halogenating agents to be used in the reaction, for example, halogen molecules such as bromine, chlorine, iodine and the like, iodine chloride, sulfuryl chloride, copper compounds such as copper(II) bromide, N-halogenated succinimides such as N-bromosuccinimide, N-chlorosuccinimide and the like, halogenated alkanes such as hexachloroethane and the like can be exemplified. The halogenating agent may be used, generally in an equimolar to 10 times molar quantity, preferably in an equimolar to 5 times molar quantity per one molar quantity of compound (5).

As to the solvents, for example, water; halogenated hydrocarbons, such as dichloromethane, dichloroethane, chloroform, carbon tetrachloride and the like; ethers such as tetrahydrofuran, diethyl ether, dioxane, di(ethylene glycol)dimethyl ether, dimethoxyethane and the like; aliphatic hydrocarbons such as n-hexane, cyclohexane and the like; fatty acids such as acetic acid, propionic acid, and the like; carbon disulfide and the like; and mixtures of these solvents and the like can be exemplified.

In carrying out of the reaction, an inorganic base, such as sodium hydroxide, sodium carbonate, sodium hydrogencarbonate, potassium hydroxide, potassium carbonate, potassium hydrogencarbonate or the like; an alkyl lithium such as n-butyl lithium may be added in the reaction system.

The reaction is carried out, generally at −50 to 150° C., preferably at −50 to 100° C., for about 5 minutes to 10 hours.

In the reaction of compound (4) with compound (9), when $X^2$ is a halogen atom, then the reaction is conducted in a suitable solvent and in the presence or absence of the basic compound.

As to the solvents to be used in the reaction, aromatic hydrocarbons such as benzene, toluene, xylene and the like; ethers such as diethyl ether, tetrahydrofuran, dioxane, di(ethylene glycol) dimethyl ether, dimethoxyethane and the like; halogenated hydrocarbons such as dichloromethane, dichloroethane, chloroform, carbon tetrachloride; lower alcohols such as methanol, ethanol, isopropanol, n-butanol, tert-butanol and the like; acetic acid; esters such as ethyl acetate, methyl acetate, n-butyl acetate and the like; ketones such as acetone, methylethyl ketone and the like; acetonitrile, pyridine, 2,4,6-collidine, dimethyl sulfoxide, N,N-dimethylformaide, N,N-dimethylacetamide, 1-methyl-2-pyrrolidinone (NMP), hexamethylphosphorous triamide; and mixtures of these solvents and the like can be exemplified.

As to the basic compounds, inorganic bases, for example, metal carbonates such as sodium carbonate, potassium carbonate, sodium hydrogencarbonate, potassium hydrogencarbonate and the like; metal hydroxides such as sodium hydroxide, potassium hydroxide, calcium hydroxide and the like; and sodium hydride, potassium, sodium, sodium amide; metal alcoholates such as sodium methylate, sodium ethylate and the like; and organic bases, for example, pyridine, 2,4,6-collidine, N-ethyldiisopropylamine, dimethylaminopyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like can be exemplified.

The amount of the basic compound may be, generally 1 to 5 molar quantities per 1 mole of compound (4).

The amount of compound (9) may be, generally at least an equimolar quantity, preferably 1 to 5 molar quantities per 1 mole of compound (4).

The reaction is carried out, generally at about −50 to 200° C., preferably at about −50 to 150° C., and generally for about 1 to 30 hours. An alkali metal halides such as sodium iodide or the like may be added in the reaction system.

In the reaction of compound (4) with compound (9), when $X^2$ is a lower alkoxy group, under the above mentioned reaction condition, an acid, for example, sulfonic acid such as camphorsulfonic acid or p-toluenesulfonic acid may be used in place of the basic compound.

The amount of the acid may be, generally a catalytic amount, preferably, 0.01 to 0.2 molar quantity per 1 mole of compound (4).

The reaction for obtaining compound (1a) from compound (3) and the reaction for obtaining compound (2a) from compound (4) are carried out in a suitable solvent and in the presence of a reducing agent.

As to the reducing agent to be used in the reaction, for example, metal sulfite such as sodium sulfite, sodium hydrogensulfite and the like; tetra-lower alkyl ammonium borohydrides such as tetramethyl ammonium borohydride, tetraethyl ammonium borohydride, tetra-n-butyl ammonium borohydride, tetra-n-butyl ammonium cyanoborohydride and the like; hydride reducing agents such as sodium cyanoborohydride, lithium cyanoborohydride, sodium borohydride, diborane and the like can be exemplified.

As to the solvents to be used in the reaction, for example, water, lower alcohols such as methanol, ethanol, isopropanol and the like, ketones such as acetone, methyl ethyl ketone and the like, ethers such as diethyl ether, tetrahydrofuran, diisopropyl ether, diglyme, 1,4-dioxane, dimethyoxyethane and the like, aromatic hydrocarbons such as benzene, toluene, xylene and the like, dimethyl sulfoxide, N,N-dimethylformamide, N,N-dimethylacetamide, 1-methyl-2-pyrrolidinone (NMP), and mixtures of these solvents and the like can be exemplified.

In the case that diborane is used as the reducing agent, an anhydrous solvent may be preferably used.

The amount of the reducing agent is generally at least an equimolar quantity, preferably about 1 to 10 molar quantities per 1 mole of compound (3) or compound (4).

The reaction is carried out, generally at about 0 to 150° C., preferably at about 0 to 120° C., and is finished in about 1 to 30 hours.

Compound (1a) or (2a) can be obtained by the reaction in a suitable solvent, which is carried out by using a reducing agent, for example, a catalytic hydrogenation reducing agent, such as palladium, palladium-black, palladium-carbon, palladium hydroxide-carbon, rhodium-alumina, platinum, platinum oxide, copper chromite, Raney nickel, palladium acetate and the like; and a fatty acid, an ammonium salt of fatty acid or an alkali metal salt of fatty acid, such as formic acid, sodium formate, ammonium formate, sodium acetate and the like, under the reaction temperature of, generally a room temperature to 200° C., preferably a room temperature to 150° C., for about 1 to 30 hours.

The solvent to be used in this reaction is any solvent which is capable to be used in the reduction with using the above-mentioned catalytic hydrogenation reducing agent. In this reaction, amines such as triethylamine and the like, and phosphorous compounds such as tri-ortho-tolylphosphine and the like may be added.

The amount of the catalytic hydrogenation reducing agent may be, generally about 0.1 to 40% by weight, preferably 0.1 to 20% by weight per 1 mole of compound (3) or compound (4). The amount of the fatty acid, ammonium salt of fatty acid or metal salt of fatty acid may be, generally at least an equimolar quantity, preferably about 1 to 20 molar quantity per 1 mole of compound (3) or compound (4).

The reaction can be carried out, in a suitable solvent, by reducing the compound (3) or compound (4) in the presence of the catalytic hydrogenation reducing agent. As to the solvent to be used in the reaction, for example, water; fatty acids such as acetic acid and the like; alcohols such as methanol, ethanol, isopropanol and the like; aliphatic hydrocarbons such as n-hexane, cyclohexane and the like; ethers such as 1,4-dioxane, tetrahydrofuran, diethyl ether, monoglyme, diglyme, dimethoxyethane and the like; esters such as ethyl acetate, methyl acetate, n-butyl acetate and the like; aprotic solvents such as N,N-dimethylformamide N,N-dimethylacetamide, 1-methyl-2-pyrrolidinone (NMP) and the like; and mixtures of these solvents can be exemplified. As to the catalytic hydrogenation reducing agent, for example palladium, palladium acetate, palladium-black, palladium-carbon, palladium hydroxide-carbon, rhodium-alumina, platinum, platinum oxide, copper chromite, Raney nickel and the like can be exemplified. The amount of the catalytic hydrogenation reducing agent is, generally about 0.02 to 1 part by weight per 1 mole of compound (3) or compound (4). The reaction temperature may be, generally at about −20 to 100° C., preferably, at about 0 to 80° C., and hydrogen pressure may be, generally about 1 to 10 atmospheric pressure. The reaction is generally finished about 0.5 to 20 hours. The reaction is proceeded advantageously by adding amines such as triethylamine to the reaction system.

Compound (1a) or compound (2a) can be obtained by reacting, in a suitable solvent, in the presence of a catalyst, generally at a room temperature to 200° C., preferably at a room temperature to 150° C., for about 1 to 10 hours. As to the solvent to be used in the reaction, any solvent to be used in the above-mentioned reduction with the hydrogenation reducing agent can be also used. As to the catalyst, palladium compounds such as palladium acetate-triphenylphosphine, tetrakis(triphenylphosphine)palladium and the like can be exemplified. The amount of the catalyst may be about 0.01 to 5 molar quantities, preferably about 0.01 to an equimolar quantity per 1 mole of compound (3) or compound (4). The reaction is advantageously proceeded by adding an alkyl silane compound such as triethyl silane to the reaction system.

In accordance with this reducing reaction, the desired compound of the general formula (1a) or (2a) wherein, 5-position of imidazole ring is selectively dehalogenated can be obtained, this fact has been firstly found by the present inventors.

The reaction for obtaining compound (2a) from compound (1a) can be carried out in a suitable solvent or without a solvent, in the presence of a basic compound or acid compound.

As to the solvents to be used in this reaction, for example, water; lower alcohols such as, methanol, ethanol, isopropanol and the like; ketones such as acetone, methyl ethyl ketone and the like; ethers such as diethyl ether, dioxane, tetrahydrofuran, ethylene glycol dimethyl ether, dimethoxyethane and the like; esters such as ethyl acetate, methyl acetate, n-butyl acetate and the like; fatty acids such as acetic acid, formic acid and the like; N,N-dimethylacetamide, 1-methyl-2-pyrrolidinone (NMP) and mixtures of these solvents and the like can be exemplified.

As to the basic compounds, those of well-known can be used widely. Any one of the basic compounds used in the reaction of compound (4) with compound (9), when $X^2$ is a halogen atom, can be used.

As to the acids, those of well-known can be used widely, for example, mineral acids such as hydrochloric acid, sulfuric acid, hydrobromic acid and the like; formic acid, acetic acid, trifluoroacetic acid; aromatic sulfonic acids such as p-toluenesulfonic acid can be exemplified.

The reaction is generally carried out at about 0 to 150° C., preferably at about 0 to 100° C., and is generally finished for about 5 minutes to 30 hours.

In case of using an acid in this reaction, anisol and the like may be added to the reaction system.

1-Substituted-4-nitroimidazole compound represented by the general formula (10) is prepared for example by the following Reaction scheme-4.

Reaction scheme-4

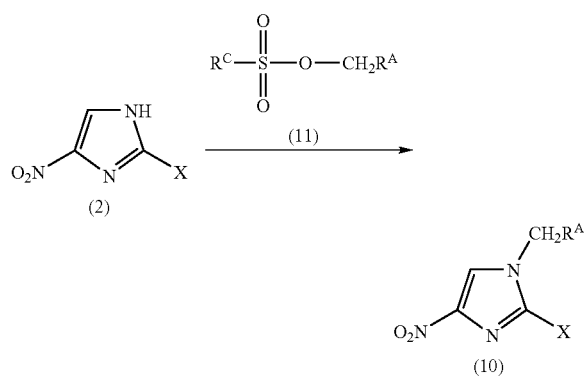

[wherein, $R^A$, $R^C$ and X are the same as defined above].

The reaction of 4-nitroimidazole compound represented by the general formula (2) with compound (11) is carried out in a suitable solvent, in the presence of a basic compound.

As to the solvent to be used in the reaction, for example, aromatic hydrocarbons such as benzene, toluene, xylene, o-chlorobenzene, m-chlorobenzene, 2,3-dichlorobenzene and the like; ethers such as diethyl ether, tetrahydrofuran, dioxane, di(ethylene glycol) dimethyl ether, dimethoxyethane and the like; halogenated hydrocarbons such as dichloromethane, dichloroethane, chloroform, carbon tetrachloride and the like; lower alcohols such as methanol, ethanol, isopropanol, butanol, tert-butanol and the like; acetic acid; esters such as ethyl acetate, methyl acetate, n-butyl acetate and the like; ketones such as acetone, methyl ethyl ketone and the like; acetonitril, pyridine, 1-methyl-2-pyrrolidinone (NMP), 2,4,6-collidine, dimethyl sulfoxide, N,N-dimethylformamide, N,N-dimethylacetamide, hexamethylphosphorous triamide; and mixtures of these solvents and the like can be exemplified.

As to the basic compound, well-known inorganic bases and organic bases can be widely used.

As to the inorganic bases, for example, alkali metal carbonates such as sodium carbonate, potassium carbonate and the like; alkali metal hydrogencarbonates such as sodium hydrogencarbonate, potassium hydrogencarbonate and the like; alkali metal hydroxides such as sodium hydroxide, potassium hydroxide and the like; alkali metal phosphates such as sodium phosphate, potassium phosphate and the like; alkali metal hydrides such as sodium hydride, potassium hydride and the like; alkali metals such as potassium, sodium and the like; alkali metal amides such as sodium amide and the like; alkali metal alcoholate such as sodium methylate, sodium ethylate and the like can be exemplified.

As to the organic bases, for example, pyridine, trimethylamine, triethylamine, N-ethyldiisopropylamine, 2,4,6-collidine, dimethylaniline, dimethylaminopyridine, N-methylmorphorine, N,N-dimethyl-4-aminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like can be exemplified.

These basic compounds are used singly or by mixing two or more thereof.

The amount of compound (2) is generally about 0.1 to 5 molar quantities, preferably about 0.5 to 3 molar quantities per 1 mole of compound (11). The amount of the basic compound is generally 1 to 10 molar quantities, preferably 1 to 5 molar quantities per 1 mole of compound (11).

The reaction of compound (2) with compound (11) is carried out generally at about 0 to 150° C., preferably at about 0 to 100° C., and generally the reaction is finished in about 1 to 100 hours.

In the above-mentioned reaction, a halide compound such as cesium fluoride may added in the reaction system.

More specifically, 1-substituted-4-nitroimidazole compound represented by the general formula (10a) is prepared by the reaction of compound (2) with compound (11a) as shown in the following reaction scheme, and 1-substituted-4-nitroimidazole compound represented by the general formula (10b) is prepared by the reaction of compound (2) with compound (11b) as shown in the following reaction schemes.

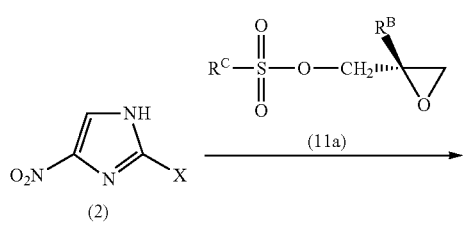

-continued

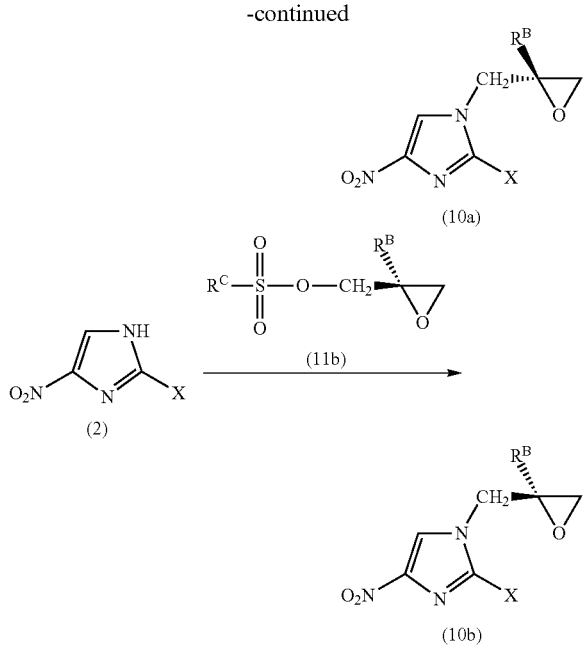

In the above-mentioned reaction, compound (2) to be used as the starting material is prepared, for example, by the above-mentioned Reaction scheme-2, Reaction scheme-3 or Reaction scheme-8 mentioned below.

On the other hand, compound (11) [compound (11a) or compound (11b)] to be used as another starting material is prepared from well-known compound (12) by the following Reaction scheme-5.

Reaction scheme-5

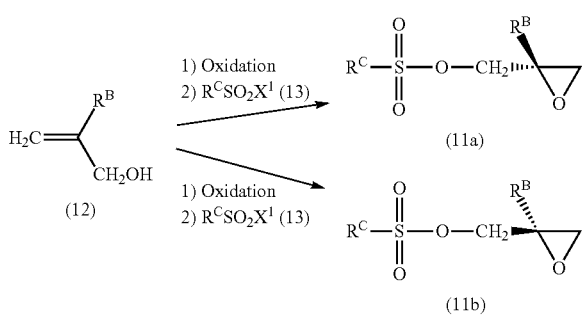

[wherein, $R^B$, $R^c$ and $X^1$ are the same as defined previously].

Compound (11a) is prepared by oxidizing compound (12), and the thus obtained oxidized compound is reacted with compound (13).

Oxidation of compound (12) is carried out in a suitable solvent, in the presence of a dextrorotary optically active compound by using as an oxidizing agent.

As to the oxidizing agent to be used in the reaction, well-known peroxides can be used widely, for example, cumene hydroperoxide, tert-butyl peroxide and the like can be exemplified.

As to the solvents, for example, alcohols such as methanol, ethanol, isopropanol and the like; aromatic hydrocarbons such as benzene, toluene, xylene and the like; halogenated hydrocarbons such as dichloromethane, dichloroethane, chloroform, carbon tetrachloride and the like; ethers such as diethyl ether, dioxane, tetrahydrofuran, diglyme, dimethoxyethane and the like; saturated hydrocarbons such as n-hexane, n-butane, cyclohexane and the like; ketones such as acetone, methyl ethyl ketone and the like; polar solvents such as N,N-dimethylformamide, N,N-dimethylacetamide, 1-methyl-2-pyrrolidinone (NMP), dimethyl sulfoxide, hexamethylphosphorous triamide, acetonitrile and the like; and mixtures of these solvents can be exemplified.

As to the dextrorotary optically active compounds, for example, dextrorotary optically active acids or their alkyl esters, such as diisopropyl (D)-(-)-tartrate, (D)-(-)-tartaric acid, (D)-(-)-di-p-toluoyltartaric acid, (D)-(-)-malic acid, (D)-(-)-mandelic acid, (D)-(-)-camphor-10-sulfonic acid and the like can be exemplified.

The amount of the oxidizing agent is generally at least an equimolar quantity, preferably about 1 to 3 molar quantity per 1 mole of compound (12).

The amount of the dextrorotary optically active compound is generally about 0.01 to 1 molar quantity, preferably about 0.01 to 0.5 molar quantity per 1 mole of compound (12).

The oxidation of compound (12) is generally carried out at about -50° C. to a room temperature, preferably at about -30° C. to a room temperature, and is finished in about 1 to 30 hours.

In conducting the oxidation of compound (12), an agent for accelerating reaction may preferably be added to the reaction system. As to the agent for accelerating reaction, for example, alkoxy titanium such as titanium tetraisopropoxide and the like; molecular sieves such as molecular sieves 5A, molecular sieves 4A, molecular sieves 3A and the like can be exemplified. These agents are used singly or by mixing two or more of these agents. The amount of the alkoxy titanium is generally about 0.01 to 1 molar quantity, preferably 0.01 to 0.5 molar quantity per 1 mole of compound (12). The amount of the molecular sieves is generally about 0.1 to 1 part by weight against 1 part by weight of compound (12).

The reaction of compound [compound (14a)] obtained by the above-mentioned oxidation with compound (13) is carried out in a suitable solvent, in the presence of a basic compound.

As to the solvent to be used in this oxidation, any one of the solvents used in the oxidation of compound (12) can be used.

As to the basic compounds, well-known inorganic bases and organic bases can be used.

As to the inorganic bases, for example, alkali metal carbonates such as sodium carbonate, potassium carbonate and the like; alkali metal hydrogencarbonates such as sodium hydrogencarbonate, potassium hydrogencarbonate and the like; alkali metal hydroxides such as sodium hydroxide, potassium hydroxide and the like; alkali metal phosphates such as sodium phosphate, potassium phosphate and the like; alkali metal hydrides such as sodium hydride, potassium hydride and the like; alkali metals such as potassium, sodium and the like; alkali metal amides such as sodium amide and the like; alkali metal alcoholates such as sodium methylate, sodium ethylate, and the like can be exemplified.

As to the organic bases, for example, pyridine, trimethylamine, triethylamine, N-ethyldiisopropylamine, 2,4,6-collidine, dimethylaniline, dimethylaminopyridine, N-methylmorpholine, N,N-dimethyl-4-aminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like can be exemplified.

These basic compounds are used singly or by mixing two or more of these.

The amount of compound (13) is generally about at least 1 mole, preferably about 1 to 2 moles per 1 mole of compound (12).

The amount of the basic compound is generally about at least 1 mole, preferably 1 to 2 moles per 1 mole of compound (12).

The reaction of compound (14a) with compound (13) is carried out, generally at −50° C. to about a room temperature, preferably at −30° C. to about a room temperature, and is finished generally in 1 to 20 hours.

In the present invention, the desired compound (11a) can be prepared in that, after the oxidation of the compound (12), the reaction mixture is reacted with compound (13) without being separated the obtained compound (14a) from the reaction system. From view points of the workability and efficiency of the reaction, it is preferable to react compound (13) with the reaction mixture after the oxidation of the compound (12), since the solvents used in these series of reactions are the same.

Compound (11b) is prepared, at first by oxidizing compound (12), next the compound obtained by oxidation is reacted with compound (13).

Oxidation of compound (12) is carried out under the reaction condition similar to the oxidation of the above-mentioned compound (12), except that by using a levorotatory optically active compound in place of by using dextrorotatory optically active compound.

As to the levorotatory optically active compounds for example, levorotatory optically active acids or their alkyl esters, such as diisopropyl (L)-(+)-tartarate, (L)-(+)-tartaric acid, (L)-(+)-di-p-toluoyltartaric acid, (L)-(+)-malic acid, (L)-(+)-mandelic acid, (L)-(+)-camphor-10-sulfonic acid and the like can be exemplified.

Reaction of compound (14a), which is obtained from the above-mentioned oxidation, with compound (13) is carried out in a suitable solvent, in the presence of a basic compound.

Reaction of compound (14b) with compound (13) is carried out under the reaction condition similar to that of employed in the reaction of compound (14a) with compound (13).

In the present invention, the desired compound (11b) can be prepared in that, after the oxidation of the compound (12), the reaction mixture is reacted with compound (13) without being separated the obtained compound (14b) from the reaction system. From view points of the workability and efficiency of the reaction, it is preferable to react compound (13) with the reaction mixture after the oxidation of the compound (12), since the solvents used in these series of reactions are the same.

Compound (4) in the above-mentioned Reaction scheme-3 can also be prepared by the following Reaction scheme-6.

Reaction scheme-6

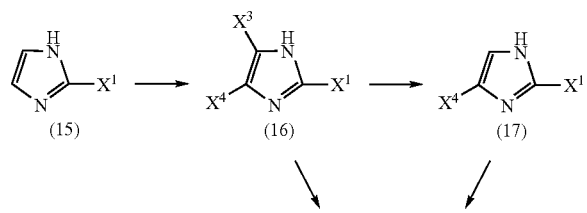

-continued

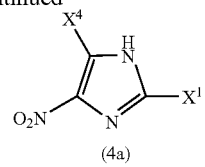

(4a)

[wherein, $X^1$ is the same as defined in the above; $X^3$ and $X^4$ are each shows a halogen atom].

Reaction of introducing compound (15) to compound (16) can be carried out under the condition similar to that employed in the reaction of obtaining compound (4) from compound (5) in Reaction scheme-3 mentioned previously.

Reaction of obtaining compound (17) from compound (16) can be carried out under the condition similar to that employed in the reaction of obtaining compound (1a) from compound (3) and the reaction of obtaining compound (4) from compound (2a) in Reaction scheme-3 mentioned previously.

Reaction of obtaining compound (4a) from compound (16) or compound (17) can be carried out under the condition similar to that employed in the nitration of an aromatic compound in general. For example, the reaction is carried out in a solvent or without solvent, in the presence of a nitrating agent. As to the solvent to be used in this nitration, fatty acids or anhydrides thereof such as acetic acid, acetic anhydride and the like; inorganic acids such as concentrated sulfuric acid and the like; halogenated hydrocarbons such as chloroform, dichloromethane, carbon tetrachloride and the like; and nitromethane and the like can be exemplified. As to the nitrating agents, for example, fuming nitric acid, concentrated nitric acid, mixed acid (a mixture of sulfuric acid, fuming sulfuric acid, phosphoric acid or acetic anhydride with nitric acid); a mixture of an alkali metal nitrate such as potassium nitrate, sodium nitrate and the like with sulfuric acid; alkyl ammonium nitrates such as tetra-n-butylammonium nitrate and the like; nitronium haloborate such as nitronium tetrafluoroborate and the like can be exemplified.

The amount of the nitrating agent may be at least an equimolar quantity, generally an excess amount of the agent is used per 1 mole of compound (16) or (17). In case of using alkylammonium nitrates or nitronium haloborates, at least an equimolar quantity, preferably an equimolar quantity to about 5 molar quantities may be used per 1 mole of compound (16) or (17). The said reaction is generally finished at −30° C. to about a room temperature, in about 10 minutes to 20 hours. In case of using an alkylammonium nitrate as the nitrating agent, at least an equimolar quantity, preferably an equimolar to 3 molar quantities of the fatty acid anhydride such as trifluoroacetic anhydride is used per 1 mole of compound (16) or (17) in the reaction system.

The starting material of compound (15) is a well-known compound, and can be also prepared by method of the following Reaction scheme-7.

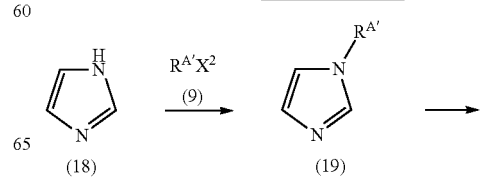

-continued

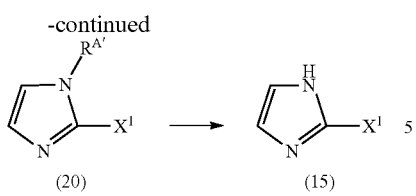

[wherein, $X^1$, $X^2$ and $R^{A'}$ are the same as defined previously].

Reaction of compound (18) with compound (9) can be carried out under the condition similar to that employed in the reaction of compound (4) with compound (9) in the above-mentioned Reaction scheme-3.

Reaction of obtaining compound (20) from compound (19) can be carried out under the condition similar to that employed in the reaction of obtaining compound (4) from compound (5) in the above-mentioned Reaction scheme-3.

Reaction of obtaining compound (15) from compound (20) can be carried out under the condition similar to that employed in the reaction of obtaining compound (2a) from compound (1a) in the above-mentioned Reaction scheme-3.

4-Nitroimidazole compound of the general formula (2) can also be prepared by the following Reaction scheme-8.

above-mentioned Reaction scheme-3. The amount of acrylonitrile may be at least an equimolar quantity, preferably an equimolar to about 15 molar quantities per 1 mole of compound (23). The said reaction is carried out generally at 0 to 150° C., preferably at about 0 to 100° C., and is finished generally in about 10 minutes to 5 hours.

Reaction of obtaining compound (25) from compound (24) and reaction of obtaining compound (26) from compound (23) can be carried out under the condition similar to that employed in the reaction of obtaining compound (4a) from compound (16) or (17) in the above-mentioned Reaction scheme-6.

In carrying out the reaction of obtaining compound (25) from compound (24), simultaneously compound (25aa), wherein the nitro group is substituted in the 5-position of the imidazole skelton, is obtained. The compound (2b) can be obtained from the compound (25aa) under the condition similar to that employed in the reaction of obtaining compound (2b) from compound (25).

Reaction scheme-8

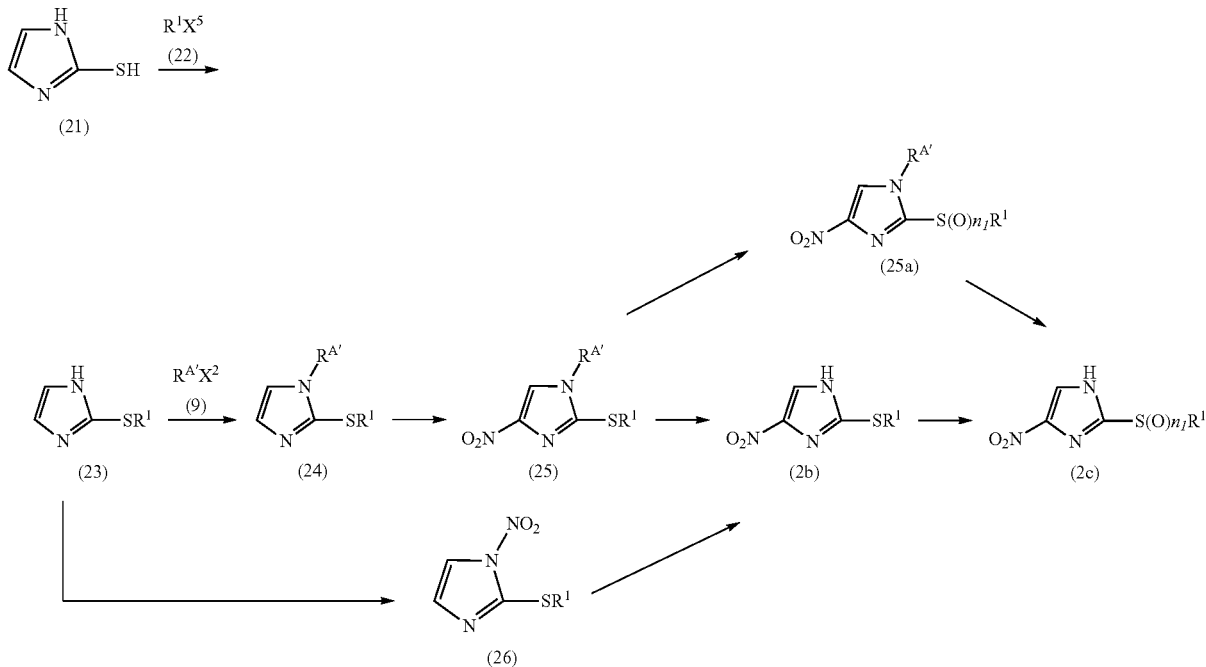

[wherein, $R^{A'}$, $R^1$ and $X^2$ are the same as defined in the above; $n_1$ shows 1 or 2: $X^5$ shows a halogen atom].

Reaction of compound (21) with compound (22) and reaction of compound (23) with compound (9) can be carried out under the condition similar to that employed in the reaction of compound (4) with compound (9) in the above-mentioned Reaction scheme-3. Further, compound (24) can be prepared by reacting compound (23) with acrylonitrile. This reaction can be carried out in a suitable solvent or without solvent, in the presence of a basic compound. The solvent and the basic compound used in this reaction are any one of those used in the reaction of compound (4) with compound (9) in the

(25aa)

Reaction of obtaining compound (2b) from compound (25) and reaction of obtaining compound (2c) from compound (25aa) can be carried out under the condition similar to that employed in the reaction of obtaining compound (2a) from compound (1a) in the above-mentioned Reaction scheme-3.

Reaction of obtaining compound (2b) from compound (26) can be carried out by heating in a suitable solvent. As to the solvent to be used in this reaction, aromatic hydrocarbons such as toluene, xylene, benzene, chlorobenzene and the like can be exemplified. The said reaction is generally carried out at a room temperature to 200° C., preferably at about a room temperature to 150° C., and reaction time is generally finished in about 10 minutes to 5 hours.

Reaction of obtaining compound (2c) from compound (2b) and reaction of obtaining compound (25a) from compound (25) are carried out in a suitable solvent, in the presence of an oxidizing agent. As to the solvent to be used in this reaction, for example, water; fatty acids such as formic acid, acetic acid, trifluoroacetic acid and the like; lower alcohols such as methanol, ethanol, isopropanol, n-butanol, tert-butanol, and the like; halogenated hydrocarbons such as chloroform, dichloromethane, carbon tetrachloride and the like; and mixtures of these solvent can be exemplified. As to the oxidizing agent to be used, for example, peracids such as performic acid, peracetic acid, pertrifluoroacetic acid, perbenzoic acid, m-chloroperbenzoic acid, o-carboxyperbenzoic acid and the like; hydrogen peroxide; sodium metaperiodate; bichromic acid; bichromates such as sodium bichromate, potassium bichromate and the like; permanganic acid; permanganates such as potassium permanganate, sodium permanganate and the like; lead salts such as lead tetracetate and the like can be exemplified. The oxidizing agent may be used generally at least an equimolar quantity, preferably an equimolar to 2 molar quantities per 1 mole of compound (2b) or compound (25). Further, in case of obtaining the compound having sulfonyl group (n is 2), the amount of oxidizing agent may be at least 2 molar quantities, preferably 2 to 4 molar quantities per 1 mole of compound (2b) or compound (25). The said reaction is carried out generally at about −10 to 40° C., preferably at −10° C. to about a room temperature, and is finished in about 1 to 30 hours.

1-Substituted-4-nitroimidazole derivative represented by the general formula (10) of the present invention can be prepared by the method shown in the following Reaction scheme-9.

Reaction scheme-9

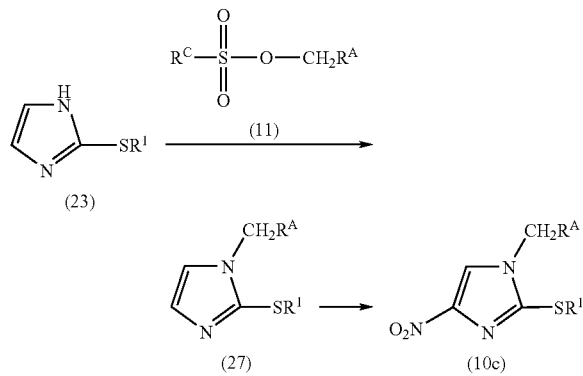

[wherein, $R^1$, $R^A$ and $R^C$ are the same as defined in the above].

Reaction of compound (23) with compound (11) can be carried out under the condition similar to that employed in the reaction of compound (2) with compound (11) in the above-mentioned Reaction scheme-4.

Reaction of obtaining compound (10c) from compound (27) can be carried out under the condition similar to that employed in the reaction of obtaining compound (4a) from compound (16) or (17) in the above-mentioned Reaction scheme-6.

Reaction scheme-10.

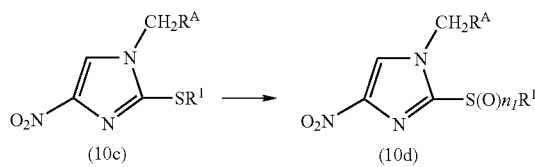

[wherein $R^A$, $R^1$ and $n^1$ are the same as defined in the above].

Reaction of obtaining compound (10d) from compound (10c) can be carried out under the condition similar to that employed in the reaction of obtaining compound (2c) from compound (2b) in the above-mentioned Reaction scheme-8.

Reaction scheme-11

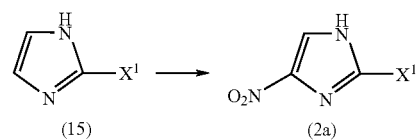

[wherein $X^1$ is the same as defined in the above].

Reaction of obtaining compound (2a) from compound (15) can be carried out in a suitable solvent or without solvent, in the presence of a nitronium haloborate, such as nitronium tetrafluoroborate as the nitrating agent.

As to the solvent, for example fatty acids or anhydride thereof, such as acetic acid, acetic anhydride and the like; inorganic acids, such as concentrated sulfuric acid; halogenated hydrocarbons, such as chloroform, dichloromethane, carbon tetrachloride and the like; nitromethane and the like can be exemplified. Among these solvent, nitromethane is used preferably. The amount of the nitrating agent may be at least an equimolar quantity, preferably an equimolar to 5 molar quantities per 1 mole of compound (15). The said reaction is carried out generally at −30° C. to about a room temperature, and is finished in about 10 minutes to 20 hours. The said reaction is known in a method of nitration by using the above-mentioned mixture of nitric acid-sulfuric acid. Under known nitration condition, compound (2a) can only be obtained in lower yield, and it is industrially disadvantageous. According to the present invention, by using a nitronium haloborate such as nitronium tetrafluoroborate as nitrating agent, the objective compound (2a) can be obtained in high yield and high purity.

The 1-substituted-4-nitroimidazole compounds (10a) and (10b) represented by the general formula (10) of the present invention can be introduced to compounds (30a) and (30b) which are useful compounds as antitubercular agents by the following Reaction scheme-12.

Reaction scheme-12

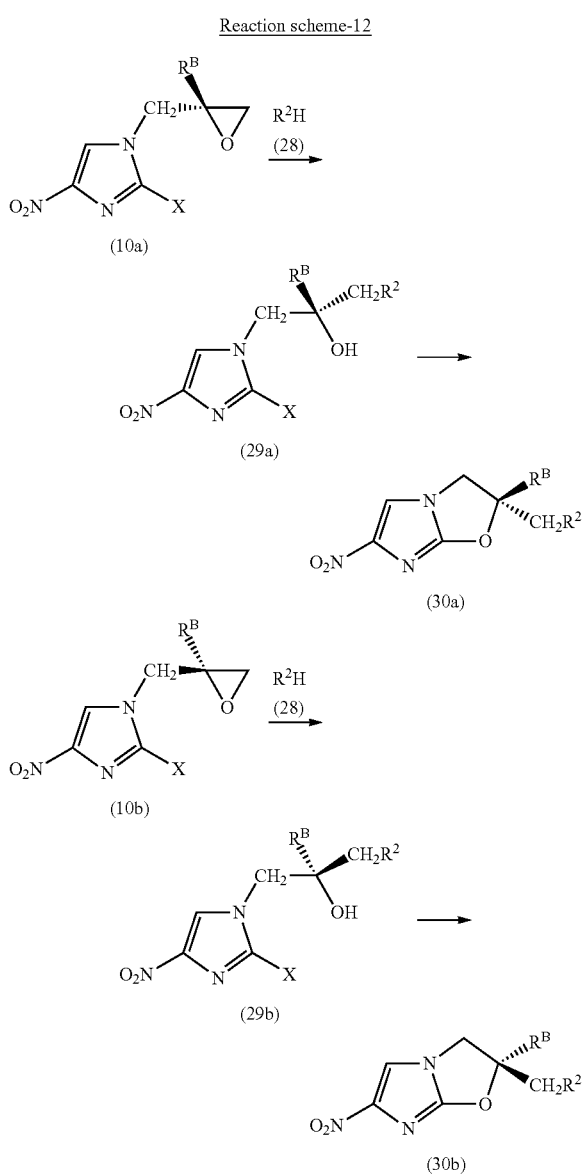

[wherein $R^B$ and X are the same as defined above, $R^2$ represents the following group of (A), (B), (C), (D), (E), (F) or (G) indicated below; and further, $R^B$ and —$(CH_2)_2R^2$ may bind to each other together with carbon atoms adjacent thereto through nitrogen atoms, so as to form a spiro ing represented by general formula (H) indicated below.]

General formulas (A) to (H) will be explained as follows:
a group represented by the following general formula (A):

—$OR^3$ (A)

wherein $R^3$ represents:
A1) hydrogen atom;
A2) C1-6 alkyl group;
A3) C1-6 alkoxy-C1-6 alkyl group
A4) phenyl C1-6 alkyl group (which may be substituted on the phenyl ring by at least one group selected from the group consisting of a phenyl C1-6 alkoxy group, a halogen-substituted or unsubstituted C1-6 alkyl group, a halogen-substituted or unsubstituted C1-6 alkoxy group, and a phenoxy group which may have, as a substituent, at least one halogen-substituted or unsubstituted C1-6 alkoxy group on the phenyl ring);

A5) biphenylyl C1-6 alkyl group;
A6) phenyl C2-6 alkenyl group:
A7) C1-6 alkylsulfonyl group;
A8) benzenesulfonyl group which may be substituted by a C1-6 alkyl group;
A9) C1-6 alkanoyl group;
A10) a group represented by the following general formula (Aa):

wherein $R^4$ represents a C1-6 alkoxycarbonyl group; phenyl C1-6 alkoxycarbonyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group); or phenyl C1-6 alkyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group);
A11) biphenylyl C1-6 alkoxycarbonyl group;
A12) benzoxazolyl C1-6 alkyl group (which may be substituted on the benzoxazole ring by at least one oxo group as a substituent);
A13) benzoxazolyl group; or
A14) oxazolyl C1-6 alkyl group (which may be substituted on the oxazole ring by at least one group selected from the group consisting of a phenyl group and C1-6 alkyl group as a substituent),
a group represented by the following general formula (B):

—$SR^5$ (B)

wherein $R^5$ represents a tetrazolyl group (which may be substituted on the tetrazole ring by a C1-6 alkyl group or phenyl group which may have a halogen atom as a substituent), or benzoxazolyl group,
a group represented by the following general formula (C):

—$COOR^6$ (C)

wherein $R^6$ represents a C1-6 alkyl group,
a carbamoyloxy group represented by the following general formula (D):

—$OOCNR^7R^8$ (D)

wherein $R^7$ and $R^8$ each identically or differently represent any one of:
D1) hydrogen atom;
D2) C1-8 alkyl group;
D3) halogen-substituted C1-6 alkyl group;
D4) C1-6 alkoxycarbonyl-C1-6 alkyl group;
D5) C3-8 cycloalkyl group;
D6) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
D7) phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, a C1-6 alkanoyl group, a carboxyl group, a C1-6 alkoxycarbonyl group, a phenyl C1-6 alkoxycarbonyl group, a carbamoyl group, a C1-6 alkylcarbamoyl group, an aminosulfonyl group, and a morpholino group);

D8) naphthyl group;
D9) pyridyl group; and
D10) $R^7$ and $R^8$ may bind to each other together with nitrogen atoms adjacent thereto directly or through other hetero atoms or carbon atoms, so as to form a saturated heterocyclic group shown in any one of (D10-1) to (D10-3) indicated below, or benzene condensed heterocyclic group shown in any one of (D10-4) to (D10-7) indicated below:

(D10-1) piperazinyl group represented by the following general formula (Da):

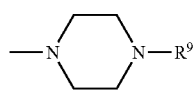

(Da)

wherein $R^9$ represents:
(Da1) hydrogen atom;
(Da2) C1-6 alkyl group;
(Da3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da4) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da5) C1-6 alkoxycarbonyl group;
(Da6) phenyl C1-6 alkoxycarbonyl group (which may be substituted on the phenyl ring by at least one group selected from the group consisting of a halogen atom, a halogen-substituted or unsubstituted C1-6 alkyl group and a halogen-substituted or unsubstituted C1-6 alkoxy group);
(Da7) phenyl C3-6 alkenyloxycarbonyl group (which may have at least one halogen-substituted or unsubstituted C1-6 alkyl group on the phenyl ring); or
(Da8) phenyl C1-6 alkylidene substituted amino group (which may be substituted on the phenyl ring by at least one halogen-substituted or unsubstituted C1-6 alkyl group as a substituent), (D10-2) a group represented by the following general formula (Db):

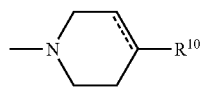

(Db)

wherein the dotted line represents that the bond may be a double bond, and $R^{10}$ represents:
(Db1) hydrogen atom;
(Db2) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Db3) phenoxy group (which may be substituted on the phenyl ring by at least one halogen-substituted or unsubstituted C1-6 alkyl group); or (Db4) phenylamino group (which may be substituted on the phenyl ring by at least one halogen-substituted or unsubstituted C1-6 alkyl group),
(D10-3) morpholino group;
(D10-4) indolinyl group (which may be substituted on the indoline ring by at least one halogen atom as a substituent);
(D10-5) isoindolinyl group (which may be substituted on the isoindoline ring by at least one halogen atom as a substituent);
(D10-6) 1,2,3,4-tetrahydroquinolyl group, (which may be substituted on the 1,2,3,4-tetrahydroquinoline ring by at least one halogen atom as a substituent); or
(D10-7) 1,2,3,4-tetrahydroisoquinolyl group, (which may be substituted on the 1,2,3,4-tetrahydroisoquinoline ring by at least one halogen atom as a substituent), a phenoxy group represented by the following general formula (E):

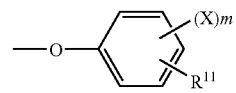

(E)

wherein X represents a halogen atom or amino substituted C1-6 alkyl group which may have a C1-6 alkyl group as a substituent, m represents an integer of 0 to 3, and $R^{11}$ represents:
E1) hydrogen atom;
E2) halogen-substituted or unsubstituted C1-6 alkyl group;
E3) halogen-substituted or unsubstituted C1-6 alkoxy group;
E4) a group represented by the following general formula (Ea):

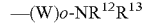

(Ea)

wherein W represents a group —CO— or a C1-6 alkylene group, o represents an integer of 0 or 1, and $R^{12}$ and $R^{13}$ each identically or differently represent any one of:
(Ea1) hydrogen atom;
(Ea2) C1-6 alkyl group;
(Ea3) C1-6 alkanoyl group;
(Ea4) C1-6 alkoxycarbonyl group;
(Ea5) phenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), and the alkyl portion may be substituted by a C1-6 alkoxyimino group);
(Ea6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ea7) benzoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);
(Ea8) pyridyl group (which may be substituted on the pyridine ring by at least one halogen atom as a substituent);

(Ea9) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Ea10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Ea11) benzoyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), E5) imidazolyl;
E6) triazolyl;
E7) morpholino group;
E8) thiomorpholino group;
E9) s-oxide thiomorpholino group;
E10) piperidyl group represented by the following general formula (Eaa):

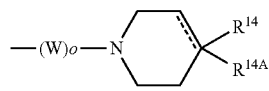

(Eaa)

wherein W and o are the same as above, $R^{14A}$ represents a hydrogen atom, hydroxyl group, C1-6 alkoxy group, or phenyl group (which may be substituted by halogen on the phenyl ring); the dotted line represents that the bond may be a double bond, and when the dotted line represents a double bond, it means that only $R^{14}$ is substituted; $R^{14}$ and $R^{14A}$ may bind to each other together with carbon atoms adjacent thereto to form a C1-4 alkylenedioxy group, and $R^{14}$ represents:

(Eaa1) hydrogen atom;
(Eaa2) C1-6 alkoxycarbonyl group;
(Eaa3) phenoxy group (which may be substituted on the phenyl ring by at least one group selected from the group consisting of a halogen atom; a halogen-substituted or unsubstituted C1-6 alkyl group; a halogen-substituted or unsubstituted C1-6 alkoxy group; a C1-4 alkylenedioxy group; a C1-6 alkoxycarbonyl group; a cyano group; a C2-6 alkenyl group; a nitro group; a phenyl group; an amino group which may have, as a substituent, a group selected from the group consisting of a phenyl group, a C1-6 alkyl group, a carbamoyl group and a C1-6 alkanoyl group; a C1-6 alkanoyl-substituted C1-6 alkyl group; a hydroxyl group; a C1-6 alkoxycarbonyl-substituted C1-6 alkyl group; a phenyl C1-6 alkyl group; a C1-6 alkanoyl group; a C1-6 alkylthio group; a 1,2,4-triazolyl group; an isoxazolyl group; an imidazolyl group; a benzothiazolyl group; a 2H-benzotriazolyl group; a pyrrolyl group; a benzoxazolyl group; a piperazinyl group (which may be substituted on the piperazine ring by at least one group selected from the group consisting of a C1-6 alkoxycarbonyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); a piperidinyl group (which may be substituted on the piperidine ring by at least one group selected from the group consisting of an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent)); and a carbamoyl group);

(Eaa4) hydroxyl group;
(Eaa5) carboxy group;
(Eaa6) phenyl group (which may be substituted on the phenyl ring by at least one group selected from the group consisting of a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), a halogen atom, a halogen-substituted or unsubstituted C1-6 alkyl group, and a halogen-substituted or unsubstituted C1-6 alkoxy group as a substituent);

(Eaa7) C1-6 alkoxy group;
(Eaa8) C3-8 cycloalkyl-C1-6 alkoxy group;
(Eaa9) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eaa10) tetrahydropyranyloxy group;
(Eaa11) 1,3-dioxolanyl group;
(Eaa12) oxo group;
(Eaa13) naphthyloxy group (which may be substituted on the naphthalene ring by at least one C1-6 alkyl group as a substituent);
(Eaa14) 2,3-dihydrobenzofuryloxy group (which may be substituted on the 2,3-dihydrobenzofuran ring by at least one group selected from the group consisting of a C1-6 alkyl group and an oxo group);
(Eaa15) benzothiazolyloxy group (which may be substituted on the benzothiazole ring by at least one C1-6 alkyl group);
(Eaa16) 1,2,3,4-tetrahydronaphthyloxy group (which may be substituted on the 1,2,3,4-tetrahydronaphthalene ring by at least one oxo group as a substituent);
(Eaa17) 1,3-benzoxathiolanyloxy group (which may be substituted on the 1,3-benzoxathiolan ring by at least one oxo group as a substituent);
(Eaa18) isoquinolyloxy group;
(Eaa19) pyridyloxy group;
(Eaa20) quinolyloxy group (which may be substituted on the quinoline ring by at least one C1-6 alkyl group as a substituent);
(Eaa21) dibenzofuryloxy group;
(Eaa22) 2H-chromenyloxy group (which may be substituted on the 2H-chromen ring by at least one oxo group as a substituent);
(Eaa23) benzisoxazolyloxy group;
(Eaa24) quinoxalyloxy group;
(Eaa25) 2,3-dihydro-1H-indenyloxy group (which may be substituted on the 2,3-dihydro-1H-indene ring by at least one oxo group as a substituent);
(Eaa26) benzofurazanyloxy group; or
(Eaa27) phenyl C2-6 alkenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group), E11) a group represented by the following general formula (Eab):

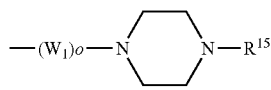
(Eab)

wherein o is the same as above, $W_1$ represents a C1-6 alkylene group and $R^{15}$ represents:

(Eab1) hydrogen atom;
(Eab2) C1-6 alkyl group (wherein the alkyl group may be substituted by a morpholino group, benzoyl group, carbamoyl group which may have a C1-6 alkyl group as a substituent, or cyano group);
(Eab3) C3-8 cycloalkyl group;
(Eab4) phenyl C1-6 alkyl group (which may be substituted on the phenyl ring by at least one group selected from the group consisting of a halogen atom, a cyano group, a phenyl group, a nitro group, a C1-6 alkylthio group, a C1-6 alkylsulfonyl group, a phenyl C1-6 alkoxy group, a C2-6 alkanoyloxy group, a halogen-substituted or unsubstituted C1-6 alkyl group, a halogen-substituted or unsubstituted C1-6 alkoxy group, and a 1,2,3-thiadiazolyl group);
(Eab5) C2-6 alkenyl group;
(Eab6) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);
(Eab7) C1-6 alkanoyl group;
(Eab8) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab9) benzoyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group);
(Eab10) C1-20 alkoxycarbonyl group (which may be substituted on the alkoxy group by at least one group selected from the group consisting of a halogen atom, an amino group which may have a C1-6 alkyl group as a substituent, and a C1-6 alkoxy-substituted C1-6 alkoxy group);
(Eab11) phenyl C1-6 alkoxycarbonyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, a nitro group, a halogen-substituted or unsubstituted C1-6 alkylthio group, an amino group which may have a C1-6 alkanoyl group, a phenyl C1-6 alkoxy group, a C1-6 alkoxycarbonyl group, and a 1,2,3-thiadiazolyl group);
(Eab12) a phenyl C3-6 alkenyloxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab13) phenoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab14) phenyl C1-6 alkylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab15) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab16) benzofuryl-substituted C1-6 alkoxycarbonyl group which may be substituted by at least one halogen atom on the benzofuran ring;
(Eab17) benzothienyl C1-6 alkoxycarbonyl group (which may be substituted on the benzothiophene ring by at least one group selected from the group consisting of a halogen atom and a halogen-substituted or unsubstituted C1-6 alkoxy group as a substituent);
(Eab18) naphthyl-substituted C1-6 alkoxycarbonyl group;
(Eab19) pyridyl-substituted C1-6 alkoxycarbonyl group (which may be substituted on the pyridine ring by at least one halogen atom as a substituent);
(Eab20) furyl-substituted C1-6 alkoxycarbonyl group (which may be substituted on the furan ring by at least one nitro group as a substituent);
(Eab21) thienyl-substituted C1-6 alkoxycarbonyl group (which may have at least one halogen atom as a substituent on the thiophene ring);
(Eab22) thiazolyl-substituted C1-6 alkoxycarbonyl group (which may be substituted on the thiazole ring by at least one group selected from the group consisting of a C1-6 alkyl group and a phenyl group (which may be substituted on the phenyl ring by at least one halogen-substituted or unsubstituted C1-6 alkyl group));
(Eab23) tetrazolyl-substituted C1-6 alkoxycarbonyl group (which may be substituted on the tetrazole ring by at least one group selected from the group consisting of a C1-6 alkyl group and a phenyl group (which may have at least one halogen atom as a substituent on the phenyl ring) as a substituent);
(Eab24) 2,3-dihydro-1H-indenyloxycarbonyl group;
(Eab25) adamantane-substituted C1-6 alkoxycarbonyl group;
(Eab26) phenyl C3-6 alkynyloxycarbonyl group;
(Eab27) phenylthio C1-6 alkoxycarbonyl group;
(Eab28) phenyl C1-6 alkoxy-substituted C1-6 alkoxycarbonyl group;
(Eab29) C2-6 alkenyloxycarbonyl group;
(Eab30) C2-6 alkynyloxycarbonyl group;
(Eab31) C3-8 cycloalkyl-substituted C1-6 alkoxycarbonyl group; or
(Eab32) benzoyl-substituted C1-6 alkoxycarbonyl group, E12) a group represented by the following general formula (Eb):

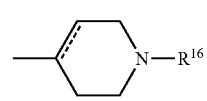
(Eb)

wherein the dotted line represents that the bond may be a double bond, and $R^{16}$ is defined as the same as $R^{15}$;

E13) a group represented by the following general formula (Ec):

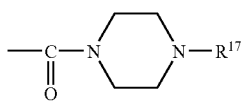

wherein R$^{17}$ represents:
(Ec1) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ec2) C1-6 alkoxycarbonyl group; or
(Ec3) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), E14) pyridyl group;

E15) a group represented by the following general formula (Ee):

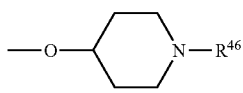

wherein R$^{46}$ represents a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or C1-6 alkoxycarbonyl group, E16) phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E17) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E18) 8-azabicyclo[3,2,1]octyl group (which may be substituted on the 8-azabicyclo[3,2,1]octane ring by at least one phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent);

E19) a group represented by the following general formula (Ef):

wherein R$^{47}$ and R$^{48}$ each identically or differently represent any one of a hydrogen atom, a C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), or a pyridyl group (which may be substituted on the pyridine ring by at least one halogen-substituted or unsubstituted C1-6 alkyl group as a substituent); and further, R$^{47}$ and R$^{48}$ may bind to each other together with nitrogen atoms adjacent thereto directly or through other hetero atoms, so as to form a 5-7 membered saturated heterocyclic ring, which may be substituted on the heterocyclic ring by at least one phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent;

E20) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E21) amino substituted C2-6 alkenyl group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); or E22) oxazolidinyl group (which may be substituted on the oxazolidine ring by at least one oxo group as a substituent),
a group represented by the following general formula (F):

$$NR^{19}R^{20} \qquad (F)$$

wherein R$^{19}$ and R$^{20}$ each identically or differently represent any one of:
F1) hydrogen atom;
F2) C1-6 alkyl group;
F3) phenyl C1-6 alkyl group (which may be substituted on the phenyl ring by at least one group selected from the group consisting of: a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a halogen atom; a halogen-substituted or unsubstituted C1-6 alkyl group; a halogen-substituted or unsubstituted C1-6 alkoxy group; an amino group which may have at least one group selected from the group consisting of a C1-6 alkyl group, and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a piperazinyl group (which may be substituted on the piperazine ring by at least one phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); and a piperidyl group (which may be substituted on the piperidine ring by at least one amino group which may have a group selected from the group consisting of a phenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group) and a C1-6 alkyl group as a substituent));

F4) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F5) amino C1-6 alkyl group (which may be substituted on the amino group by at least one group selected from the group consisting of a C1-6 alkyl group, a C1-6 alkoxycarbonyl group, and a phenyl group which may be substituted on the phenyl group by at least one group selected from a group consisting of a halogen atom and a halogen-substituted or unsubstituted C1-6 alkyl group);

F6) phenyl group (which may be substituted on the phenyl ring by at least one group selected from the group consisting of a halogen atom, a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), and a C1-6 alkoxycarbonyl group);

F7) C1-6 alkoxycarbonyl group;

F8) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F9) a group represented by the following general formula (Fa):

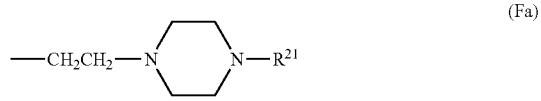

wherein $R^{21}$ represents a C1-6 alkoxycarbonyl group; phenyl C1-6 alkoxycarbonyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom and a halogen-substituted or unsubstituted C1-6 alkyl group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F10) 1-substituted-4-piperidyl group represented by the following formula (Fb):

wherein $R^{22}$ represents a C1-6 alkoxycarbonyl group; phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F11) piperidyl C1-6 alkyl group (which may have at least one phenoxy group (which may have at least one halogen-substituted or unsubstituted C1-6 alkyl group as a substituent) as a substituent);

F12) in addition, $R^{19}$ and $R^{20}$ may bind to each other together with nitrogen atoms adjacent thereto directly or through other hetero atoms or carbon atoms, so as to form a heterocyclic ring shown in any one of (F12-1) to (F12-10) indicated below:

(F12-1) a group represented by the following formula (Fc):

wherein the dotted line represents that the bond may be a double bond, and $R^{23}$ represents:

(Fc1) C1-6 alkyl group;

(Fc2) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc3) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group which may have, as a substituent, a group selected from the group consisting of a C1-6 alkyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a piperidyl group (which may have, on the piperidine ring, as a substituent, at least one amino group that may have a group selected from the group consisting of a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group));

(Fc4) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc5) biphenylyl C1-6 alkoxy group;

(Fc6) phenyl C3-6 alkenyloxy group which may be substituted on the phenyl ring by at least one halogen atom;

(Fc7) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fc8) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc9) C1-6 alkoxycarbonyl group;

(Fc10) phenyl C1-6 alkoxycarbonyl group (which may be substituted on the phenyl ring by at least one halogen-substituted or unsubstituted C1-6 alkoxy group);

(Fc11) phenyl C1-6 alkylcarbamoyl group wherein at least one halogen may be substituted on the phenyl ring;

(Fc12) phenylcarbamoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Fc13) phenylthio group (which may be substituted on the phenyl ring by at least one halogen-substituted or unsubstituted C1-6 alkoxy group);

(Fc14) phenyl sulfoxide (which may be substituted on the phenyl ring by at least one halogen-substituted or unsubstituted C1-6 alkoxy group);

(Fc15) pyridyl C1-6 alkoxy group; or (Fc16) a group represented by the following general formula (Fca):

$$-(C=O)o\text{-}NR^{24}R^{25} \quad \text{(Fca)}$$

wherein o is the same as above, and each of $R^{24}$ and $R^{25}$ represents:

(Fca1) hydrogen atom;

(Fca2) C1-6 alkyl group;

(Fca3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fca5) C1-6 alkanoyl group;

(Fca6) phenyl C2-6 alkanoyl group that may be substituted on the phenyl ring by at least one halogen atom;

(Fca7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca8) C1-6 alkoxycarbonyl group;

(Fca9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca10) phenylcarbamoyl group (which may be substituted on the phenyl ring by at least one halogen-substituted or unsubstituted C1-6 alkyl group);

(Fca11) piperidyloxycarbonyl group (which may be substituted on the piperidine ring by at least one phenyl group (which may be substituted on the phenyl ring by at least one halogen-substituted or unsubstituted C1-6 alkyl group) as a substituent); or (Fca12) $R^{24}$ and $R^{25}$ may form a 5-6 membered saturated heterocyclic ring through nitrogen atoms adjacent thereto, which may be substituted on the heterocyclic ring by at least one group selected from the group consisting of a C1-6 alkoxycarbonyl group; a benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (F12-2) 4-substituted-1-piperazinyl group represented by the following general formula (Fd):

$$-N\diagdown\diagup N-R^{26} \quad \text{(Fd)}$$

wherein $R^{25}$ represents:

(Fd1) hydrogen atom;

(Fd2) C1-6 alkyl group;

(Fd3) C3-8 cycloalkyl group;

(Fd4) C3-8 cycloalkyl C1-6 alkyl group;

(Fd5) C1-6 alkoxycarbonyl C1-6 alkyl group;

(Fd6) phenyl C2-6 alkenyl group;

(Fd7) phenyl C1-6 alkyl group (which may be substituted on the phenyl ring by 1 to 3 groups selected from the group consisting of: a halogen atom; a cyano group; a halogen-substituted or unsubstituted C1-6 alkyl group; C3-8 cycloalkyl group; a halogen-substituted or unsubstituted C1-6 alkoxy group; an amino group which may have a C1-6 alkyl group as a substituent; a C1-6 alkoxycarbonyl group; a phenoxy group; a phenyl C1-6 alkyl group; a phenyl C2-6 alkenyl group; a pyridyl group; an imidazolyl group; and a piperidyl group);

(Fd8) biphenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd9) naphthyl C1-6 alkyl group;

(Fd10) phenyl group (which may be substituted on the phenyl ring by at least one group selected from the group consisting of: a halogen atom; a cyano group; an amino group which may have a C1-6 alkyl group as a substituent; a halogen-substituted or unsubstituted C1-6 alkyl group; a halogen-substituted or unsubstituted C1-6 alkoxy group; a C1-6 alkoxycarbonyl group; a carboxyl group; a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); an amino C1-6 alkyl group (which may have on the amino group at least one group selected from the group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group); and a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group));

(Fd11) biphenyl group (which may be substituted on the phenyl ring by at least one halogen-substituted or unsubstituted C1-6 alkyl groups);

(Fd12) amino group, amino group which is substituted by a C1-6 alkoxycarbonyl group, phenyl C1-6 alkylamino group (which may be substituted on the phenyl ring by at least one halogen-substituted or unsubstituted C1-6 alkyl group), or phenylamino group (which may be substituted on the phenyl ring by at least one group selected from the group consisting of a halogen-substituted or unsubstituted C1-6 alkyl group and a halogen atom);

(Fd13) benzoyl C1-6 alkyl group (which may have on the phenyl ring at least one halogen atom as a substituent);

(Fd14) phenylcarbamoyl C1-6 alkyl group (which may be substituted on the phenyl ring by at least one halogen-substituted or unsubstituted C1-6 alkyl group);

(Fd15) thiazolyl C1-6 alkyl group (which may be substituted on the thiazole ring by at least one group selected from the group consisting of a halogen-substituted or unsubstituted phenyl group and a C1-6 alkyl group);

(Fd16) oxazolyl C1-6 alkyl group (which may be substituted on the oxazole ring by at least one group selected from the group consisting of a halogen-substituted or unsubstituted phenyl group and a C1-6 alkyl group);

(Fd17) indolyl C1-6 alkyl group;

(Fd18) furyl C1-6 alkyl group (which may be substituted on the furan ring by at least one halogen-substituted or unsubstituted phenyl group);

(Fd19) imidazolyl C1-6 alkyl group (which may be substituted on the imidazole ring by a phenyl group);

(Fd20) quinolyl C1-6 alkyl group;

(Fd21) tetrazolyl group (which may be substituted on the tetrazole ring by a phenyl group);

(Fd22) pyrimidyl group which may be substituted by a phenyl group;

(Fd23) pyridyl group;

(Fd24) benzoxazolyl group;

(Fd25) benzothiazolyl group;

(Fd26) benzoxazolyl C1-6 alkyl group (which may have on the benzoxazole ring at least one oxo group as a substituent);

(Fd27) phenoxy C2-6 alkanoyl group which may be substituted on the phenyl ring by a halogen atom;

(Fd28) phenylthio C2-6 alkanoyl group which may be substituted on the phenyl ring by a halogen atom;

(Fd29) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fd30) benzoyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd31) biphenylylcarbonyl group;

(Fd32) pyridylcarbonyl group;

(Fd33) phenyl C2-6 alkenylcarbonyl group wherein a halogen atom may be substituted on the phenyl ring;

(Fd34) phenyl C1-6 alkylsulfonyl group wherein a halogen atom may be substituted on the phenyl ring;

(Fd35) benzenesulfonyl group (which may be substituted on the benzene ring by at least one group selected from the group consisting of a halogen atom and a C1-6 alkyl group);

(Fd36) a group represented by the following general formula (Fda):

$$-COOR^{27} \quad \text{(Fda)}$$

wherein $R^{27}$ represents:

(Fda1) halogen-substituted or unsubstituted C1-8 alkyl group;

(Fda2) C3-8 cycloalkyl group;

(Fda3) C3-8 cycloalkyl-C1-6 alkyl group;

(Fda4) C1-6 alkoxy-C1-6 alkyl group;

(Fda5) amino-C1-6 alkyl group which may have a C1-6 alkyl group;

(Fda6) a group represented by the following general formula (Fdb):

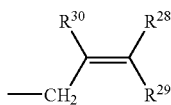

(Fdb)

wherein $R^{28}$, $R^{29}$, and $R^{30}$ represent a hydrogen atom, a C1-6 alkyl group, or a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), respectively;

(Fda7) phenyl C1-6 alkyl group (which may be substituted on the phenyl ring by 1 to 5 groups selected from the group consisting of: a halogen atom; a halogen-substituted or unsubstituted C1-6 alkyl group; a halogen-substituted or unsubstituted C1-6 alkoxy group; a halogen-substituted or unsubstituted C1-6 alkylthio group; a phenyl C1-6 alkoxy group; a hydroxy group; a C1-6 alkylsulfinyl group; a C1-6 alkylsulfonyl group; C1-6 alkylsulfonyloxy group; a cyano group; a C1-6 alkanoyl group; a benzoyl group; a phenyl C1-6 alkyl group which may have a C1-6 alkoxy group in the alkyl portion; an amino group; a nitro group; a carbamoyl group; a C1-6 alkanoylamino group; a C1-6 alkoxycarbonyl group; a C1-6 alkylaminocarbonyl group; a C1-6 alkoxycarbonylamino group; a tri-C1-6-alkylsiloxy group; a pyrrolyl group; a tetrahydropyranyloxy group; and an imidazolyl group);

(Fda8) biphenylyl C1-6 alkyl group;

(Fda9) benzhydryl group (which may be substituted on the benzene ring by at least one group selected from the group consisting of a halogen atom, a trifluoromethyl group, and a trifluoromethoxy group);

(Fda10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fda11) phenyl C2-6 alkynyl group (which may be substituted on the phenyl ring by at least one halogen-substituted or unsubstituted C1-6 alkyl group as a substituent);

(Fda12) pyridyl C1-6 alkyl group;

(Fda13) a group represented by the following general formula (Fdc):

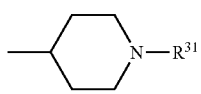

(Fdc)

wherein $R^{31}$ represents a phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (Fda14) piperidino C1-6 alkyl group (which may be substituted on the piperidine ring by a phenoxy group which may have at least one halogen-substituted or unsubstituted alkyl group as a substituent on the phenyl ring);

(Fda15) amino C1-6 alkyl group which may have, as a substituent, at least one group selected from the group consisting of a C1-6 alkyl group and a phenyl group which may have, as a substituent, a halogen-substituted or unsubstituted C1-6 alkoxy group on the phenyl ring;

(Fda16) 1,2,3,6-tetrahydropyridyl C1-6 alkyl group (which may be substituted on the 1,2,3,6-tetrahydropyridine ring by at least one phenyl group which may have, as a substituent, at least one halogen-substituted or unsubstituted C1-6 alkoxy group on the phenyl ring);

(Fda17) naphthyl C1-6 alkyl group;

(Fda18) fluorenyl C1-6 alkyl group;

(Fda19) pyridyl C1-6 alkyl group;

(Fda20) furyl C1-6 alkyl group (which may be substituted on the furan ring by a halogen-substituted or unsubstituted phenyl group);

(Fda21) thienyl C1-6 alkyl group;

(Fda22) oxazolyl C1-6 alkyl group (which may be substituted on the oxazole ring by a halogen atom or a halogen-substituted or unsubstituted phenyl group);

(Fda23) oxadiazolyl C1-6 alkyl group (which may be substituted on the oxadiazole ring by a halogen-substituted or unsubstituted phenyl group);

(Fda24) pyrazolyl C1-6 alkyl group (which may be substituted on the pyrazole ring by a halogen-substituted or unsubstituted phenyl group);

(Fda25) benzothienyl C1-6 alkyl group (which may be substituted on the benzothiophene ring by at least one group selected from the group consisting of a halogen atom and a halogen-substituted or unsubstituted C1-6 alkoxy group);

(Fda26) thienyl C1-6 alkyl group that may be substituted on the thiophene ring by a halogen atom;

(Fda27) benzothiazolyl C1-6 alkyl group;

(Fda28) benzofuryl C1-6 alkyl group which may be substituted on the benzofuran ring by a halogen atom;

(Fda29) indolinyl C1-6 alkyl group (which may be substituted on the indoline ring by at least one group selected from the group consisting of a C1-6 alkyl group and an oxo group);

(Fda30) benzoxazolyl C1-6 alkyl group (which may be substituted on the benzoxazole ring by at least one group selected from a group consisting of a halogen atom, a C1-6 alkyl group, and an oxo group);

(Fda31) chromenyl C1-6 alkyl group;

(Fda32) 1,2,3,4-tetrahydroquinolyl C1-6 alkyl group (which may be substituted on the quinoline ring by at least one group selected from the group consisting of a C1-6 alkyl group and an oxo group);

(Fda33) thiazolyl C1-6 alkyl group (which may be substituted on the thiazole ring by at least one group selected from the group consisting of a halogen atom, a halogen-substituted or unsubstituted phenyl group, and a C1-6 alkyl group); or (Fda34) tetrazolyl C1-6 alkyl group (which may be substituted on the tetrazole ring by a group selected from the group consisting of a halogen-substituted or unsubstituted phenyl group and a C1-6 alkyl group);

(Fd37) a group represented by the following general formula (Fe):

$$-Z-NR^{32}R^{33} \qquad (Fe)$$

wherein Z represents —C=O or —C=S, and $R^{32}$ and $R^{33}$ each identically or differently represent any one of:

(Fe1) hydrogen atom;
(Fe2) C1-6 alkyl group;
(Fe3) C3-8 cycloalkyl group;
(Fe4) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fe5) phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fe6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or
(Fe7) $R^{32}$ and $R^{33}$ may bind to each other together with nitrogen atoms adjacent thereto through other carbon atoms, so as to form a piperidine ring or 1,2,3,6-tetrahydropyridine ring, which may be substituted on the piperidine or 1,2,3,6-tetrahydropyridine ring by a phenyl group, which may be substituted at least one group selected from the group consisting of a halogen atom and a halogen-substituted or unsubstituted C1-6 alkyl group, (Fd38) a group represented by the following general formula (Ff):

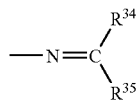

(Ff)

wherein $R^{34}$ represents a hydrogen atom or C1-6 lower alkyl group, and $R^{35}$ represents:

(Ff1) C3-8 cycloalkyl group;
(Ff2) C3-8 cycloalkenyl group;
(Ff3) a group represented by the following general formula (Ffa):

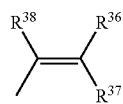

(Ffa)

wherein each of $R^{36}$, $R^{37}$, and $R^{38}$ represents: a hydrogen atom; C1-6 alkyl group; phenyl group (which may be substituted on the phenyl ring by at least one 1 to 5 groups selected from the group consisting of a halogen atom, a halogen-substituted or unsubstituted C1-6 alkyl group, a halogen-substituted or unsubstituted C1-6 alkoxy group, a C1-4 alkylenedioxy group, a C1-6 alkylsulfonyl group, a halogen-substituted or unsubstituted C1-6 alkylthio group, a nitro group, and an amino group which may have a C1-6 alkanoyl group as a substituent); benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group); biphenylyl group; furyl group (which may be substituted on the furan ring by a phenyl group which may have a halogen atom as a substituent); or thiazolyl group (which may be substituted on the thiazole ring by at least one phenyl group which may have a halogen atom as a substituent), (Ff4) phenyl group (which may be substituted on the phenyl ring by at least one group selected from the group consisting of: a halogen atom; a halogen-substituted or unsubstituted C1-6 alkyl group; a C3-8 cycloalkyl group; a hydroxyl group; a halogen-substituted or unsubstituted C1-8 alkoxy group; a C3-8 cycloalkoxy group; a C1-4 alkylenedioxy group; a cyano group; a nitro group; a phenyl C2-6 alkenyl group; a C2-6 alkanoyloxy group; an amino group which may have a C1-6 alkanoyl group as a substituent; a C1-6 alkylsulfonylamino group; a phenyl C1-6 alkoxy group; a phenoxy group; an amino group which has at least one C1-6 alkyl group as a substituent; an amino group which has at least one phenyl group as a substituent; an amino C1-6 alkoxy group which may have at least one C1-6 alkyl group as a substituent; a C1-6 alkoxycarbonyl group; a C1-6 alkoxycarbonyl C1-6 alkoxy group; a C1-6 alkylthio group; a pyrrolyl group; an imidazolyl group; a piperidyl group; a morpholino group; a pyrrolidinyl group; a thienyl group; a benzofuryl group; a piperazinyl group (which may be substituted on the piperazine ring by at least one group selected from the group consisting of a C1-6 alkyl group, a phenyl C1-6 alkyl group, and a benzoyl group which may have at least one C1-6 alkyl group as a substituent); a quinolyl group that may be substituted on the quinoline ring by at least one group selected from the group consisting of a C1-6 alkoxy group and an oxo group; a piperidylcarbonyl group which may be substituted on the piperidine ring by a carbostyril group; and a triazolyl group);

(Ff5) naphthyl group which may be substituted on the naphthalene ring by at least one group selected from the group consisting of a halogen atom, a halogen-substituted or unsubstituted C1-6 alkoxy group, and an amino group which may have a C1-6 alkyl group as a substituent;

(Ff6) biphenylyl group (which may be substituted on the biphenylyl ring by at least one group selected from the group consisting of a halogen atom, a halogen-substituted or unsubstituted C1-9 alkyl group, and a halogen-substituted or unsubstituted C1-6 alkoxy group);

(Ff7) fluorenyl group; pyrenyl group;

(Ff8) benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group);

(Ff9) benzothienyl group (which may be substituted on the benzothiophene ring by at least one group selected from the group consisting of a halogen atom, a halogen-substituted or unsubstituted C1-6 alkyl group, and a halogen-substituted or unsubstituted C1-6 alkoxy group);

(Ff10) pyridyl group (which may be substituted on the pyridine ring by at least one group selected from the group consisting of a halogen atom, a halogen-substituted or unsubstituted C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a furyl group, and a thienyl group);

(Ff11) furyl group (which may be substituted on the furan ring by 1 to 3 groups selected from the group consisting of a C1-6 alkyl group, a nitro group, and a phenyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a nitro group));

(Ff12) benzothiazole group (which may have, on the benzothiazole ring, at least one phenyl group that may have, as a substituent, a C1-6 alkoxy group on the phenyl ring);

(Ff13) thienyl group (which may have, on the thiophene ring, at least one group selected from the group consisting of a halogen atom, a nitro group, a C1-6 alkyl group, a pyrazolyl group which may be substituted on the pyrazole ring by at least one halogen-substituted or unsubstituted C1-6 alkyl group as a substituent, and a thienyl group which may have a halogen atom on the thiophene ring);

(Ff14) indolyl group (which may be substituted on the indole ring by at least one group selected from the group consisting of a phenylsulfonyl group which may have a C1-6 alkyl group as a substituent, a phenyl C1-6 alkyl group, a C1-6 alkoxycarbonyl group, and a phenyl group);

(Ff15) pyrrolyl group (which may be substituted on the pyrrole ring by at least one group selected from the group consisting of a phenyl group which may be substituted by at least one halogen-substituted or unsubstituted C1-6 alkyl group, and a C1-6 alkyl group);

(Ff16) coumaryl group;

(Ff17) benzimidazolyl group (which may be substituted on the benzimidazole ring by at least one thienyl group as a substituent);

(Ff18) oxazolyl group (which may be substituted on the oxazole ring by at least one phenyl group that may have a halogen atom as a substituent);

(Ff19) thiazolyl group (which may be substituted on the thiazole ring by at least one phenyl group, wherein at least one group selected from the group consisting of a halogen atom, a nitro group, and a phenyl group);

(Ff20) quinolyl group;

(Ff21) 3,4-dihydrocarbostyril group (which may be substituted on the 3,4-dihydrocarbostyril ring by at least one group selected from the group consisting of a C1-6 alkoxy group, a C1-6 alkyl group, and a phenyl C1-6 alkoxy group), or carbostyril group (which may be substituted on the carbostyril ring by at least one group selected from the group consisting of a C1-6 alkoxy group, a C1-6 alkyl group, and a phenyl C1-6 alkoxy group);

(Ff22) imidazo[2,1-b]thiazolyl group;

(Ff23) imidazo[2,1-a]pyridyl group;

(Ff24) chromanyl group (which may be substituted on the chroman ring by at least one C1-6 alkyl group); or (Ff25) 2,3-dihydrobenzofuryl group, or (Fd39) a group represented by the following general formula (Ffb):

wherein $R^{45}$ represents: a C1-6 alkoxycarbonyl group; phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); amino substituted C1-6 alkyl group which may have, on the amino group, a group selected from a group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group as a substituent; benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (F12-3) morpholino group;

(F12-4) imidazolyl group;

(F12-5) 1,4-dioxaazaspiro[4,5]decyl group (which may be substituted on the 1,4-dioxaazaspiro-[4,5]decane ring by at least one oxo group as a substituent);

(F12-6) homopiperazinyl group (which may be substituted on the homopiperazine ring by at least one group selected from the group consisting of a C1-6 alkoxycarbonyl group, a phenyl C1-6 alkoxycarbonyl group, and a phenyl-substituted or unsubstituted phenyl group as a substituent);

(F12-7) piperazinyl group (which may be substituted on the piperazine ring by at least one group selected from the group consisting of an oxo group, a C1-6 alkyl group, and a phenyl C1-6 alkyl group (which may be substituted on the phenyl ring by at least one halogen-substituted or unsubstituted C1-6 alkyl group));

(F12-8) piperidyl group (which may be substituted on the piperidine ring by at least one oxo group as a substituent);

(F12-9) pyrrolidinyl group (which may be substituted on the pyrrolidine ring by at least one phenoxy C1-6 alkyl group that may have a halogen-substituted or unsubstituted C1-6 alkoxy group as a substituent); and (F12-10) isoindolinyl group, F13) moreover, $R^{19}$ and $R^{20}$ may bind to each other together with nitrogen atoms adjacent thereto directly or through hetero atoms, so as to form a cyclic imide or amide shown in any one of (F13-1) to (F13-11) indicated below:

(F13-1) succinimide group;

(F13-2) oxazolidinyl group (which may be substituted on the oxazolidine ring by at least one oxo group as a substituent);

(F13-3) benzo-1,3-oxazolidinyl group (which may be substituted on the benzo-1,3-oxazolidine ring by at least one group selected from the group consisting of an oxo group, a halogen atom, and a phenyl group as a substituent);

(F13-4) imidazolidinyl group (which may be substituted on the imidazolidine ring by at least one group selected from the group consisting of an oxo group, a phenyl C1-6 alkyl group (which may be substituted on the phenyl ring by 1 to 3 groups selected from the group consisting of a halogen atom and a C1-6 alkoxy group), and a phenyl group);

(F13-5) benzimidazolidinyl group (which may be substituted on the benzimidazolidine ring by at least one group selected from the group consisting of: an oxo group; a halogen atom; a halogen-substituted or unsubstituted C1-6 alkyl group; an amino group which may have a C1-6 alkyl group as a substituent; a C1-6 alkoxycarbonyl group; and a piperidyl group (which may be substituted on the piperidine ring by at least one group selected from the group consisting of a C1-6 alkyl group, a phenyl group wherein 1 to 3 halogen atoms may be substituted on the phenyl ring, a C1-6 alkoxycarbonyl group, and a phenyl C1-6 alkoxycarbonyl group as a substituent));

(F13-6) phthalimide group;

(F13-7) indolinyl group (which may have on the indoline ring at least one group selected from the group consisting of a C1-6 alkyl group, a halogen atom, and an oxo group as a substituent);

(F13-8) 2,3-dihydrobenzothiazolyl group (which may have at least one oxo group on the 2,3-dihydrobenzothiazole ring);

(F13-9) 1H-2,4-benzoxazinyl group (which may be substituted on the 1H-2,4-benzoxazine ring by at least one oxo group as a substituent);

(F13-10) a group represented by the following general formula (Fga):

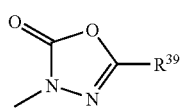

wherein $R^{39}$ represents: a hydrogen atom; a phenyl C1-6 alkyl group which may have, as a substituent, a halogen atom on the phenyl ring; phenoxy C1-6 alkyl group which may have, as a substituent, a halogen atom on the phenyl ring; phenyl C2-6 alkenyl group which may have, as a substituent, a halogen atom on the phenyl ring; phenyl group which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenyl group as a substituent; pyridyl group; or pyrazinyl group, and (F13-11) 1,3-thiazolidinyl group (which may be substituted on the 1,3-thiazolidine ring by at least one group selected from a group consisting of an oxo group and a phenyl C1-6 alkylidene group which may have a halogen-substituted or unsubstituted C1-6 alkyl group on the phenyl ring as a substituent), a group represented by the following general formula (G):

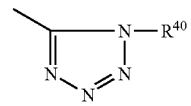

wherein $R^{40}$ represents a C1-6 alkyl group, or halogen-substituted or unsubstituted phenyl group, a spiro ring group represented by the following general formula (H):

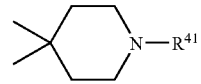

wherein $R^{41}$ represents:

H1) hydrogen atom;

H2) C1-6 alkyl group;

H3) phenyl C1-6 alkyl group that may have a phenyl group as a substituent on the phenyl ring;

H4) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); an phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and piperidyl group (which may be substituted on the piperidine ring by at least one group selected from the group consisting of phenoxy groups (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent));

H5) piperazinyl C1-6 alkyl group (which may be substituted on the piperazine ring by at least one group selected from the group consisting of a C1-6 alkoxycarbonyl group and a phenyl C1-6 alkoxycarbonyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, and a phenyl group);

H6) piperazinylcarbonyl C1-6 alkyl group (which may be substituted on the piperazine ring by at least one group selected from the group consisting of: a C1-6 alkoxycarbonyl group; a phenyl C1-6 alkoxycarbonyl group which may have, as a substituent, a halogen-substituted or unsubstituted C1-6 alkyl group on the phenyl ring; and a phenyl C1-6 alkyl group which may have, as a substituent, at least one group selected from the group consisting of a halogen-substituted or unsubstituted C1-6 alkyl group and a phenyl group on the phenyl ring);

H7) phenylcarbamoyl C1-6 alkyl group which may have at least one halogen-substituted or unsubstituted C1-6 alkyl group as a substituent on the phenyl ring;

H8) benzoxazolyl C1-6 alkyl group (which may have at least one oxo group as a substituent on the benzoxazole ring);

H9) benzothiazolyl group;

H10) tetrazolyl group (which may have at least one phenyl group as a substituent on the tetrazole ring);

H11) C1-6 alkylsulfonyl group;

H12) phenylsulfonyl group which may have at least one C1-6 alkyl group as a substituent on the phenyl ring;

H13) phenylthiocarbamoyl group which may be substituted on the phenyl ring by at least one halogen atom as a substituent;

H14) C1-8 alkoxycarbonyl group;

H15) phenyl C1-6 alkoxycarbonyl group (which may be substituted on the phenyl ring by at least one group selected from the group consisting of a halogen atom, a C1-6 alkoxycarbonyl group, an amino group which may have a C1-6 alkoxycarbonyl group as a substituent, a halogen-substituted or unsubstituted C1-6 alkyl group, a halogen-substituted or unsubstituted C1-6 alkoxy group, a nitro group, and a C1-6 alkylthio group);

H16) benzhydryloxycarbonyl group (which may be substituted on the phenyl ring by at least one halogen atom);

H17) C1-6 alkoxycarbonyl group which may have a phenyl-substituted or unsubstituted phenyl group;

H18) naphthyl C1-6 alkoxycarbonyl group;

H19) pyridyl C1-6 alkoxycarbonyl group;

H20) C1-6 alkoxy-substituted C1-6 alkoxycarbonyl group;

H21) piperazinyl C1-6 alkoxycarbonyl group (which may be substituted on the piperazine ring by at least one group selected from the group consisting of a C1-6 alkoxycarbonyl group and a phenyl C1-6 alkyl group (which may have at least one halogen atom as a substituent on the phenyl ring) as a substituent);

H22) phenoxycarbonyl group (which may be substituted on the phenyl ring by at least one group selected from the group consisting of a C1-6 alkyl group and a C1-6 alkoxy group);

H23) C1-6 alkanoyl group;

H24) benzoyl group (which may be substituted on the phenyl ring by at least one halogen-substituted or unsubstituted C1-6 alkyl group);

H25) phenyl C1-6 alkanoyl group (which may be substituted on the phenyl ring by at least one halogen-substituted or unsubstituted C1-6 alkyl group);

H26) phenoxy C1-6 alkanoyl group (wherein 1 to 3 halogen atoms may be substituted on the phenyl ring);

H27) piperazinyl C2-6 alkanoyl group (which may be substituted on the piperazine ring by at least one group selected from a group consisting of: a C1-6 alkanoyl group; a phenyl C1-6 alkyl group which may have, as a substituent, at least one group selected from the group consisting of a phenyl group, a halogen atom, a halogen-substituted or unsubstituted C1-6 alkyl group, and a halogen-substituted or unsubstituted C1-6 alkoxy group, on the phenyl ring; a phenyl C1-6 alkoxycarbonyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl C1-6 alkyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; and a benzoxazolyl group);

H28) phenylcarbamoyl group (which may be substituted on the phenyl ring by 1 to 3 groups selected from the group consisting of a halogen atom, an amino group which may have a C1-6 alkyl group as a substituent, a carboxyl group, a C1-6 alkoxycarbonyl group, a halogen-substituted or unsubstituted C1-6 alkyl group, a halogen-substituted or unsubstituted C1-6 alkoxy group, a piperazinyl group which may have a C1-6 alkyl group as a substituent on the piperazine ring, and a morpholino group);

H29) phenyl C1-6 alkylcarbamoyl group (which may be substituted on the phenyl ring by at least one group selected from the group consisting of a halogen-substituted or unsubstituted C1-6 alkyl group and a halogen-substituted or unsubstituted C1-6 alkoxy group); or H30) piperazinylcarbonyl group (which may be substituted on the piperazine ring by at least one group selected from the group consisting of a C1-6 alkoxycarbonyl group, a phenyl C1-6 alkoxycarbonyl group which may have at least one halogen-substituted or unsubstituted C1-6 alkyl group on the phenyl ring, and a phenyl C1-6 alkyl group which may have a halogen-substituted or unsubstituted C1-6 alkyl group on the phenyl ring), provided that, when $R^1$ represents a hydrogen atom and $R^2$ represents a group represented by the above general formula (A), then $R^3$ cannot be an isopropyl group; when $R^1$ represents a hydrogen atom, $R^2$ represents a group represented by the above general formula (E), and m is 0, then $R^{11}$ cannot be a hydrogen atom; and further, when $R^1$ represents a hydrogen atom and $R^2$ represents a group represented by the above general formula (F), then it is not possible that $R^{19}$ represents a hydrogen atom and $R^{20}$ represents a tert-butoxycarbonyl group.

Reaction of compound (10a) or (10b) with compound (28) is carried out in a suitable solvent or without solvent, the presence or absence of a basic compound.

As to the solvents to be used in this reaction, for example, water; alcohols, such as methanol, ethanol, isopropanol, n-butanol, tert-butanol and the like; aromatic hydrocarbons, such as benzene, toluene, xylene, tetraline, o-chlorobenzene, m-chlorobenzene, 2,3-dichlorobenzene and the like; halogenated hydrocarbons, such as dichloromethane, dichloroethane, chloroform, carbon tetrachloride and the like; ethers, such as diethyl ether, dioxane, tetrahydrofuran, diglyme, dipropyl ether, dimethoxyethane and the like; saturated hydrocarbons, such as n-butane, n-hexane, cyclohexane, liquid paraffin and the like; ketones, such as acetone, methyl ethyl ketone and the like; polar solvents, such as N,N-dimethylformamide, N,N-dimethylacetamide, dimethyl sulfoxide, hexamethylphosphorous triamide, acetonitrile, 1-methyl-2-pyrrolidinone (NMP) and the like; and mixtures of these solvents can be exemplified.

As to the basic compounds, well-known inorganic besic compounds and organic basic compounds can be widely used.

As to the inorganic basic compounds, for example, alkali metal carbonates, such as sodium carbonate, potassium carbonate and the like; alkali metal hydrogencarbonates, such as sodium hydrogencarbonate, potassium hydrogencarboante and the like; alkali metal hydroxide, such as sodium hydroxide, potassium hydroxide and the like; alkali metal phosphates, such as sodium phosphate, potassium phosphate and the like; alkali metal hydrides, such as sodium hydride, potassium hydride and the like: alkali metals, such as potassium, sodium and the like; alkali metal amides, such as sodium amide and the like; alkali metal alcoholates, such as sodium methylate, sodium ethylate, sodium tert-butoxide and the like can be exemplified.

As to the organic basic compounds, for example, acetates, such as sodium acetate, potassium acetate and the like; pyridine, trimethylamine, triethylamine, diisopropylethylamine, dimethylaniline, 1-methypyrrolidine, N-methylmorpholine, N,N-dimethyl-4-aminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like can be exemplified.

The amount of compound (28) is generally at least about 1 molar quantity, preferably about 1 to 5 molar quantities per 1 mole of compound (10a) or compound (10b).

The amount of the basic compound is generally about 0.1 to 1 molar quantity, preferably about 0.1 to 0.5 molar quantity per 1 mole of compound (10a) or compound (10b).

Reaction of compound (10a) or compound (10b) with compound (28) is carried out generally at a room temperature to 150° C., preferably about a room temperature to 120° C., and is finished generally in about 10 minutes to 24 hours.

Reaction of obtaining compound (30a) from compound (29a) and reaction of obtaining compound (30b) from compound (29b) are carried out in a suitable solvent or without solvent, in the presence of a basic compound.

As to the solvents and basic compound to be used herein, any solvents and basic compounds used in the above-mentioned reaction of compound (10a) or compound (10b) with compound (28) can be also used.

The amount of the basic compound is generally about at least 1 molar quantity, preferably 1 to 2 molar quantities per 1 mole of compound (29a) or compound (29b).

The said reaction is carried out generally at about 0 to 150° C., preferably at about 0 to 120° C., and is finished generally in about 10 minutes to 48 hours.

4-Nitroimidazole compound represented by the general formula (2) of the present invention can be also introduced to compound (38), being useful as antitubercular agent described in WO97/01562 (Japanese Patent Publication Hei 11-508270).

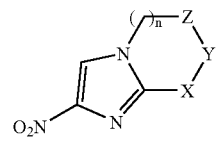

(38)

[wherein X is an oxygen atom, a sulfur atom or $NR_2$ (wherein $R_2$ is a hydrogen atom, a lower alkyl group, an aryl group, a cycloalkyl group, a heterocyclic group, a substituted heterocyclic group, a heterocyclic-alkyl group, $COR_3$, $SO_2R_4$ or $COR_4R_5$; wherein $R_3$, $R_4$ and $R_5$ are each independently selected from the group consisting of a hydrogen atom, a lower alkyl group, an aryl group, an alkylaryl group, an alkoxyaryl group, an alkoxyalkoxyaryl group, an alkyl-heterocyclic group, and an alkoxy-heterocyclic group); n is 1, 2 or 3; Y and Z are each independently selected from the group consisting of an oxygen atom, $CH_2$, CO, $CR_4R_5$ and $NR_4$ (wherein, $R_4$ and $R_5$, are the same as defined previously); provided that, when n is 2 or 3, then compound (38) may have some substituents as shown in the following general formulas (IIa) and (IIb),

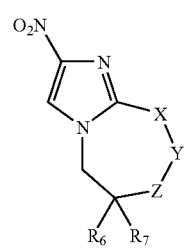

(IIa)

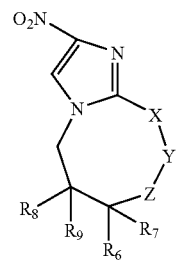

(IIb)

[wherein, $R_6$, $R_7$, $R_8$ and $R_9$ are each independently selected from the group consisting of a hydrogen atom, a lower alkyl group, an aryl group, an alkylaryl group, an alkoxyalkyl group, an alkoxyalkylaryl group, an alkoxyalkyl-heterocyclic group, an alkylarylalkylaryl group, an alkylarylaryl group, an alkylcycloalkyl group, an alkoxyaryl group, an alkyl-heterocyclic group and an alkoxy-heterocyclic group]. Compound (38) can be prepared, for example by the Reaction scheme-13 as follows.

Reaction Scheme-13
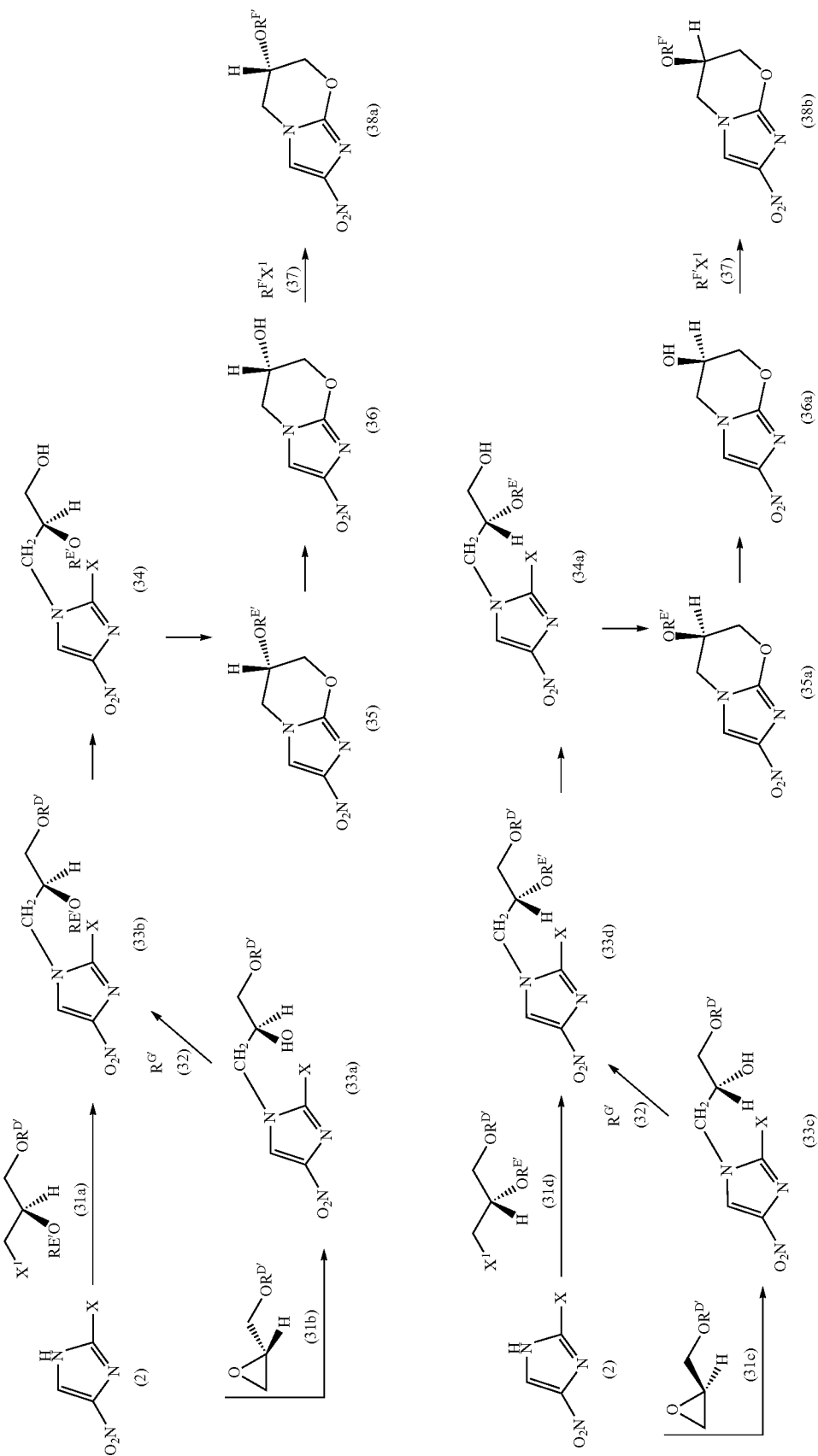

[wherein, X and X¹ are the same as defined previously; $R^{D'}$ and $R^{E'}$ are each, tetrahydropyranyl group, a tri(lower alkyl) silyl group, a lower alkanoyl group or a phenyl-lower alkyl group which may have lower alkoxy groups as the substituents in the phenyl ring; $R^{F'}$ is a substituted or unsubstituted arylalkyl group, an alkyl group, a substituted or unsubstituted arylalkoxyalkyl group, or a substituted or unsubstituted heterocyclic alkyl group; $R^{G'}$ is 3,4-dihydro-2H-pyran or $R^{I}X^{1}$ ($X^1$ is the same as defined previously and $R^I$ is a tri(lower alkyl)silyl group, a lower alkanoyl group or a phenyl-lower alkyl group which may have lower alkoxy groups as the substituents in the phenyl ring].

As to the tri(lower alkyl)silyl group, a silyl group having 3 substituents each of which is a straight chain or branched chain alkyl group having 1 to 6 carbon atoms, for example, tert-butyldimethylsilyl, trimethylsilyl, n-butylethylmethylsilyl, tert-butyldipropylsilyl, n-pentyldiethylsilyl, n-hexylpropylmethylsilyl groups and the like can be exemplified.

As to the lower alkanoyl group, a straight chain or branched chain alkanoyl group having 1 to 6 carbon atoms, for example, formyl, acetyl, propionyl, butyryl, isobutyryl, pentanoyl, tert-butylcarbonyl, hexanoyl groups and the like can be exemplified.

Reaction of compound (2) with compound (31a) and reaction of compound (2) with compound (31d) can be carried out under the condition similar to that employed in the reaction of compound of (4) with compound (9) in the above-mentioned Reaction scheme-3 wherein $X^2$ is a halogen atom.

Reaction for obtaining compound (34) from compound (33b) and reaction for obtaining compound (34a) from compound (33d) wherein $R^{D'}$ is a tri(lower alkyl)silyl group are carried out in a suitable solvent in the presence of a desilylating agent. As to the solvent to be used, any one of the solvent being used in the reaction for introducing compound (1a) to compound (2a) in the above-mentioned Reaction scheme-3 can be also used. As to the desilylating agent, an alkylammonium halide such as tetrabutylammonium fluoride can be exemplified. The amount of desilylating agent may be at least an equimolar quantity, preferably 1 to 2 molar quantities per 1 mole of compound (33b) or (33d). The said reaction is carried out at 0-100° C., preferably 0-70° C., and is finished in about 1 to 30 hours. When $R^{D'}$ is a tetrahydropyranyl group, a lower alkanoyl group or a phenyl-lower alkyl group which may have lower alkoxy group as the substituents in the phenyl group, the said reaction can be carried out under the condition similar to that employed in the reaction for obtaining compound (2a) from compound (1a) in the above-mentioned Reaction scheme-3.

Reaction of compound (2) with compound (31b) and reaction of compound (2) with compound (31c) can be carried out under the condition similar to that employed in the reaction of compound (4) with compound (9) in the above-mentioned Reaction scheme-3, wherein $X^2$ is a halogen atom.

Reaction of compound (33a) with compound (32), and reaction of compound (33c) with compound (32), can be carried out under the condition similar to that employed in the reaction of compound (40a) with compound (32) in the Reaction scheme-14 mentioned below.

Reaction for obtaining compound (35) from compound (34), reaction for obtaining compound (35a) from compound (34a), reaction for obtaining compound (36) from compound (35), reaction for obtaining compound (36a) from compound (35a), reaction of compound (36) with compound (37) and reaction of compound (36a) with compound (37) can be carried out by the method disclosed in the WO97/01562 (Japanese Patent Publication Hei 11-508270).

Among compounds (33a), (33b), (33c), (33d), (34) and (34a), those of 4-nitroimidazole derivatives wherein X is a bromine atom or a group of the formula —S(O)n$R^1$ (wherein $R^1$ and n are the same as defined previously) are novel compounds, useful for intermediates for synthesis of antitubercular agents.

The starting materials of compounds (31a) and (31d) can be prepared by Reaction scheme-14 as follows.

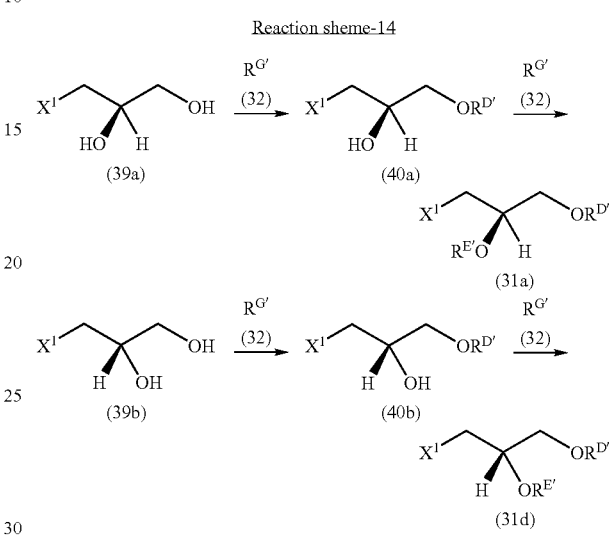

Reaction sheme-14

[wherein, $X^1$, $R^{D'}$, $R^{G'}$ and $R^{E'}$ are the same as defined previously].

Reaction of compound (39a) or compound (39b) with compound (32) and reaction of compound (40a) or compound (40b) with compound (32) can be carried out in a suitable solvent, when $R^{G'}$ is 3,4-dihydro-2H-pyran. As to the solvents to be used in this reaction, any one of solvents used in the reaction of compound (4) with compound (9) in the above-mentioned Reaction scheme-3 can be used, wherein $X^2$ is a halogen atom. The said reaction is generally carried out about at 0 to 100° C., preferably at 0 to 70° C., and is finished in about 1 to 30 hours. The said reaction is carried out advantageously by adding, as a catalyst, for example, a mineral acid, such as hydrochloric acid, sulfuric acid or the like; an organic acid, such as pyridinium p-toluenesulfonic acid or the like. When $R^{G'}$ is $R^{I}X^1$, the reaction can be carried out under the condition similar to that employed in the reaction of compound (4) with compound (9) in the above-mentioned Reaction scheme-3, wherein $X^2$ is a halogen atom.

In the reaction of compound (39a) or compound (39b) with compound (32) and reaction of compound (40a) or compound (40b) with compound (32), wherein $R^{G'}$ is $R^{I}X^1$ and $R^I$ is a tri(lower alkyl)silkyl group, compound (40a) and compound (40b) can be obtained by the reaction in the presence of imidazole in a suitable solvent. As to the solvent to be used, any one of the solvent being used in the reaction of compound (4) with compound (9) in the above-mentioned Reaction scheme-3, wherein $X^2$ is a halogen atom.

The amount of compound (32) is generally at least 1 molar quantity, preferably 1 to 2 molar quantities per 1 mole of compound (39a) or compound (39b), or compound (40a) or compound (40b). The amount of imidazole is generally at least about 1 molar quantity, preferably about 1 to 2 molar quantities per 1 mole of compound (39a) or compound (39b), or compound (40a) or compound (40b). The said reaction is carried out generally at about 0 to 100° C., preferably about 0 to 70° C., and is finished generally in about 1 to 30 hours.

Each of the objective compounds obtained from the above-mentioned reactions can be separated from the reaction mixture by usual separation means, and are subjected to further purifications. As to such means of separation and purification, for example, distillation method, recrystallization method, column chromatography, ion-exchange chromatography, gel chromatography, affinity chromatography, preparative thin layer chromatography, solvent extraction method and the like can be exemplified.

Among 1-substituted-4-nitroimidazole compounds represented by the general formula (1) of the present invention having the basic group can be easily form a salt with a usual pharmacologically acceptable acid. As to the acids, for example, inorganic acids, such as sulfuric acid, nitric acid, hydrochloric acid, phosphoric acid, hydrobromic acid and the like; organic acids, such as acetic acid, p-toluenesulfonic acid, methanesulfonic acid, ethanesulfonic acid, oxalic acid, maleic acid, fumaric acid, citric acid, succinic acid, malic acid, tartaric acid, malonic acid, lactic acid, benzoic acid and the like can be exemplified.

1-Substituted-4-nitroimidazole compounds represented by the general formula (1) of the present invention involve stereoisomers and optical isomers.

1-Substituted-4-nitroimidazole compounds represented by the general formula (1) of the present invention are used advantageously as intermediates for synthesizing antitubercular agents as shown in the above-mentioned Reaction scheme-12 and Reaction scheme-13.

1-Substituted-4-nitroimidazole compounds represented by the general formula (10) of the present invention are prepared by using compound (11) as the starting material. By using compound (11) [i.e., compound (11a) or compound (11b)], the reaction with 4-nitroimidazole compound (2) is selectively occurred at the specific position (b) indicated below, and as the result, compound (10) [compound (10a) or compound (10b)] of the present invention having high optical purity can be prepared in high yield by one process step.

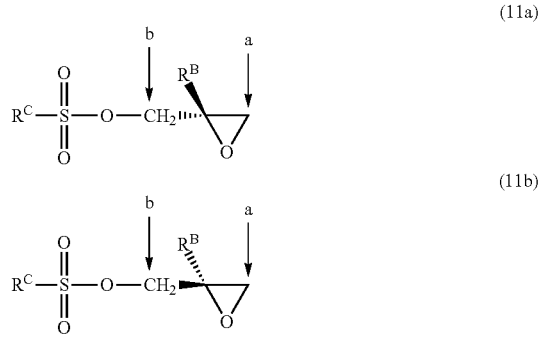

[wherein, $R^B$ and $R^C$ are the same as defined previously]

According to the present invention, the objective 4-nitroimidazole compound represented by the general formula (2a) can be prepared without by passing through intermediates having risk of explosion.

Preparation method of the present invention is a simple in operation and without requires complicated purification processes.

According to the present invention, high purity of the objective 4-nitroimidazole of the general formula (2a) can be prepared in low cost and high yield.

Therefore, the preparation methods of the present invention are industrially quite advantageous.

EXAMPLES

The present invention will be explained by illustrating some examples as follows.

Reference Example 1

Preparation of 2,5-dibromo-4-nitroimidazole

To a suspension of water (100 ml), 4-nitroimidazole (25 g) and sodium hydrogencarbonate (40.87 g), was dropwisely added bromine (26.5 ml) at lower than 10° C., the reaction mixture was stirred at 25 to 30° C. for 1 hour, and at 50 to 60° C. for 4 hours. Then concentrated hydrochloric acid was added to the reaction mixture at lower than 10° C. to adjust pH 1, the crystals separated were collected by filtration, and were washed thoroughly with water. The crystals were dried at 50° C. under a reduced pressure for 24 hours, there was obtained 51.01 g (85.2%) of 2,5-dibromo-4-nitroimidazole of pale yellow powdery product.

Reference Example 2

Preparation of 2,5-dibromo-1-methoxymethyl-4-nitroimidazole

Under an ice-cooling condition, sodium hydride (3.56 g) was added to a N,N-dimethylformamide (100 ml) solution of 2,5-dibromo-4-nitroimidazole (20.08 g). 10 minutes later, being added dropwise chloromethylmethyl ether (6.75 ml) thereto at 10 to 15° C., then the reaction mixture was turned back to a room temperature. After being stirred this reaction mixture for 5 hours, under an ice-cooling condition, sodium hydride (0.30 g) and chloromethylmethyl ether (0.56 ml) were added, further stirred at a room temperature for 1 hour. Then the reaction mixture was ice-cooled, water was added and extracted with ethyl acetate. The organic layer was washed with an aqueous solution being saturated with sodium chloride, dried over anhydrous sodium sulfate, then concentrated under a reduced pressure. Thus obtained crude crystals were washed with diisopropyl ether, and dried at 50° C. for 24 hours, there was obtained 2,5-dibromo-1-methoxymethyl-4-nitroimidazole (19.68 g, yield: 84.3%) as yellow powder product.

Reference Example 3

Preparation of (S)-2-methylglycidyl-4-nitrobenzenesulfonate

Under cooling at −10° C., to a toluene (830 ml) solution of β-methallyl alcohol (83.0 g), diisopropyl D-(−)-tartrate (16.19 g) and molecular sieves 4A (41.5 g) was added titanium tetraisopropoxide (17.0 ml), after being stirred the reaction mixture at −10° C. for 30 minutes, 80% of cumene hydroperoxide (415 ml) was added dropwise at −10° C. to −2° C. After being stirred the reaction mixture at 0° C. for 22 hours, excess of cumene hydroperoxide was reduced by adding dropwise trimethyl phosphite (141.1 ml) at −20° C. to −5° C. The end point of this reducing reaction was confirmed by use of zinc iodide starch paper.

Triethylamine (219 ml) was added to the reaction mixture, then toluene (830 ml) solution of 4-nitrobenzenesulfonyl chloride (332 g) was added dropwise at −30° C. to −16° C., and stirred at −10° C. for 1 hour. The reaction suspension was subjected to filtration with celite, and the filtrate was washed with an aqueous solution of 15% tartaric acid, an aqueous solution being saturated with sodium hydrogencarbonate, and an aqueous solution being saturated with sodium chloride in this order. After being dried the organic layer over anhydrous magnesium sulfate, and concentrated under a reduced pressure to obtain brown oil product (695 g). To the thus obtained brown oil was crystallized by adding diisopropyl ether (3,320 ml), the crystals were collected by filtration and purified by use of a silica gel column chromatography (eluent: dichloromethane), then recrystallized from diisopropyl ether/ethyl acetate (5/1) to obtain the desired compound (119.1 g, yield: 37.9%) as pale yellow crystals. Melting point: 71-72° C.

$^1$H-NMR (CDCl$_3$) δ (ppm): 1.38 (3H, s), 2.67 (1H, d, J=4.8 Hz), 2.72 (1H, d, J=4.5 Hz), 4.03 (1H, d, J=11.1 Hz), 4.27 (1H, d, J=11.1 Hz), 8.10-8.15 (2H, m), 8.39-8.44 (2H, m)

Optical purity: 96.6% e.e. (enantiomeric excess)

The optical purity was determined by a high performance liquid chromatography (HPLC) under the following conditions:
Column: CHIRALPAK AD (4.6 mmφ×250 mm)
[manufactured by Daicel Chemical Industries, Ltd.]
Moving bed: n-hexane/isopropanol=800/200
Flow velocity: 1.0 ml/minute
Detection wave length: 254 nm.

Reference Example 4

Preparation of (R)-2-methylglycidyl-4-nitrobenzenesulfonate

To a toluene (100 ml) solution of β-methallyl alcohol (10.0 g), diisopropyl L-(+)-tartrate (1.95 g), molecular sieves 3A (5.13 g) was added dropwise titanium tetraisopropoxide (2.0 ml) under cooling at −15° C., and was stirred at −10° C. for 30 minutes, then 80% cumene hydroperoxide (49.6 ml) was added dropwise at −10° C. to −2° C. After being stirred the reaction mixture at −5° C. for 18 hours, excessive cumene hydroperoxide was reduced by adding dropwise trimethyl phosphite (18.1 ml) at −10° C. to −2° C. The end point of this reducing reaction was confirmed by use of zinc iodide-starch paper.

To the reaction mixture was added a toluene (20 ml) solution of triethylamine (23.3 ml) and N,N-dimethyl-4-aminopyridine (1.02 g), then a toluene (80 ml) solution of 4-nitrobenzenesulfonyl chloride (35.15 g) was added dropwise at −10° C. to −2° C., and was stirred at −5° C. for 3 hours. The reaction suspension was subjected to filtration with celite, the filtrate was washed with an aqueous solution of 15% tartaric acid, an aqueous solution being saturated with sodium hydrogencarbonate, and an aqueous solution being saturated with sodium chloride in this order. After being dried the organic layer over anhydrous magnesium sulfate, and concentrated under a reduced pressure to obtain brown oil product (101.1 g).

To the thus obtained brown oil was crystallized by adding n-hexane (100 ml), the crystals were collected by filtration. The filtered crystals were recrystallized from diisopropyl ether/ethyl acetate (5/1) to obtain 18.6 g (48.9%) of the desired compound of pale yellow crystals. Melting point: 71-72° C.

$^1$H-NMR (CDCl$_3$) δ (ppm): 1.38 (3H, s), 2.67 (1H, d, J=4.8 Hz), 2.72 (1H, d, J=4.5 Hz), 4.03 (1H, d, J=11.1 Hz), 4.27 (1H, d, J=11.1 Hz), 8.10-8.15 (2H, m), 8.39-8.44 (2H, m).

Optical purity: 97.0% e.e.

The optical purity was determined by a high performance liquid chromatography (HPLC) under the following conditions:
Column: CHIRALPAK AD (4.6 mmφ×250 mm)
[manufactured by Daicel Chemical Industries, Ltd.]
Moving bed: n-hexane/isopropanol=800/200
Flow velocity: 1.0 ml/minute
Detection wave length: 254 nm.

Reference Example 5

Preparation of (R)-2-methylglycidyl-3-nitrobenzenesulfonate

To a toluene (200 ml) solution of β-methallyl alcohol (10.0 g), diisopropyl L-(+)-tartrate (3.89 g) and molecular sieves 4A (10.0 g) was added dropwise titanium tetraisopropoxide (4.07 ml) under cooling at −5° C., and was stirred at −5° C. for 30 minutes, then 80% cumene hydroperoxide (49.6 ml) was added dropwise at −13° C. to −10° C. After being stirred the reaction mixture at −10° C. for 3.5 hours, excessive cumene hydroperoxide was reduced by adding dropwise trimethyl phosphite (18.1 ml) at −15° C. to −5° C. The end point of this reducing reaction was confirmed by use of zinc iodide-starch paper.

To the reaction mixture was added a methylene chloride (10 ml) solution of N,N-dimethyl-4-aminopyridine (2.0 g) and triethylamine (23.2 ml), then a methylene chloride (50 ml) solution of 3-nitrobenzenesulfonyl chloride (33.9 g) was added dropwise at −15° C. to −5° C., and was stirred at −10° C. for 17 hours. The reaction suspension was subjected to filtration with celite, the filtrate was washed with an aqueous solution of 15% tartaric acid, an aqueous solution being saturated with sodium hydrogencarbonate, and an aqueous solution being saturated with sodium chloride in this order. After being dried the organic layer over anhydrous magnesium sulfate, and concentrated under a reduced pressure to obtain brown oil product (129.2 g).

To the thus obtained brawn oil product was purified by a silia gel column chromatography (eluent: n-hexane/ethyl acetate=3/1) to obtain (R)-2-methylglycidyl-3-nitrobenzenesulfonate of pale yellow oil (24.14 g, yield: 63.5%).

$^1$H-NMR (CDCl$_3$) δ (ppm): 1.38 (3H, s), 2.67 (1H, d, J=4.8 Hz), 2.73 (1H, d, J=4.8 Hz), 4.05 (1H, d, J=111.0 Hz), 4.28 (1H, d, J=111.0 Hz), 7.81 (1H, d, J=8.2, 7.8 Hz), 8.26 (1H, ddd, J=7.8, 1.8, 1.0 Hz), 8.53 (1H, ddd, J=8.2, 2.1, 1.0 Hz), 8.78 (1H, dd, J=2.1, 1.8 Hz).

Optical purity: 92.6% e.e.

The optical purity was determined by a high performance liquid chromatography (HPLC) under the following conditions:
Column: CHIRALPAK AD (4.6 mmφ×250 mm)
[manufactured by Daicel Chemical Industries, Ltd.]
Moving bed: n-hexane/isopropanol=850/150
Flow velocity: 1.0 ml/minute
Detection wave length: 254 nm.

Example 1

Synthesis of 2-bromo-1-methoxymethyl-4-nitroimidazole

Suspension of 2,5-dibromo-1-methoxymethyl-4-nitroimidazole (17.15 g), sodium sulfite (13.73 g), dimethylformamide (100 ml) and water (50 ml) was stirred at a room temperature for 8 hours. The reaction mixture was neutralized with an aqueous solution being saturated with sodium hydrogencarbonate, then ethyl acetate and water were added. The organic layer was washed with an aqueous solution being saturated with sodium chloride, and dried over anhydrous sodium sulfate, then concentrated under a reduced pressure to obtain 2-bromo-1-methoxymethyl-4-nitroimidazole (11.17 g, yield: 86.8%) of white powdery product.

EI (m/z) M$^+$: 235, 237

$^1$H-NMR (CDCl$_3$) δ (ppm): 7.93 (s, 1H), 5.34 (s, 2H), 3.41 (s, 3H).

Example 2

Synthesis of 2-bromo-4-nitroimidazole

Solution of 2-bromo-1-methoxymethyl-4-nitroimidazole (11.17 g), methanol (10 ml) and 5N hydrochloric acid (60 ml) was stirred under refluxing condition for 2.5 hours. After being let to stand the reaction mixture at a room temperature for 24 hours, the mixture was stirred for 1 hour under ice-cooling condition, the precipitated crystals were collected by filtration, and dried at 50° C. under a reduced pressure for 24 hours, there was obtained 2-bromo-4-nitroimidazole (6.0 g, yield: 66.0%) of white powdery product.

$^1$H-NMR (DMSO-d$_6$) δ (ppm): 8.42 (s, 1H), 14.10 (bs, 1H).

Example 3

Synthesis of 2-bromo-4-nitroimidazole

Into 1,4-dioxane (1 ml) solution of tetra-n-butylammonium borohydride (638 mg) was added dropwise 1,4-dioxane (1 ml) solution of 2,5-dibromo-4-nitroimidazole (89.5 mg) at a room temperature, after being refluxed the reaction mixture for 23 hours, excessive reagents were quenched by adding concentrated hydrochloric acid, then water and ethyl acetate were added. The organic layer was washed with an aqueous solution being saturated with sodium chloride, then dried over anhydrous sodium sulfate, and purified by a thin layer chromatography (developing agent: ethyl acetate) to obtain 2-bromo-4-nitroimidazole (44.9 g, yield: 71%) of white powdery product.

$^1$H-NMR (DMSO-d$_6$) δ (ppm): 8.42 (s, 1H), 14.10 (bs, 1H).

Example 4

Preparation of (S)-2-chloro-1-(2-methyl-2-oxiranyl-methyl)-4-nitroimidazole

To N,N-dimethylformamide (2.5 ml) solution of (R)-2-methylglycidyl-4-nitrobenzenesulfonate (0.5 g, 96.5% e.e.) were added 2-chloro-4-nitro-1H-imidazole (0.324 g) and potassium carbonate (0.330 g) at a room temperature. After being stirred the reaction mixture at 50° C. for 4 hours, the mixture was cooled to a room temperature, and was poured in water to cease the reaction. Extracted with ethyl acetate, and the extract was washed with water and an aqueous solution being saturated with sodium chloride in this order, then dried over anhydrous magnesium sulfate, and concentrated under a reduced pressure to obtain yellow solid product.

The thus obtained yellow solid product was purified by use of a silica gel column chromatography (eluent: n-hexane/ethyl acetate=7/3), there was obtained (S)-2-chloro-1-(2-methyl-2-oxiranylmethyl)-4-nitroimidazole (0.341 g, yield: 85.6%) as pale yellow crystals.

Melting point: 65.5-67.0° C.

$^1$H-NMR (CDCl$_3$) δ (ppm): 1.39 (3H, s), 2.62 (1H, d, J=3.6 Hz), 2.79 (1H, d, J=3.6 Hz), 3.99 (1H, d, J=14.7 Hz), 4.38 (1H, d, J=14.7 Hz), 7.87 (1H, s).

Optical purity: 95.4% e.e.

The optical purity was determined by use of high performance liquid chromatography (HPLC) under the following conditions.

Column: CHIRALPAK AD (4.6 mmφ×250 mm) [manufactured by Daicel Chemical Industries, Ltd.]
Moving bed: n-hexane/ethanol=850/150
Flow velocity: 1.0 ml/minute
Detection wave length: 254 nm.

Example 5

Preparation of (S)-2-chloro-1-(2-methyl-2-oxiranyl-methyl)-4-nitroimidazole

To N,N-dimethylformamide (2.5 ml) solution of (R)-2-methylglycidyl-3-nitrobenzenesulfonate (0.5 g, 92.6% e.e.) were added 2-chloro-4-nitroimidazole (0.270 g) and potassium carbonate (0.330 g) at a room temperature. After being stirred the reaction mixture at 50° C. for 3 hours, the mixture was cooled to a room temperature, and was poured in water to cease the reaction. Reaction mixture was extracted with ethyl acetate, and the extract was washed with water and an aqueous solution being saturated with sodium chloride in this order, then dried over anhydrous magnesium sulfate, and concentrated under a reduced pressure to obtain yellow solid product.

The thus obtained yellow solid was purified by use of a silica gel column chromatography (eluent: n-hexane/ethyl acetate=7/3), to obtain (S)-2-chloro-1-(2-methyl-2-oxiranyl-methyl)-4-nitroimidazole (0.307 g, yield: 77.0%) as pale yellow crystals.

Melting point: 65.5-67.0° C.

$^1$H-NMR (CDCl$_3$) δ (ppm): 1.39 (3H, s), 2.62 (1H, d, J=3.6 Hz), 2.79 (1H, d, J=3.6 Hz), 3.99 (1H, d, J=14.7 Hz), 4.38 (1H, d, J=14.7 Hz), 7.87 (1H, s).

Optical purity: 91.9% e.e.

The optical purity was determined by use of high performance liquid chromatography (HPLC) under the following conditions.

Column: CHIRALPAK AD (4.6 mmφ×250 mm) [manufactured by Daicel Chemical Industries, Ltd.]
Moving bed: n-hexane/ethanol=850/150
Flow velocity: 1.0 ml/minute
Detection wave length: 254 nm.

Example 6

Preparation of (R)-2-bromo-1-(2-methyl-2-oxiranyl-methyl)-4-nitroimidazole

Suspension of 2-bromo-4-nitroimidazole (100 g), 2-methyl-2-oxiranylmethyl(S)-4-nitrobenzenesulfonate (142.4 g), potassium carbonate (93.6 g), cesium fluoride (15.8 g) and dimethylformamide (420 ml) was stirred at 35-40° C. for 26 hours. The reaction mixture was poured into water (1.2 liters), then extracted twice with ethyl acetate (1 liter). The ethyl acetate layers were combined together, after being washed twice with water (1.2 liters), further washed with an aqueous solution (800 ml) being saturated with sodium chloride, then dried over anhydrous magnesium sulfate. After being filtrated under reduced pressure, the filtrate was concentrated under a reduced pressure. The thus obtained residue was purified by use of a silica gel column chromatography (eluent: n-hexane/ ethyl acetate=1/1), there was obtained (R)-2-bromo-1-(2-methyl-2-oxiranylmethyl)-4-nitroimidazole (110.9 g, yield: 81%) as yellow powdery product.

Melting point: 93.0-94.0° C.

$^1$H-NMR (CDCl$_3$) δ (ppm): 1.38 (3H, s), 2.61 (1H, d, J=4.0 Hz), 2.78 (1H, d, J=4.0 Hz), 4.00 (1H, d, J=14.9 Hz), 4.38 (1H, d, J=14.9 Hz), 7.92 (1H, s).

Optical purity: 96.6% e.e.

The optical purity was determined by use of high performance liquid chromatography (HPLC) under the following conditions.

Column: CHIRALPAK AD (4.6 mmφ×250 mm) [manufactured by Daicel Chemical Industries, Ltd.]
Moving bed: n-hexane/ethanol=4/1
Flow velocity: 1.0 ml/minute
Detection wave length: 254 nm.

Example 7

Preparation of (R)-2-chloro-1-(2-methyl-2-oxiranylmethyl)-4-nitroimidazole

To N,N-dimethylformamide (100 ml) solution of (S)-2-methylglycidyl-4-nitrobenzenesulfonate (50.0 g, 97.8% e.e.) was added 2-chloro-4-nitroimidazole (26.99 g) and potassium carbonate (27.82 g) at a room temperature. After being stirred this reaction mixture at 50° C. for 9 hours, the mixture was cooled to a room temperature, then ethyl acetate (150 ml) was added, after being removed the insoluble matters by filtration, the mixture was washed with water and an aqueous solution being saturated with sodium chloride in this order. Ethyl acetate layer was dried over anhydrous magnesium sulfate, then was concentrated under a reduced pressure to obtain pale brown solid product (38.2 g).

The thus obtained pale brown solid was dissolved in toluene (380 ml), next silica gel (7.6 g) was added, after being stirred at a room temperature, the silica gel was removed by filtration. This treatment was repeated twice, then the mother liquor was concentrated, the residue was crystallized by adding diisopropyl ether, there was obtained (R)-2-chloro-1-(2-methyloxiranylmethyl)-4-nitroimidazole (25.54 g, yield: 64.1%) as pale yellow crystals.

Melting point: 65.5-67.0° C.

$^1$H-NMR (CDCl$_3$) δ (ppm): 1.39 (3H, s), 2.62 (1H, d, J=3.6 Hz), 2.79 (1H, d, J=3.6 Hz), 3.99 (1H, d, J=14.7 Hz), 4.38 (1H, d, J=14.7 Hz), 7.87 (1H, s).

Optical purity: 95.9% e.e.

The optical purity was determined by use of a high performance liquid chromatography (HPLC) under the following conditions.

Column: CHIRALPAK AD (4.6 mmφ×250 mm) [manufactured by Daicel Chemical Industries, Ltd.]
Moving bed: n-hexane/ethanol=850/150
Flow velocity: 1.0 ml/minute
Detection wave length: 254 nm.

Reference Example 6

Preparation of (S)-1-(2-chloro-4-nitroimidazol-1-yl)-2-methyl-3-[4-(4-trifluoromethoxyphenyl)piperazin-1-yl]propan-2-ol Mixture of (R)-2-chloro-1-(2-methyl-2-oxiranylmethyl)-4-nitroimidazole (2.50 g, 11.5 mM) obtained in example 7 and 4-(4-trifluoromethoxyphenyl)piperazine (3.11 g, 12.6 mM) in N,N-dimethylformamide (25 ml) was stirred at 70° C. for 7 hours. The temperature of reaction mixture was turned back to a room temperature, water was added and extracted twice with ethyl acetate. The organic layers were combined, washed with water three times, dried on anhydrous magnesium sulfate and filtered. The filtrate was concentrated under a reduced pressure, there was obtained (S)-1-(2-chloro-4-nitroimidazol-1-yl)-2-methyl-3-[4-(4-trifluoromethoxyphenyl)piperazin-1-yl]propan-2-ol (5.55 g, yield: 100%) of slightly yellow oily product.

$^1$H-NMR (CDCl$_3$) δ (ppm): 1.18 (3H, s), 2.41 (1H, d, J=13.8 Hz), 2.56 (1H, d, J=13.8 Hz), 2.67-2.80 (2H, m) 2.85-2.96 (2H, m), 3.13-3.25 (4H, m), 4.03 (2H, s) 6.83-6.93 (2H, m), 7.07-7.17 (2H, m), 8.07 (1H, s).

Reference Example 7

Preparation of (S)-2-[4-(4-trifluoromethoxyphenyl) piperazin-1-ylmethyl]-2-methyl-6-nitro-2,3-dihydroimidazo[2,1-b]oxazole Under ice-cooling condition, to THF (150 ml) solution of (S)-1-(2-chloro-4-nitroimidazol-1-yl)-2-methyl-3-[4-(4-trifluoromethoxyphenyl)piperazin-1-yl]propan-2-ol (5.85 g, 12.61 mM) obtained in Reference example 6, was added sodium hydride (0.76 g, 18.92 mM), then the reaction mixture was heated and refluxed for 6 hours. The reaction mixture was concentrated under a reduced pressure, then subjected to ice-cooling, and water and ethyl acetate were added, the precipitated matters were collected by filtration, and purified by using a silica gel column chromatography (eluent: n-hexane/ethyl acetate=1/1), and recrystallized from isopropanol, there was obtained (S)-2-[4-(4-trifluoromethoxyphenyl)piperazin-1-ylmethyl]-2-methyl-6-nitro-2,3-dihydroimidazo[2,1-b]oxazole (2.58 g, yield: 48%) of slightly yellow solid.

Optical purity: 99.8% e.e.

$[α]_D^{26}$=8.800 (c: 1.000, CHCl$_3$)

Melting point: 129-130° C.

Test Example 1

Antibiotic Test by Using an Agar Plate Dilution Method

Minimum inhibitory concentration of (S)-2-[4-(4-trifluoromethoxyphenyl)piperazin-1-yl]methyl-2-methyl-6-nitro-2,3-dihydroimidazo[2,1-b]oxazole obtained in reference example 7 against strain of *Mycobacterium tuberculosis* H37RV was determined by using Culture medium 7H11 (manufactured by BBL Co.). The above-mentioned strain was cultivated previously in Culture medium 7H9 (manufactured by BBL Co.), the number of living bacteria of the strain was counted out, the culture medium was freeze-storaged at −80° C. was used, the final number of living bacteria was adjusted to about 10$^6$ CFU/ml. Thus prepared culture medium (5 μl) was inoculated on Culture medium 7H11 containing test compound, and cultivated at 37° C. for 14 days, the said cultivated medium was used to the test for determining the minimum inhibitory concentration.

The minimum inhibitory concentration of the test compound against *Mycobacterium tuberculosis* H37RV was 0.024 μg/ml.

Reference Example 8

Preparation of N-(Diethoxymethyl)imidazole

Mixture of imidazole (13.6 g), triethyl orthoformate (133 ml) and p-toluenesulfonic acid monohydrate (1.00 g) was stirred by heating at 140° C. for 2 hours. Reaction mixture was subjected to distillation under a reduced pressure, there was obtained N-(diethoxymethyl)imidazole (22.8 g, yield: 67.0%) as colorless oily product.

Boiling point: 106-108° C. (at 1 torr).

Reference Example 9

Preparation of 2-chloroimidazole

N-(Diethoxymethyl)imidazole (50.0 g) was dissolved in tetrahydrofuran (200 ml), to this solution was added dropwise n-hexane solution (120 ml) of 2.6M n-butyllithium at lower than −35° C., next tetrahyfrofuran solution (100 ml) of hexachloroethane (73.9 g) was added dropwise. Reaction mixture was allowed to stand at the same temperature for 5 minutes, then temperature was rised, after being added 6N hydrochloric acid (100 ml) at −20° C., then turned back to room temperature, and allowed to stand for 5 minutes. The aqueous layer was taken by separation, and the organic layer was extracted with 1N hydrochloric acid, the extract was combined with the former aqueous layer, and washed with diethyl ether, then neutralized with an aqueous solution of 6N sodium hydroxide, and extracted with ethyl acetate. The organic layer was taken by separation, after being dried over anhydrous magnesium sulfate, the solvent was removed by distillation to obtained a crude product. This crude product was triturated with methylene chloride, there was obtained 2-chloroimidazole (26.0 g, yield: 85.0%) as pale brown solid product.

$^1$H-NMR (CDCl$_3$) δ (ppm): 10.64 (1H, bs), 7.05 (1H, s).

Reference Example 10

Preparation of 2-chloro-4,5-diiodoimidazole

2-Chloroimidazole (5.13 g) was suspended in water (150 ml), and an aqueous solution of 6N sodium hydroxide (17 ml) was added. Next, iodine (25.9 g) was added and was stirred at a room temperature for 3 hours. After that, the reaction mixture was treated with an aqueous solution of sodium sulfite, the deposited matters were collected by filtration and dried, there was obtained 2-chloro-4,5-diiodoimidazole (16.4 g, yield: 92.5%) as yellow solid.

$^1$H-NMR (DMSO-d$_6$) δ (ppm): 13.61 (1H, bs)
$^{13}$C-NMR (DMSO-d$_6$) δ (ppm): 133.07.

Reference Example 11

Preparation of 2-chloro-4-iodoimidazole

2-Chloro-4,5-diiodoimidazole (7.09 g) and sodium sulfite (20.2 g) were dissolved in 30% ethanol (50 ml), the solution was heated and refluxed for 5 hours. Then the reaction mixture was concentrated, to the residue thus obtained was added water and the deposited matters were collected by filtration, and was triturated with diluted hydrochloric acid, there was obtained 2-chloro-4-iodoimidazole (885 mg, yield: 19.5%) as pale brown solid product.

$^1$H-NMR (DMSO-d$_6$) δ (ppm): 7.34 (1H, s)

Reference Example 12

Preparation of 2-chloro-5-iodo-4-nitroimidazole

2-Chloro-4,5-diiodoimidazole (354 mg) was suspended in concentrated nitric acid (d. 1.42)(5 ml), under ice-cooling, concentrated sulfuric acid (1 ml) was added, and was stirred at a room temperature for 15 hours. Reaction mixture was poured in ice-water, and ammonia water was added to adjust pH 3, the deposited matters were collected by filtration and dried, there was obtained 2-chloro-5-iodo-4-nitroimidazole (222 mg, yield: 81.2%) as yellow solid product.

EI (m/z) M$^+$=273.

Reference Example 13

Preparation of 2-chloro-5-iodo-4-nitroimidazole

2-Chloro-4-iodoimidazole (431 mg) was suspended in concentrated nitric acid (d. 1.38) (2.5 ml), under ice-cooling, concentrated sulfuric acid (2.5 ml) was added, and stirred at a room temperature for 6 hours. Then, the deposited matters were collected by filtration, and dried, there was obtained 2-chloro-5-iodo-4-nitroimidazole (348 mg, yield: 67.0%) as yellow solid product.

Reference Example 14

Preparation of 2-(4-nitrophenylthio)imidazole

Acetonitrile (100 ml) suspension of 2-mercaptoimidazole (5.0 g) and 4-chloronitrobenzene (8.7 g), potassium carbonate (8.3 g) was stirred under refluxing for 1 day. The reaction mixture was poured into ice-water. The deposited solid matters were collected by filtration, washed with water and diethyl ether. The thus obtained solids were dried, there was obtained 2-(4-nitrophenylthio)imidazole (9.5 g, yield: 86%) as yellow powdery product.

$^1$H-NMR (DMSO-d$_6$) δ (ppm): 7.22 (2H, d, J=9.0 Hz), 7.34 (2H, br.s), 8.14 (2H, d, J=9.0 Hz), 13.06 (1H, br.s).

Reference Example 15

Preparation of 2-(2-chloro-6-nitrophenylthio)imidazole

Acetonitrile (20 ml) suspension of 2-mercaptoimidazole (1.0 g) and 2,3-dichloronitrobenzene (2.1 g), potassium carbonate (1.7 g) was stirred under refluxing for 6.5 hours. The reaction mixture was poured into ice-water. The deposited solids were collected by filtration, and washed with n-hexane. The thus obtained solids were dried, there was obtained 2-(2-chloro-6-nitrophenylthio)imidazole (2.4 g, yield: 94%) as yellow powdery product.

$^1$H-NMR (DMSO-d$_6$) δ (ppm): 6.75-7.33 (1H, m), 7.64 (1H, t, J=8.0 Hz), 7.87 (1H, dd, J=1.0, 8.0 Hz), 7.97 (1H, dd, J=1.0, 8.0 Hz), 12.55 (1H, br.s).

Reference Example 16

Preparation of 1-nitro-2-(4-nitrophenylthio)imidazole

To chloroform (15 ml) suspension of 2-(4-nitrophenylthio) imidazole (1.0 g) and tetra-n-butylammonium nitrate (2.1 g) was added dropwise chloroform (5 ml) solution of anhydrous trifluoroacetic acid (1.3 ml) at −10° C., the reaction mixture was stirred at the same temperature for 25 minutes. Ice-water was added to the reaction mixture, after being stirred for a while, dichloromethane was added, and the dichloromethane layer was taken by separation, and washed with water, an aqueous solution being saturated with sodium hydrogencarbonate, and an aqueous solution being saturated with sodium chloride, then dried over anhydrous sodium sulfate. The residue obtained by removal of the solvent by distillation was purified by use of a silica gel column chromatography (eluent: n-hexane/ethyl acetate=4/1), there was obtained 1-nitro-2-(4-nitrophenylthio)imidazole (1.0 g, yield: 84%) as yellow powdery product.

$^1$H-NMR (CDCl$_3$) δ (ppm): 6.91 (1H, d, J=2.0 Hz), 7.82 (1H, d, J=2.0 Hz), 7.84 (2H, d, J=8.8 Hz), 8.30 (2H, d, J=8.8 Hz).

Reference Example 17

Preparation of 1-nitro-2-(2-nitrophenylthio) imidazole

To chloroform (10 ml) suspension of 2-(2-nitrophenylthio)imidazole (500 mg) and tetra-n-butylammonium nitrate (1.0 g) was added anhydrous trifluoroacetic acid (0.64 ml) at −20° C., then the reaction mixture was stirred at −10° C. for 30 minutes. To the reaction mixture was added ice-water, after being stirred for a while, ethyl acetate was added and the organic layer was taken by separation. The ethyl acetate layer was washed with water, an aqueous solution being saturated with sodium hydrogencarbonate and an aqueous solution being saturated with sodium chloride, then dried over anhydrous sodium sulfate. The residue obtained by removal of the solvent by distillation was purified by use of a silica gel column chromatography (eluent: n-hexane/ethyl acetate=13/7), there was obtained 1-nitro-2-(2-nitrophenylthio)imidazole (510 mg, yield: 87%) as yellow powdery product.

$^1$H-NMR (CDCl$_3$) δ (ppm): 6.98 (1H, d, J=2.0 Hz), 7.49-7.69 (3H, m), 7.85 (1H, d, J=2.0 Hz), 8.11-8.19 (1H, m).

Reference Example 18

Preparation of 2-(2-chloro-6-nitrophenylthio)-1-nitroimidazole

To chloroform (10 ml) suspension of 2-(2-chloro-6-nitrophenylthio)imidazole (500 mg) and tetra-n-butyl ammonium nitrate (893 mg) was added anhydrous trifluoroacetic acid (0.55 ml) at −20° C., then stirred at −10° C. for 3 hours. Ice-water was added to the reaction mixture, and after being stirred for a while, ethyl acetate was added, and the organic layer was taken by separation. The ethyl acetate layer was washed with water, an aqueous solution being saturated with sodium hydroencarbonate, an aqueous solution being saturated with sodium chloride, then dried over anhydrous sodium sulfate. The residue obtained by removal of the solvent by distillation was purified by use of a silica gel column chromatography (eluent: n-hexane/ethyl acetate=13/7), there was obtained 2-(2-chloro-6-nitrophenylthio)-1-nitroimidazole (506 mg, yield: 85%) as yellow powdery product.

$^1$H-NMR (CDCl$_3$) δ (ppm): 6.85 (1H, d, J=2.0 Hz), 7.60 (1H, t, J=8.0 Hz), 7.74 (1H, d, J=2.0 Hz), 7.80 (1H, dd, J=1.3, 8.0 Hz), 7.81 (1H, dd, J=1.3, 8.0 Hz).

Reference Example 19

Preparation of (R)-1-(2-methyl-2-oxiranylmethyl)-2-(4-nitrophenylthio)imidazole

To N,N-dimethylformamide (5 ml) solution of 2-(4-nitrophenylthio)imidazole (500 mg) was added sodium hydride (90 mg) at 0° C., then reaction mixture was stirred at a room temperature for 30 minutes. After being cooled again the reaction mixture to 0° C., 2-methyl-2-oxiranylmethyl(S)-4-nitrobenzenesulfonate (618 mg) was added and stirred at a room temperature for 3.5 hours. Water and ethyl acetate were added to the reaction mixture, the organic layer was taken by separation. The ethyl acetate layer was washed with water and an aqueous solution being saturated with sodium chloride, then dried over anhydrous sodium sulfate. The residue obtained by removal of the solvent by distillation was purified by use of a silica gel column chromatography (eluent: dichloromethane/ethyl acetate=17/3), there was obtained (R)-1-(2-methyl-2-oxiranylmethyl)-2-(4-nitrophenylthio)imidazole (604 mg, yield: 91%) as yellow oily product.

$^1$H-NMR (CDCl$_3$) δ (ppm): 1.21 (3H, s), 2.52 (1H, d, J=4.3 Hz), 2.63 (1H, d, J=4.3 Hz), 3.98 (1H, d, J=14.8 Hz), 4.39 (1H, d, J=14.8 Hz), 7.21 (2H, d, J=9.0 Hz), 7.32 (1H, d, J=1.3 Hz), 7.34 (1H, J=1.3 Hz), 8.10 (2H, d, J=9.0 Hz).

Reference Example 20

Preparation of 1-(2-cyanoethyl)-2-(4-nitrophenylthio)-imidazole

To acrylonitrile (10 ml) suspension of 2-(4-nitrophenylthio)imidazole (500 mg) was added 1,8-diazabicyclo[5.4.0]undecene-7 (0.04 ml), the reaction mixture was stirred for 1 hour under refluxing. The residue obtained by concentration was purified by use of a basic silica gel column chromatography (eluent: dichloromethane), the thus obtained solid was recrystallized from dichloromethane-tert-butylmethyl ether, there was obtained 1-(2-cyanoethyl)-2-(4-nitrophenylthio)imidazole (454 mg, yield: 74%) as colorless granular product.

$^1$H-NMR (CDCl$_3$) δ (ppm): 2.72 (2H, t, J=6.8 Hz), 4.35 (2H, t, J=6.8 Hz), 7.20 (2H, d, J=9.0 Hz), 7.34 (1H, d, J=1.3 Hz), 7.38 (1H, d, J=1.3 Hz), 8.13 (2H, d, J=9.0 Hz).

Reference Example 21

Preparation of 3-(4-trifluoromethylphenyl)-2-propenyl(S)-4-{3-[4-nitro-2-(4-nitrophenylthio)imidazol-1-yl]-2-hydroxy-2-methylpropyl}piperazine-1-carboxylate N,N-Dimethylformamide (0.5 ml) solution of (R)-1-(2-methyl-2-oxiranylmethyl)-4-nitro-2-(4-nitrophenylthio)imidazole (100 mg) and 3-(4-trifluoromethylphenyl)-2-propenyl piperazine-1-carboxylate (103 mg) was stirred at 60° C. for 1 day. Water and ethyl acetate were added to the reaction mixture, and the organic layer was taken by separation. The ethyl acetate layer was washed with water and an aqueous solution being saturated with sodium chloride, then dried over anhydrous sodium sulfate. The residue obtained by removal of the solvent by distillation was purified by use of a silica gel column chromatography (eluent: dichloromethane/methanol=50/1 to 30/1) and a basic silica gel column chromatography (eluent: dichlomethane), there was obtained 3-(4-trifluoromethylphenyl)-2-propenyl(S)-4-{3-[4-nitro-2-(4-nitrophenylthio)imidazol-1-yl]-2-hydroxy-2-methylpropyl] piperazin-1-carboxylate (173 mg, yield: 90%) as pale yellow amorphous product.

$^1$H-NMR (DMSO-d$_6$) δ (ppm): 1.01 (3H, s), 2.25-2.64 (6H, m), 3.15-3.50 (4H, m), 4.12 (1H, d, J=14.0 Hz), 4.35 (1H, d, J=14.0 Hz), 4.71 (2H, d, J=5.3 Hz), 5.00 (1H, s), 6.55 (1H, td, J=5.3, 16.0 Hz), 6.74 (1H, d, J=16.0 Hz), 7.49 (2H, d, J=9.0 Hz) 7.69 (4H, s), 8.18 (2H, d, J=9.0 Hz), 8.55 (1H, s).

Reference Example 22

Preparation of 3-(4-trifluoromethylphenyl)-2-propenyl(S)-4-{3-[4-nitro-2-(2-nitrophenylthio)imidazol-1-yl]-2-hydroxy-2-methylpropyl}piperazin-1-carboxylate N,N-Dimethylformamide (0.25 ml) solution of (R)-1-(2-methyl-2-oxiranylmethyl)-4-nitro-2-(2-nitrophenylthio)imidazole (50 mg) and 3-(4-trifluoromethylphenyl)-2-propenyl piperazin-1-carboxylate (51 mg) was stirred at 60° C. for 1 day. Water and ethyl acetate were added to the reaction mixture, the organic layer was taken by separation. The ethyl acetate layer was washed with water, an aqueous solution being saturated with sodium chloride, then dried over anhydrous sodium sulfate. The residue obtained by removal of the solvent by distillation was purified by use of a thin layer chromatography (eluent: dichloromethane/methanol=30/1), there was obtained 3-(4-trifluoromethylphenyl)-2-propenyl(S)-4-{3-[4-nitro-2-(2-nitrophenylthio)imidazol-1-yl]-2-hydroxy-2-methylpropyl}piperazin-1-carboxylate (86 mg, yield: 87%) as yellow amorphous product.

$^1$H-NMR (CDCl$_3$) δ (ppm): 1.08 (3H, s), 2.29 (1H, d, J=14.0 Hz), 2.40-2.71 (5H, m, including 2.44, d, J=14.0 Hz), 3.20 (1H, br.s), 3.50 (4H, br.s), 4.09 (2H, s), 4.77 (2H, d, J=6.0 Hz), 6.39 (1H, td, J=6.0, 16.0 Hz), 6.65 (1H, d, J=16.0 Hz), 6.96 (1H, dd, J=1.0, 8.0 Hz), 7.39 (1H, dt, J=1.0, 8.0 Hz), 7.46-7.53 (3H, m, including 7.49, d, J=8.0 Hz), 7.58 (2H, d, J=8.0 Hz), 8.27 (1H, dd, J=1.0, 8.0 Hz), 8.30 (1H, s).

Reference Example 23

Preparation of 3-(4-trifluoromethylphenyl)-2-propenyl(S)-4-{3-[2-(2-chloro-6-nitrophenylthio)-4-nitroimidazol-1-yl]-2-hydroxy-2-methylpropyl}piperazin-1-carboxylate N,N-Dimethylformamide (0.25 ml) solution of (R)-2-(2-chloro-6-nitrophenylthio)-1-(2-methyl-2-oxiranylmethyl)-4-nitroimidazole (55 mg) and 3-(4-trifluoromethylphenyl)-2-propenyl piperazin-1-carboxylate (51 mg) was stirred at 60° C. for 1 day. To the reaction mixture was added water and ethyl acetate, the organic layer was taken by separation. The ethyl acetate layer was washed with water and an aqueous solution being saturated with sodium chloride, then dried over anhydrous sodium sulfate. The residue obtained by removal of the solvent by distillation was purified by use of a thin layer chromatography (eluent: dichloromethane/methanol=30/1), there was obtained 3-(4-trifluoromethylphenyl)-2-propenyl(S)-4-{3-[2-(2-chloro-6-nitrophenylthio)-4-nitroimidazol-1-yl]-2-hydroxy-2-methylpropyl}piperazin-1-carboxylate (91 mg, yield: 87%) as yellow amorphous product.

$^1$H-NMR (CDCl$_3$) δ(ppm): 1.20 (3H, s), 2.42 (1H, d, J=14.0 Hz), 2.48-2.77 (5H, m, including 2.52, d, J=14.0 Hz) 3.10 (1H, br.s), 3.55 (4H, br.s), 4.13 (1H, d, J=14.5 Hz), 4.24 (1H, d, J=14.5 Hz), 4.78 (2H, d, J=6.0 Hz), 6.40 (1H, td, J=6.0, 16.0 Hz), 6.66 (1H, d, J=16.0 Hz), 7.46 (1H, t, J=8.0 Hz), 7.49 (2H, d, J=8.0 Hz), 7.58 (2H, d, J=8.0 Hz), 7.67 (1H, dd, J=1.0, 8.0 Hz), 7.80 (1H, dd, J=1.0, 8.0 Hz), 7.97 (1H, s).

Reference Example 24

Preparation of 3-(4-trifluoromethylphenyl)-2-propenyl(S)-4-{3-[4-nitro-2-(4-nitrobenzenesulfonyl)imidazol-1-yl]-2-hydroxy-2-methylpropyl]piperazin-1-carboxylate N,N-Dimethylformamide (0.18 ml) solution of (R)-1-(2-methyl-2-oxiranylmethyl)-4-nitro-2-(4-nitrobenzenesulfonyl)imidazole (36 mg) and 3-(4-trifluoromethylphenyl)-2-propenyl piperazin-1-carboxylate (34 mg) was stirred at 60° C. for 1 day. To the reaction mixture was added water and ethyl acetate, the organic layer was taken by separation. The ethyl acetate layer was washed with water and an aqueous solution being saturated with sodium chloride, then dried over anhydrous sodium sulfonate. The residue obtained by removal of the solvent by distillation was purified by use of a thin layer chromatography (eluent: dichloromethane/methanol=30/1), there was obtained 3-(4-trifluoromethylphenyl)-2-propenyl(S)-4-{3-[4-nitro-2-(4-nitrobenzenesulfonyl)imidazol-1-yl]-2-hydroxy-2-methylpropyl]piperazin-1-carboxylate (45 mg, yield: 67%) as pale yellow amorphous product.

$^1$H-NMR (CDCl$_3$) δ(ppm): 1.21 (3H, s), 2.44 (1H, d, J=14.0 Hz), 2.53-2.81 (5H, m, including 2.62, d, J=14.0 Hz) 3.40 (1H, br.s), 3.56 (4H, br.s), 4.54 (2H, s), 4.79 (2H, d, J=6.0 Hz), 6.40 (1H, td, J=6.0, 16.0 Hz), 6.66 (1H, d, J=16.0 Hz), 7.49 (2H, d, J=8.0 Hz), 7.58 (2H, d, J=8.0 Hz), 8.13 (1H, s), 8.29 (2H, d, J=9.0 Hz), 8.46 (2H, d, J=9.0 Hz).

In the said reaction, further cyclized 3-(4-trifluoromethylphenyl)-2-propenyl(S)-4-(2-methyl-6-nitro-2,3-dihydroimidazo[2,1-b]-oxazol-2-yl)methylpiperazin-1-carboxylate (7 mg, yield: 14%) was also obtained.

Reference Example 25

Preparation of 3-(4-trifluoromethylphenyl)-2-propenyl(S)-4-(2-methyl-6-nitro-2,3-dihydroimidazo[2,1-b]oxazol-2-ylmethyl)piperazin-1-carboxylate To N,N-dimethylformamide (1 ml) solution of 3-(4-trifluoromethylphenyl)-2-propenyl(S)-4-{3-[4-nitro-2-(4-nitrophenylthio)imidazol-1-yl]-2-hydroxy-2-methylpropyl} piperazin-1-carboxylate (100 mg) was added sodium tert-butoxide (19 mg) at 0° C., and stirred at the same temperature for 20 minutes. To the reaction mixture was added water and ethyl acetate, the organic layer was taken by separation. The ethyl acetate layer was washed with an aqueous solution of 5% potassium carbonate, water, and an aqueous solution being saturated with sodium chloride, then dried over anhydrous sodium sulfate. The residue obtained by removal of the solvent by distillation was purified by use of a basic silica gel chromatography (eluent: dichloroethane/ethyl acetate=9/1) and a slica gel column chromatography (eluent: dichloromethane/ethyl acetate/methanol=20/20/1), there was obtained 3-(4-trifluoromethylphenyl)-2-propenyl(S)-4-(2-methyl-6-nitro-2,3-dihydroimidazo-[2,1-b]oxazol-2-ylmethyl)piperazin-1-carboxylate (40 mg, yield: 54%) as yellow amorphous product.

Reference Example 26

Preparation of 3-(4-trifluoromethylphenyl)-2-propenyl(S)-4-(2-methyl-6-nitro-2,3-dihydroimidazo[2,1-b]oxazol-2-ylmethyl)piperazin-1-carboxylate To N,N-dimethylformamide (0.9 ml) solution of 3-(4-trifluoromethylphenyl)-2-propenyl(S)-4-{3-[4-nitro-2-(2-nitrophenylthio)imidazol-1-yl]-2-hydroxy-2-methylpropyl}piperazin-1-carboxylate (89 mg) was added sodium tert-butoxide (16 mg) at 0° C., and stirred at the same temperature for 30 minutes. To the reaction mixture was added water and ethyl acetate, the organic layer was taken by separation. The ethyl acetate layer was washed with an aqueous solution of 5% potassium carbonate, water, and an aqueous solution being saturated with sodium chloride, then dried over anhydrous sodium sulfate. The residue obtained by removal of the solvent by distillation was purified by use of a thin layer chromatography (eluent: dichloromethane/ethyl acetate/methanol=15/15/1), there was obtained 3-(4-trifluoromethylphenyl)-2-propenyl(S)-4-[(2-methyl-6-nitro-2,3-dihydroimidazo-[2,1-b]oxazol-2-yl)methyl]piperazin-1-carboxylate (38 mg, yield: 59%) as pale yellow amorphous product.

Reference Example 27

Preparation of 3-(4-trifluoromethylphenyl)-2-propenyl(S)-4-(2-methyl-6-nitro-2,3-dihydroimidazo[2,1-b]oxazol-2-ylmethyl)piperazin-1-carboxylate To N,N-dimethylformamide (0.9 ml) solution of 3-(4-trifluoromethylphenyl)-2-propenyl(S)-4-{3-[2-(2-chloro-6-nitrophenylthio)-4-nitroimidazol-1-yl]-2-hydroxy-2-methylpropyl}piperazin-1-carboxylate (89 mg) was added sodium tert-butoxide (16 mg) at 0° C., and stirred at the same temperature for 30 minutes. To the reaction mixture was added water and ethyl acetate, the organic layer was taken by separation. The ethyl acetate layer was washed with an aqueous solution of 5% potassium carbonate, water, and an aqueous solution being saturated with sodium chloride, then dried over anhydrous sodium sulfate. The residue obtained by removal of the solvent by distillation was purified by use of a thin layer chromatography (eluent: dichloromethane/ethyl acetate/methanol=15/15/1), there was obtained 3-(4-trifluoromethylphenyl)-2-propenyl(S)-4-(2-methyl-6-nitro-2,3-dihydroimidazo[2,1-b]oxazol-2-ylmethyl)piperazin-1-carboxylate (32 mg, yield: 51%) as pale yellow amorphous product.

Reference Example 28

Preparation of 3-(4-trifluoromethylphenyl)-2-propenyl(S)-4-(2-methyl-6-nitro-2,3-dihydroimidazo[2,1-b]oxazol-2-ylmethyl)piperazin-1-carboxylate To N,N-dimethylformamide (0.5 ml) solution of 3-(4-trifluoromethylphenyl)-2-propenyl(S)-4-{3-[4-nitro-2-(4-nitrobenzenesulfonyl)imidazol-1-yl]-2-hydroxy-2-methylpropyl}piperazin-1-carboxylate (45 mg) was added sodium tert-butoxide (8 mg) at 0° C., and stirred at the same temperature for 30 minutes. To the reaction mixture was added water and ethyl acetate, the organic layer was taken by separation. The ethyl acetate layer was washed with an aqueous solution of 5%-potassium carbonate, water, and an aqueous solution being saturated with sodium chloride, then dried over anhydrous sodium sulfate. The residue obtained by removal of the solvent by distillation was purified by use of a thin layer chromatography (eluent: dichloromethane/ethyl acetate/methanol=15/15/1), there was obtained 3-(4-trifluoromethylphenyl)-2-propenyl(S)-4-(2-methyl-6-nitro-2,3-dihydroimidazo-[2,1-b]oxazol-2-ylmethyl)piperazin-1-carboxylate (13 mg, yield: 39%) as pale yellow amorphous product.

Reference Example 29

Preparation of (R)-2-methyl-6-nitro-2-{4-[4-(4-trifluoromethoxyphenoxy)piperidin-1-yl]phenoxymethyl}-2,3-dihydroimidazo[2,1-b]oxazole 4-[4-(4-Trifluoromethoxyphenoxy)piperidin-1-yl]phenol (693 mg) was dissolved in N,N-dimethylformamide (3 ml), then under ice-cooling condition, sodium hydride (86 mg) was added, the reaction mixture was stirred at 70-75° C. for 20 minutes. The reaction mixture was ice-cooled, a solution prepared by dissolving (R)-2-bromo-4-nitro-1-(2-methyl-2-oxiranylmethyl)imidazole (720 mg) prepared in example 6 in N,N-dimethylformamide (3 ml) was added and stirred at 70-75° C. for 20 minutes. The reaction mixture was turned back to a room temperature, ice-water (25 ml) was added, and extracted 3 times with dichloromethane (50 ml). The organic layers were combined, after being washed with water 3 times, the organic layer was dried over anhydrous magnesium sulfate. After being filterated under a reduced pressure, the filtrate was concentrated, and the obtained residue was purified by use of a silica gel column chromatography (eluent: dichloromethane/ethyl acetate=3/1). Recrystallized from ethyl acetate/diisopropyl ether, there was obtained (R)-2-methyl-6-nitro-2-{4-[4-(4-trifluoromethoxyphenoxy)piperidin-1-yl]phenoxymethyl}-2,3-dihydroimidazo[2,1-b]oxazole (343 mg, yield: 33%) as pale yellow powder product.

Reference Example 30

(1) Preparation of 3-(4-trifluoromethylphenyl)-2-propenyl(S)-4-[3-(2-bromo-4-nitroimidazol-1-yl)-2-hydroxy-2-methylpropyl]piperazin-1-carboxylate Mixture of (R)-2-bromo-4-nitro-1-(2-methyl-2-oxiranylmethyl)imidazole (2.04 g) prepared in example 6,3-(4-trifluoromethylphenyl)-2-propenyl piperazin-1-carboxylate (2.69 g) and N,N-dimethylformamide (10 ml) was stirred at 50° C. for 20 hours. The reaction mixture was turned back to a room temperature, water (45 ml) was added, then extracted twice with ethyl acetate (15 ml). The organic layers were combined together, washed with water 3 times, dried over anhydrous sodium sulfate. After being filtrated under a reduced pressure, the residue thus obtained was purified by use of a silica gel column chromatography (eluent: n-hexane/ethyl acetate=1/2), there was obtained 3-(4-trifluoromethylphenyl)-2-propenyl(S)-4-[3-(2-bromo-4-nitroimidazol-1-yl)-2-hydroxy-2-methylpropyl]piperazin-1-carboxylate (3.77 g, yield: 84%)
$^1$H-NMR (CDCl$_3$) δ(ppm): 1.16 (3H, s), 2.36 (1H, d, J=14.0 Hz), 2.43-2.76 (5H, m), 3.21 (1H, s), 3.41-3.57 (4H, m), 4.01 (2H, s), 4.78 (2H, dd, J=1.0 Hz, 6.1 Hz), 6.29-6.43 (1H, m), 6.66 (1H, d, J=16.0 Hz), 7.48 (2H, d, J=8.3 Hz), 7.58 (2H, d, J=8.3 Hz), 8.10 (1H, s).

(2) Preparation of 3-(4-trifluoromethylphenyl)-2-propenyl(S)-4-(2-methyl-6-nitro-2,3-dihydroimidazo[2,1-b]oxazol-2-ylmethyl)piperazin-1-carboxylate 3-(4-Trifluoromethylphenyl)-2-propenyl(S)-4-[3-(2-bromo-4-nitroimidazol-1-yl)-2-hydroxy-2-methylpropenyl]piperazin-1-carboxylate (3.5 g) was dissolved in N,N-dimethylformamide (10.5 ml), under ice-cooling condition, sodium hydride (316 mg) was added, the reaction mixture was stirred at the same temperature for 1.5 hours. Ethyl acetate (3.5 ml) and water (24.5 ml) were added to the reaction mixture, and stirred for 30 minutes. Separated out crystals were collected by filtration, then washed with water. The crystals were purified by use of a silica gel column chromatography (eluent: ethyl acetate). Recrystallized from 2-propanol/water, there was obtained 3-(4-trifluoromethylphenyl)-2-propenyl(S)-4-(2-methyl-6-nitro-2,3-dihydroimidazo[2,1-b]oxazol-2-ylmethyl)piperazine (2.07 g, yield: 69%) as pale yellow powder product.

Reference Example 31

Preparation of (R)-(–)-1-(tert-butylmethylsilanyloxy)-3-chloropropan-2-ol

To N,N-dimethylformamide (40 ml) solution of (R)-(–)-3-chloro-1,2-propanediol (7 g), under ice-cooling and stirring condition, were added tert-butyldimethylchlorosilane (10.6 g) and imidazole (5.2 g), then stirred at a room temperature overnight. Ice-water (120 ml) was added to the reaction mixture, and extracted with ethyl acetate (50 ml) 3 times, the extracts were combined together and washed with an aqueous solution being saturated with sodium chloride, then dried over anhydrous magnesium sulfate. After being filtrated under a reduced pressure, the filtrate was concentrated, there was obtained (R)-(–)-1-(tert-butyldimethylsilanyloxy)-3-chloropropan-2-ol (13.24 g, yield: 92.4%) as colorless liquid product.

$^1$H-NMR (CDCl$_3$) δ(ppm): 0.09 (6H, s), 0.91 (9H, s), 3.75-3.62 (2H, m), 3.67-3.72 (2H, m), 3.81-3.89 (1H, m).

Reference Example 32

Preparation of 1-(tert-butyldimethylsilanyloxy)-3-chloro-2-(tetrahydropyran-2-yloxy)propane (R)-(–)-1-(tert-Butyldimethylsilanyloxy)-3-chloropropan-2-ol (11.19 g) prepared in reference example 31 was dissolved in dichloromethane (20 ml), then 3,4-dihydro-2H-pyran (5.87 ml) and pyridinium p-toluenesulfonate (catalytic amount) were added, then the reaction mixture was stirred at a room temperature overnight. The reaction mixture was concentrated under a reduced pressure, the residue was purified by use of a silica gel column chromatography (eluent: n-hexane/ethyl acetate=20/1), there was obtained 1-(t-butyldimethylsilanyloxy)-3-chloro-2-(tetrahydropyran-2-yloxy)propane (14.14 g, yield: 92.0%) as colorless liquid product.

$^1$H-NMR (CDCl$_3$) δ(ppm): 0.07 (6H, s), 0.89 (9H, s), 1.45-1.89 (6H, m), 3.43-4.03 (7H, m), 4.76-4.80 (1H, m).

Reference Example 33

Preparation of (3R)-tetrahydropyranyloxy-6-nitro-2H-3,4-dihydro[2,1-b]imidazopyran To N,N-dimethylformamide (60 ml) solution of 2-bromo-1-[3-hydroxy-2-(tetrahydropyran-2-yloxy)propyl]-4-nitro-1H-imidazole (8.51 g) prepared in example 29 was added sodium hydride (1.07 g) under ice-cooling and stirring condition, then the reaction mixture was stirred at a room temperature for 3 hours. Ice-water was added to the reaction mixture, then extracted twice with ethyl acetate (200 ml), and the extract was washed with an aqueous solution being saturated with sodium chloride, then dried over anhydrous magnesium sulfate. After being filtrated under a reduced pressure, the filtrate was concentrated under a reduced pressure. The residue thus obtained was purified by use of a silica gel column chromatography (eluent: dichloromethane/ethyl acetate=10/1), crystallized from dichloromethane-diisopropyl ether, there was obtained (3R)-tetrahydropyranyloxy-6-nitro-2H-3,4-dihydro[2,1-b]imidazopyran (3.3 g, yield: 50%) as white powdery product.

Example 8

Preparation of 2-chloro-4-nitroimidazole

Nitronium tetrafluoroborate (398 mg) was dissolved in nitromethane (5 ml), next 2-chloroimidazole (205 mg) was added, the reaction mixture was stirred at a room temperature for 1 hour. The reaction mixture was neutralized with an aqueous solution of sodium hydrogencarbonate, then was turned back to acidic by adding hydrochloric acid, the separated 2-chloro-4-nitroimidazole (137 mg) was collected by filtration. The filtrate was extracted with ethyl acetate-methanol, the solid matter obtained from the organic layer was triturated with diethyl ether, 2-chloro-4-nitroimidazole (103 mg) was obtained. The sum of 240 mg (yield: 81.3%) of 2-chloro-4-nitroimidazole was obtained as colorless solid product.

$^1$H-NMR (DMSO-d$_6$) δ(ppm): 8.44 (1H, s), 14.19 (1H, bs).

Example 9

Preparation of 2-chloro-4-nitroimidazole

2-Chloro-5-iodo-4-nitroimidazole (273 mg) was dissolved in ethanol (5 ml), then triethylamine (420 μl) and 10% palladium-carbon (27 mg) were added, the reaction mixture was subjected to hydrogenation at a room temperature under normal pressure for 3 hours, there was obtained 2-chloro-4-nitroimidazole (124 mg, yield: 84.1%) as colorless solid product.

$^1$H-NMR (DMSO-d$_6$) δ(ppm): 8.44 (1H, s), 14.19 (1H, bs).

Example 10

Preparation of 2-chloro-4-nitroimidazole

2-Chloro-5-iodo-4-nitroimidazole (273 mg) was dissolved in ethanol (5 ml), then triethylamine (420 μl) and 20% palladium hydroxide-carbon (27 mg) were added, the reaction mixture was subjected to hydrogenation at a room temperature under normal pressure for 5 hours, there was obtained 2-chloro-4-nitroimidazole (123 mg, yield: 83.4%) as colorless solid product.

$^1$H-NMR (DMSO-d$_6$) δ(ppm): 8.44 (1H, s), 14.19 (1H, bs).

Example 11

Preparation of 2-chloro-4-nitroimidazole

2-Chloro-5-iodo-4-nitroimidazole (545 mg) was dissolved in ethanol (10 ml), then triethylamine (840 μl) and 10% palladium-carbon (54 mg) were added, the reaction mixture was subjected to hydrogenation at hydrogen pressure of 4 kg/cm2 by use of Pearl reduction equipment, there was obtained 2-chloro-4-nitroimidazole (246 mg, yield: 83.4%) as colorless solid matter.

$^1$H-NMR (DMSO-d$_6$) δ(ppm): 8.44 (1H, s), 14.19 (1H, bs).

Example 12

Preparation of 2-chloro-4-nitroimidazole

2-Chloro-5-iodo-4-nitroimidazole (273 mg) was suspended in 1,4-dioxane (5 ml), then tetra-n-butyl ammonium borohydride (515 mg) was added, the reaction mixture was heated and refluxed for 10 hours. Then diluted hydrochloric acid was added to the reaction mixture, and extracted with ethyl acetate. The organic layer was treated with concentrated hydrochloric acid, the separated matters were collected by filtration. The filtrate was extracted with ethyl acetate, the separated matter obtained from the organic layer was combined together with the previously obtained solid matter and purified by use of a silica gel column chromatography (eluent: n-hexane/ethylacetate=3/1 to 2/1), there was obtained 2-chloro-4-nitroimidazole (107 mg, yield: 72.5%).

$^1$H-NMR (DMSO-d$_6$) δ(ppm): 8.44 (1H, s), 14.19 (1H, bs).

Example 13

Preparation of 4-nitro-2-(4-nitrophenylthio)imidazole

Chlorobenzene (5 ml) solution of 1-nitro-2-(4-nitrophenylthio)imidazole (250 mg) was stirred at 85-95° C. for 20 minutes. The residue obtained by concentration of the reaction mixture was purified by use of a silica gel column chromatography (eluent: dichloromethane-dichloromethane/methanol=50/1) and a thin layer chromatography (eluent: dichloromethane/methanol=10/1), there was obtained 4-nitro-2-(4-nitrophenylthio)imidazole (108 mg, yield: 44%) as yellow powder product.

$^1$H-NMR (DMSO-d$_6$) δ(ppm): 7.44 (2H, d, J=9.0 Hz), 8.18 (2H, d, J=9.0 Hz), 8.63 (1H, s), 14.24 (1H, br.s).

Example 14

Preparation of 4-nitro-2-(2-nitrophenylthio)imidazole

Chlorobenzene (10 ml) suspension of 1-nitro-2-(2-nitrophenylthio)imidazole (464 mg) was stirred at 70-80° C. for 30 minutes. The residue obtained by concentration of the reaction mixture was purified by use of a silica gel column chromatography (eluent: dichloromethane/ethyl acetate=19/1), there was obtained 4-nitro-2-(2-nitrophenylthio)imidazole (223 mg, yield: 49%) as yellow powder product.

$^1$H-NMR (DMSO-d$_6$) δ(ppm): 6.94 (1H, dd, J=1.3, 8.0 Hz), 7.51 (1H, dt, J=1.3, 8.0 Hz), 7.67 (1H, dt, J=1.3, 8.0 Hz), 8.31 (1H, dd, J=1.3, 8.0 Hz) 8.66 (1H, s,) 14.24 (1H, br.s).

Example 15

Preparation of 2-(2-chloro-6-nitrophenylthio)-4-nitroimidazole

Chlorobenzene (6 ml) solution of 2-(2-chloro-6-nitrophenylthio)-1-nitroimidazole (300 mg) was stirred at 70-80° C. for 30 minutes. The residue obtained by concentration of the reaction mixture was purified by use of a silica gel column chromatography (eluent: dichloromethane/ethyl acetate=19/1), there was obtained 4-nitro-2-(2-chloro-6-nitrophenylthio)imidazole (138 mg, yield: 46%) as yellow powder product.

$^1$H-NMR (DMSO-d$_6$) δ(ppm): 7.75 (1H, t, J=8.0 Hz), 7.97 (1H, dd, J=1.0, 8.0 Hz), 8.07 (1H, dd, J=1.0, 8.0 Hz), 8.44 (1H, s), 13.82 (1H, br.s).

Example 16

Preparation of (R)-1-(2-methyl-2-oxiranylmethyl)-4-nitro-2-(4-nitrophenylthio)imidazole 4-Nitro-2-(4-nitrophenylthio)imidazole (500 mg) and N,N-dimethylformamide (1.6 ml) suspension of 2-methyl-2-oxiranylmethyl(S)-4-nitrobenzenesulfonate (513 mg), potassium carbonate (337 mg) and cesium fluoride (57 mg) were stirred at a room temperature for 1.5 days. Water and ethyl acetate were added to the reaction mixture and the organic layer was taken by separation. The ethyl acetate layer was washed with water and an aqueous solution being saturated with sodium chloride, then dried over anhydrous sodium sulfate. The residue obtained by removal of the solvent by distillation was purified by use of a basic silica gel column chromatography (eluent: n-hexane/ethyl acetate=13/7 to 11/9), there was obtained (R)-1-(2-methyl-2-oxiranylmethyl)-4-nitro-2-(4-nitrophenylthio)imidazole (456 mg, yield: 74%) as pale yellow powder product.

$^1$H-NMR (CDCl$_3$) δ(ppm): 1.28 (3H, s), 2.54 (1H, d, J=3.5 Hz), 2.72 (1H, d, J=3.5 Hz), 4.04 (1H, d, J=14.5 Hz), 4.51 (1H, d, J=14.5 Hz), 7.42 (2H, d, J=9.0 Hz), 8.07 (1H, s), 8.17 (2H, d, J=9.0 Hz)

Example 17

Preparation of (R)-1-(2-methyl-2-oxiranylmethyl)-4-nitro-2-(2-nitrophenylthio)imidazole 4-Nitro-2-(2-nitrophenylthio)imidazole (100 mg) and N,N-dimethylformamide (0.5 ml) suspension of 2-methyl-2-oxiranylmethyl(S)-4-nitrobenzenesulfonate (119 mg), potassium carbonate (71 mg) and cesium fluoride (11 mg) were stirred at a room temperature for 3.5 days. Water and ethyl acetate were added to the reaction mixture and the organic layer was taken by separation. The ethyl acetate layer was washed with water and an aqueous solution being saturated with sodium chloride, then dried over anhydrous sodium sulfate. The residue obtained by removal of the solvent by distillation was purified by use of a basic silica gel column chromatography (eluent: n-hexane/ethyl acetate=11/9 to 1/1), then there was obtained (R)-1-(2-methyl-2-oxiranylmethyl)-4-nitro-2-(2-nitrophenylthio)imidazole (102 mg, yield: 79%) as yellow powder product.

$^1$H-NMR (CDCl$_3$) δ(ppm): 1.26 (3H, s), 2.54 (1H, d, J=4.0 Hz), 2.72 (1H, d, J=4.0 Hz), 3.98 (1H, d, J=14.5 Hz), 4.51 (1H, d, J=14.5 Hz), 6.95 (1H, dd, J=1.0, 8.0 Hz), 7.40 (1H, dt, J=1.0, 8.0 Hz), 7.51 (1H, dt, J=1.0, 8.0 Hz), 8.14 (1H, s), 8.29 (1H, dd, J=1.0, 8.0 Hz).

Example 18

Preparation of (R)-2-(2-chloro-6-nitrophenylthio)-1-(2-methyl-2-oxiranylmethyl)-4-nitroimidazole 2-(2-Chloro-6-nitrophenylthio)-4-nitroimidazole (113 mg) and N,N-dimethylformamide (0.5 ml) suspension of 2-methyl-2-oxiranylmethyl(S)-4-nitrobenzenesulfonate (119 mg), potassium carbonate (71 mg) and cesium fluoride (11 mg) were stirred at a room temperature for 3.5 days. Water and ethyl acetate were added to the reaction mixture and the organic layer was taken by separation. The ethyl acetate layer was washed with water and an aqueous solution being saturated with sodium chloride, then dried over anhydrous sodium sulfate. The residue obtained by removal of the solvent by distillation was purified by use of a basic silica gel column chromatography (eluent: n-hexane/ethyl acetate=11/9 to 1/1), then there was obtained (R)-2-(2-chloro-6-nitrophenylthio)-1-(2-methyl-2-oxiranylmethyl)-4-nitroimidazole (85 mg, yield: 61%) as yellow powdery product.

$^1$H-NMR (CDCl$_3$) δ(ppm): 1.43 (3H, s), 2.56 (1H, d, J=4.0 Hz), 2.76 (1H, d, J=4.0 Hz), 4.20 (1H, d, J=15.0 Hz), 4.53 (1H, d, J=15.0 Hz), 7.47 (1H, t, J=8.0 Hz), 7.68 (1H, dd, J=1.0, 8.0 Hz), 8.82 (1H, dd, J=1.0, 8.0 Hz), 7.87 (1H, s).

Example 19

Preparation of (R)-1-(2-methyl-2-oxiranylmethyl)-4-nitro-2-(4-nitrobenzenesulfonyl)imidazole To dichloromethane (4 ml) solution of (R)-1-(2-methyl-2-oxiranylmethyl)-4-nitro-2-(4-nitrophenylthio)imidazole (100 mg) was added m-chloroperbenzoic acid (160 mg) at 0° C., the reaction mixture was stirred at the same temperature for 14 hours. The reaction mixture was treated by use of a basic silica gel column chromatography (eluent: dichloromethane) to obtained crude product. To dichloromethane (4 ml) solution of this crude product was added m-chloroperbenzoic acid (110 mg) at 0° C., then stirred at a room temperature for 1 day. This reaction mixture was treated by use of a basic silica gel column chromatography (eluent: dichloromethane), thus obtained crude product was purified by use of a silia gel column chromatography (eluent: n-hexane/ethyl acetate=1/1), there was obtained (R)-1-(2-methyl-2-oxiranylmethyl)-4-nitro-2-(4-nitrobenzenesulfonyl)imidazole (85 mg, yield 77%) as white powder product.

$^1$H-NMR (CDCl$_3$) δ(ppm): 1.46 (3H, s), 2.56 (1H, d, J=3.9 Hz), 2.80 (1H, d, J=3.9 Hz), 4.43 (1H, d, J=14.7 Hz), 5.03 (1H, d, J=14.7 Hz), 7.94 (1H, s), 8.32 (2H, d, J=9.0 Hz), 8.46 (2H, d, J=9.0 Hz).

Example 20

Preparation of 4-nitro-2-(4-nitrobenzenesulfonyl)imidazole

To dichloromethane (20 ml)-ethanol (20 ml) suspension of 4-nitro-2-(4-nitrophenylthio)imidazole (1.0 g) was added m-chloroperbenzoic acid (2.0 g) at a room temperature, the reaction mixture was stirred at the same temperature for 8 hours. To the reaction mixture was added an aqueous solution of 5% sodium hydrogensulfite, and stirred overnight. Water was added, after being stirred vigorously, the insoluble matters were collected by filtration. Thus obtained solid matters were washed with water, then the solid matters were dispersed and washed under refluxing condition in methanol. The insoluble matters were collected by filtration, thus obtained solid matters were dispersed and washed under the condition similar to the above condition in dichloromethane-methanol, then dried, there was obtained 4-nitro-2-(4-nitrobenzenesulfonyl)imidazole (919 mg: yield 82%) as white powdery product.

$^1$H-NMR (DMSO-d$_6$) δ(ppm): 8.25 (2H, d, J=9.0 Hz), 8.48 (2H, d, J=9.0 Hz), 8.58 (1H, s).

Example 21

Preparation of (R)-1-(2-methyl-2-oxiranylmethyl)-4-nitro-2-(4-nitrobenzenesulfonyl)imidazole 4-Nitro-2-(4-nitrobenzenesulfonyl)imidazole (200 mg) and N,N-dimethylformamide (0.57 ml) suspension of 2-methyl-2-oxiranylmethyl(S)-4-nitrobenzenesulfonate (183 mg), potassium carbonate (120 mg) and cesium fluoride (20 mg) were stirred at a room temperature for 1.5 days. Water and ethyl acetate were added to the reaction mixture, and organic layer was taken by separation. The ethyl acetate layer was washed with water and an aqueous solution being saturated with sodium chloride, then dried over anhydrous sodium sulfate. The residue obtained by removal of the solvent by distillation was purified by use of a silica gel column chromatography (eluent: n-hexane/ethyl acetate=11/9 to 1/1), there was obtained (R)-1-(2-methyl-2-oxiranylmethyl)-4-nitro-2-(4-nitrobenzenesulfonyl)imidazole (76 mg, yield: 31%) as white powdery product.

$^1$H-NMR (CDCl$_3$) δ(ppm): 1.46 (3H, s), 2.56 (1H, d, J=3.9 Hz), 2.80 (1H, d, J=3.9 Hz), 4.43 (1H, d, J=14.7 Hz), 5.03 (1H, d, J=14.7 Hz), 7.94 (1H, s), 8.32 (2H, d, J=9.0 Hz), 8.46 (2H, d, J=9.0 Hz).

Example 22

Preparation of (R)-1-(2-methyl-2-oxiranylmethyl)-4-nitro-2-(4-nitrophenylthio)imidazole To chloroform (5 ml) solution of (R)-1-(2-methyl-2-oxiranylmethyl)-2-(4-nitrophenylthio)imidazole (200 mg) and tetra-n-butylammonium nitrate (230 mg) was added anhydrous trifluoroacetic acid (0.11 ml) at −20° C., and the reaction mixture was stirred at −20° C. to 0° C. for 7.5 hours. After being added 1N sodium hydroxide (2 ml) to the reaction mixture and stirred for 30 minutes, ethyl acetate and water were added, then the organic layer was taken by separation. The ethyl acetate layer was washed with an aqueous solution of 5% sodium hydrogensulfite, water and an aqueous solution being saturated with sodium chloride, then dried over anhydrous sodium sulfate. The residue obtained by removal of the solvent by distillation was purified by use of a thin layer chromatography (eluent: dichloromethane/ethyl acetate=9/1), there was obtained (R)-1-(2-methyl-2-oxiranylmethyl)-4-nitro-2-(4-nitrophenylthio)imidazole (15 mg, yield: 6.7%) as yellow amorphous product.

$^1$H-NMR (CDCl$_3$) δ(ppm): 1.28 (3H, s), 2.54 (1H, d, J=3.5 Hz), 2.72 (1H, d, J=3.5 Hz), 4.04 (1H, d, J=14.5 Hz), 4.51 (1H, d, J=14.5 Hz), 7.42 (2H, d, J=9.0 Hz), 8.07 (1H, s), 8.17 (2H, d, J=9.0 Hz).

Example 23

Preparation of (R)-1-(2-methyl-2-oxiranylmethyl)-2-methylthio-4-nitroimidazole

To chloroform (5 ml) solution of (R)-1-(2-methyl-2-oxiranylmethyl)-2-methylthioimidazole (128 mg) and tetra-n-butylammonium nitrate (230 mg) was added anhydrous trifluoroacetic acid (0.11 ml) at −20° C., and the reaction mixture was stirred at −20° C. to 0° C. for 5 hours. To the reaction mixture was added an aqueous solution of 1N sodium hydroxide (2 ml), after being stirred for 30 minutes, ethyl acetate and water were added, the organic layer was taken by separation. The ethyl acetate layer was washed with an aqueous solution of 5% sodium hydrogensulfite, water and an aqueous solution being saturated with sodium chloride, then dried over anhydrous sodium sulfate. The residue obtained by removal of the solvent by distillation was purified by use of a thin layer chromatography (eluent: n-hexane/ethyl acetate=1/1), there was obtained (R)-1-(2-methyl-2-oxiranylmethyl)-2-methylthio-4-nitroimidazole (13 mg, yield: 8.3%) as pale yellow oily product.

$^1$H-NMR (CDCl$_3$) δ(ppm): 1.36 (3H, s), 2.59 (1H, d, J=4.0 Hz), 2.73 (3H, s,) 2.74 (1H, d, J=4.0 Hz), 3.92 (1H, d, J=15.0 Hz), 4.23 (1H, d, J=15.0 Hz), 7.85 (1H, s).

Example 24

Preparations of 1-(2-cyanoethyl)-5-nitro-2-(4-nitrophenylthio)imidazole and 1-(2-cyanoethyl)-4-nitro-2-(4-nitrophenylthio)imidazole To chloroform solution of 1-(2-cyanoethyl)-2-(4-nitrophenylthio)imidazole (250 mg) and tetra-n-butylammonium nitrate (333 mg) was added anhydrous trifluoroacetic acid (0.16 ml) at −10° C., then the reaction mixture was stirred at 0° C. for 6.5 hours. To the reaction mixture was added 1N sodium hydroxide (2.4 ml), after being stirred for 30 minutes, ethyl acetate and water, then the organic layer was taken by liquid separation. The ethyl acetate was washed with water and an aqueous solution being saturated with sodium chloride, then dried over anhydrous sodium sulfate. The residue obtained by removal of the solvent by distillation was purified by use of a silica gel column chromatography (eluent: n-hexane/ethyl acetate=3/2 to 11/9 to 2/3), there were obtained 1-(2-cyanoethyl)-5-nitro-2-(4-nitrophenylthio)imidazole (36 mg, yield: 12%) as yellow oily product and 1-(2-cyanoethyl)-4-nitro-2-(4-nitrophenylthio)imidazole (29 mg, yield: 10%) as violet oily product.

(1) 5-Nitro compound: $^1$H-NMR (CDCl$_3$) δ(ppm): 2.99 (2H, t, J=6.5 Hz), 4.82 (2H, d, J=6.5 Hz), 7.64 (2H, d, J=9.0 Hz), 8.13 (1H, s), 8.24 (2H, d, J=9.0 Hz).

(2) 4-Nitro compound: $^1$H-NMR (CDCl$_3$) δ(ppm): 2.84 (2H, t, J=6.5 Hz), 4.43 (2H, t, J=6.5 Hz), 7.43 (2H, d, J=9.0 Hz), 8.09 (1H, s), 8.21 (2H, d, J=9.0 Hz).

Example 25

Preparation of 4-nitro-2-(4-nitrophenylthio)imidazole

To tetrahydrofuran (1 ml) solution of 1-(2-cyanoethyl)-5-nitro-2-(4-nitrophenylthio)imidazole (36 mg) was added 1,8-diazabicyclo[5.4.0]undecene-7 (0.02 ml) at a room temperature, and stirred at the same temperature for 5 hours. To the reaction mixture were added 1N hydrochloric acid (0.2 ml), water and ethyl acetate, then the organic layer was taken by liquid separation. The ethyl acetate layer was washed with water and an aqueous solution being saturated with sodium chloride, then dried over anhydrous sodium sulfate. The residue obtained by removal of the solvent by distillation was purified by use of a silica gel column chromatography (eluent: dichloromethane/ethyl acetate=4/1), there was obtained 4-nitro-2-(4-nitrophenylthio)imidazole (27 mg, yield 91%) as pale yellow powder product.

$^1$H-NMR (DMSO-d$_6$) δ(ppm): 7.44 (2H, d, J=9.0 Hz), 8.18 (2H, d, J=9.0 Hz), 8.63 (1H, s), 14.24 (1H, br.s).

Example 26

Preparation of 4-nitro-2-(4-nitrophenylthio)imidazole

To tetrahydrofuran (1 ml) solution of 1-(2-cyanoethyl)-4-nitro-2-(4-nitrophenylthio)imidazole (27 mg) was added 1,8-diazabicyclo[5.4.0]undecene-7 (0.02 ml) at a room temperature, and stirred at the same temperature for 3 hours. To the reaction mixture were added 1N hydrochloric acid (0.7 ml), water and ethyl acetate, then the organic layer was taken by liquid separation. The ethyl acetate layer was washed with water and an aqueous solution being saturated with sodium chloride, then dried over anhydrous sodium sulfate. The residue obtained by removal of the solvent by distillation was purified by use of a thin layer chromatography (eluent: dichloromethane/ethyl acetate=9/1), there was obtained 4-nitro-2-(4-nitrophenylthio)imidazole (13 mg, yield 58%) as reddish brown powdery product.

$^1$H-NMR (DMSO-d$_6$) δ(ppm): 7.44 (2H, d, J=9.0 Hz), 8.18 (2H, d, J=9.0 Hz), 8.63 (1H, s), 14.24 (1H, br.s).

Example 27

Preparation of (S)-2-bromo-1-(2-methyl-2-oxiranylmethyl)-4-nitroimidazole

A suspension of 2-bromo-4-nitroimidazole (100 g), 2-methyl-2-oxiranylmethyl(R)-4-nitrobenzenesulfonate (142.4 g), potassium carbonate (93.6 g) and cesium fluoride (15.8 g) in N,N-dimethylformamide (420 ml) was stirred at 35-40° C. for 26 hours. The reaction mixture was poured into water (1.2 liters) and extracted twice with ethyl acetate (1 liter). Ethyl acetate layers were combined together, after being washed twice with water (1.2 liters), further washed with an aqueous solution being saturated with sodium chloride (800 ml), then dried over anhydrous magnesium sulfate. After being filtrated under a reduced pressure, the filtrate was concentrated under a reduced pressure. The residue thus obtained was purified by use of a silica gel column chromatography (eluent: n-hexane/ethyl acetate=1/1), there was obtained (S)-2-bromo-1-(2-methyl-2-oxiranylmethyl)-4-nitroimidazole (112.3 g, yield: 82%) as yellow powdery product.

Melting point: 93.0-94.0° C.

$^1$H-NMR (CDCl$_3$) δ(ppm): 1.38 (3H, s), 2.61 (1H, d, J=4.0 Hz), 2.78 (1H, d, J=4.0 Hz), 4.00 (1H, d, J=14.9 Hz), 4.38 (1H, d, J=14.9 Hz), 7.92 (1H, s).

Optical purity: 96.4% e.e.

The optical purity was determined by a high performance liquid chromatography (HPLC) under the following conditions.

Column: CHIRALPAK AD (4.6 mmφ×250 mm) [manufactured by Daicel Chemical Industries, Inc.]
Moving bed: n-hexane/ethanol=4/1
Flow velocity: 1.0 ml/minute
Detection wave length: 254 nm.

Example 28

Preparation of 2-bromo-1-[3-(t-butyldimethylsilanyloxy)-2-(tetrahydropyran-2-yloxy)propyl]-4-nitroimidazole 2-Bromo-4-nitroimidazole (7.63 g) and 1-(tert-butyldimethylsilanyloxy)-3-chloro-2-(tetrahydropyran-2-yloxy)propane (12 g) were dissolved in N,N-dimethylformamide (80 ml), then potassium carbonate (6.6 g) and sodium iodide (6.3 g) were added thereto, and the reaction mixture was heated and stirred at 110° C. for 12 hours. Ice-water (240 ml) was added, extracted twice with ethyl acetate (150 ml), and the extracts were combined together and washed with an aqueous solution being saturated with sodium chloride (100 ml), then dried over anhydrous magnesium sulfate. After being filtrated under a reduced pressure, the filtrate was concentrated under a reduced pressure. The residue obtained was purified by use of a silica gel column chromatography (eluent: dichloromethane/ethyl acetate=100/1), there was obtained 2-bromo-1-[3-(t-butyldimethylsilanyloxy)-2-(tetrahydropyran-2-yloxy)propyl]-4-nitroimidazole (12.69 g, yield: 68.7%)

$^1$H-NMR (CDCl$_3$) δ(ppm): 0.08 (3H, s), 0.01 (3H, s), 0.91 (4.5H, s), 0.93 (4.5H, s), 1.39-1.80 (6H, m), 3.35-4.45 (8.5H, m), 4.65-4.68 (0.5H, m), 7.90 (0.5H, s), 8.01 (0.5H, s).

EI (m/z) M$^+$=464

Example 29

Preparation of 2-bromo-1-[3-hydroxy-2-(tetrahydropyran-2-yloxy)propyl]-4-nitroimidazole To tetrahydrofuran (120 ml) solution of 2-bromo-1-[3-(t-butyldimethylsilanyloxy)-2-(tetrahydropyran-2-yloxy)propyl)-4-nitroimidazole (12.7 g) prepared in Example 28, was added 1M tetra-n-butylammonium fluoride tetrahydrofuran solution (30 ml) under stirring and ice-cooling condition, the reaction mixture was stirred at a room temperature overnight. The reaction mixture was concentrated under a reduced pressure and the residue was diluted with ethyl acetate, washed with water and an aqueous solution being saturated with sodium chloride. After being dried over anhydrous magnesium sulfate, the residue was concentrated under a reduced pressure, thus obtained residue was purified by use of a silica gel column chromatography (eluent: dichloromethane/ethyl acetate=10/1), there was obtained 2-bromo-1-[3-hydroxy-2-(tetrahydropyran-2-yloxy)propyl]-4-nitroimidazole (8.51 g, yield: 89%) as colorless liquid product.

$^1$H-NMR (CDCl$_3$) δ(ppm): 1.50-1.94 (6H, m), 3.38-4.31 (8.5H, m), 4.67-4.71 (0.5H, m), 7.87 (0.5H, s), 8.01 (0.5H, s). EI(m/z) M$^+$=350

Example 30

Preparation of 1-[3-(t-butyldimethylsilanyloxy)-2-(tetrahydropyran-2-yloxy)propyl]-2-chloro-4-nitroimidazole Similar to Example 28, the objective compound was synthesized from 2-chloro-4-nitroimidazole (2.15 g) and 1-(tert-butyldimethylsilanyloxy)-3-chloro-2-(tetrahydropyran-2-yloxy)propane (12 g), there was obtained 1-[3-(tert-butyldimethylsilanyloxy)-2-(tetrahydropyran-2-yloxy)propyl]-2-chloro-4-nitroimidazole (3.03 g, yield: 74.3%) as colorless liquid product.

$^1$H-NMR (CDCl$_3$) δ(ppm): 0.08 (3H, s), 0.01 (3H, s), 0.91 (4.5H, s), 0.92 (4.5H, s), 1.46-1.80 (6H, m), 3.40-4.45 (8.5H, m), 4.65-4.68 (0.5H, m), 7.84 (0.5H, s), 7.96 (0.5H, s).

Example 31

Preparation of 2-chloro-1-[3-hydroxy-2-(tetrahydropyran-2-yloxy)propyl]-4-nitroimidazole Similar to Example 29, the objective compound was synthesized from 1-[3-(t-butyldimethylsilanyloxy)-2-(tetrahydropyran-2-yloxy)propyl]-2-chloro-4-nitroimidazole (3.03 g), there was obtained 2-chloro-1-[3-hydroxy-2-(tetrahydropyran-2-yloxy)propyl]-4-nitroimidazole (1.96 g, yield: 89%) as colorless liquid product.

$^1$H-NMR (CDCl$_3$) δ(ppm): 1.44-1.90 (6H, m), 3.37-4.25 (8.5H, m), 4.65-4.70 (0.5H, m), 7.84 (0.5H, s), 7.97 (0.5H, s).

The invention claimed is:

1. A method for preparing a 4-nitroimidazole compound represented by the formula (2a),

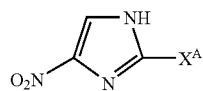

(2a)

wherein $X^A$ is a halogen atom,
which is characterized by reducing a 4-nitroimidazole compound represented by the formula (3),

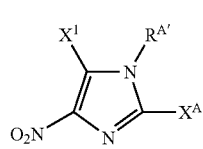

(3)

wherein $R^{A'}$ is a lower alkoxy group-substituted lower alkyl group, a phenyl-lower alkoxy group-substituted lower alkyl group, a cyano group-substituted lower alkyl group, or a phenyl-lower alkyl group which may have a lower alkoxy group as the substituent on the phenyl ring; $X^A$ and $X^1$ are each a halogen atom, and removing the $R^{A'}$ group from the obtained 1-substituted-4-nitroimidazole compound represented by the formula (1a),

(1a)

wherein $R^{A'}$ and $X^A$ are the same as defined above.

2. A method for preparing a 4-nitroimidazole compound represented by the formula (2a),

(2a)

wherein $X^A$ is a halogen atom,
which is characterized by reducing a 4-nitroimidazole compound represented by the formula (4),

(4)

wherein $X^A$ and $X^1$ are the each a halogen atom.

3. A method for preparing a 4-nitroimidazole compound represented by the formula (2b) or (2c),

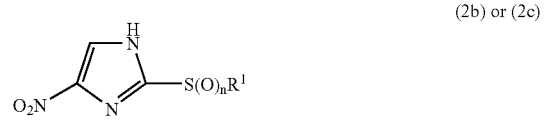

(2b) or (2c)

wherein $R^1$ is a phenyl group which may have 1 to 3 substituents, selected from the group consisting of a nitro group, a halogen atom and a lower alkyl group, in the phenyl ring; and n is 0 or an integer of 1 or 2,
which is characterized by removing $R^{A'}$ group from the 1-substituted-4-nitroimidazole compound represented by the formula (25) or (25a),

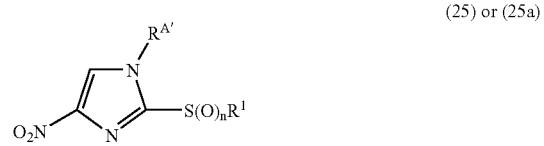

(25) or (25a)

wherein n and $R^1$ are the same as defined above; and $R^{A'}$ is a lower alkoxy group-substituted lower alkyl group, a phenyl-lower alkoxy group-substituted lower alkyl group, a cyano group-substituted lower alkyl group, a phenyl-lower alkyl group which may have a lower alkoxy group as the substituent on the phenyl ring.

* * * * *